(12) United States Patent
Zhang et al.

(10) Patent No.: US 11,225,551 B2
(45) Date of Patent: Jan. 18, 2022

(54) AMPHIPHILIC BLOCK COPOLYMER, PREPARATION METHOD THEREOF AND NANOMICELLE DRUG-LOADING SYSTEM

(71) Applicant: Fuyao Zhang, Shanghai (CN)

(72) Inventors: Fuyao Zhang, Shanghai (CN); Yuxiang Shao, Shanghai (CN); Huoming Li, Shanghai (CN)

(73) Assignee: SELECTION BIOSCIENCE LLC, Shanghai (CN)

(*) Notice: Subject to any disclaimer, the term of this patent is extended or adjusted under 35 U.S.C. 154(b) by 0 days.

(21) Appl. No.: 16/969,397

(22) PCT Filed: Feb. 12, 2019

(86) PCT No.: PCT/CN2019/074816
§ 371 (c)(1),
(2) Date: Aug. 12, 2020

(87) PCT Pub. No.: WO2019/158037
PCT Pub. Date: Aug. 22, 2019

(65) Prior Publication Data
US 2021/0047467 A1   Feb. 18, 2021

(30) Foreign Application Priority Data

Feb. 13, 2018 (CN) .......................... 201810153233.3

(51) Int. Cl.
| | |
|---|---|
| *C08G 65/48* | (2006.01) |
| *A61K 9/107* | (2006.01) |
| *C08G 63/87* | (2006.01) |
| *C08G 63/90* | (2006.01) |
| *C08G 63/91* | (2006.01) |
| *C08G 65/333* | (2006.01) |
| *B82Y 5/00* | (2011.01) |

(52) U.S. Cl.
CPC ............ *C08G 65/48* (2013.01); *A61K 9/1075* (2013.01); *C08G 63/87* (2013.01); *C08G 63/90* (2013.01); *C08G 63/91* (2013.01); *C08G 65/33327* (2013.01); *B82Y 5/00* (2013.01)

(58) Field of Classification Search
CPC .. C08G 65/48; C08G 65/87; C08G 65/33327; C08G 63/91; C08G 63/90; A61K 9/1075; B82Y 5/00
See application file for complete search history.

(56) References Cited

U.S. PATENT DOCUMENTS

| | | | |
|---|---|---|---|
| 7,879,317 B2* | 2/2011 | Seo ...................... | A61K 9/1075 424/70.11 |
| 9,393,312 B2* | 7/2016 | Liu ......................... | A61K 47/34 |
| 2010/0203142 A1* | 8/2010 | Zhang ................ | A61K 47/6935 424/487 |
| 2015/0361219 A1 | 12/2015 | Gu et al. | |

FOREIGN PATENT DOCUMENTS

| | | |
|---|---|---|
| CN | 101050276 A | 10/2007 |
| CN | 101580585 A | 11/2009 |
| CN | 101798383 A | 8/2010 |
| CN | 102321239 A | 1/2012 |
| CN | 101524546 B | 6/2012 |
| CN | 102532531 A | 7/2012 |
| CN | 102964588 A | 3/2013 |
| CN | 103768013 A | 5/2014 |
| CN | 103772686 A | 5/2014 |
| CN | 103980466 A | 8/2014 |
| CN | 105287377 A | 2/2016 |

(Continued)

OTHER PUBLICATIONS

Wang et al.; Journal of Nanoparticle Research, 2013, vol. 15, p. 1-16.*
Zhou, Z., et al.; International Journal of Pharmaceutics, 2017, p. 300-307.*
International Search Report and Written Opinion issued in International Patent Application No. PCT/CN2019/074816 dated May 16, 2019, 12 pages.
Lee et al., "Ionically Fixed Polymeric Nanoparticles as a Novel Drug Carrier", Pharmaceutical Research, Aug. 2007, vol. 24, No. 8, 1508-1516.
Tam et al., "Oligo(lactic acid)n-Paclitaxel Prodrugs for Poly(ethylene glycol)-block-poly(lactic acid) Micelles: Loading, Release, and Backbiting Conversion for Anticancer Activity", Journal of the American Chemical Society, 2016, vol. 138, 8674-8677.

(Continued)

*Primary Examiner* — Robert S Jones, Jr.
(74) *Attorney, Agent, or Firm* — MH2 Technology Law Group LLP

(57) ABSTRACT

The present invention relates to an amphiphilic block copolymer represented by formula I, a preparation method thereof, and a nanomicelle drug delivery system formed from the copolymer and a poorly soluble drug. The amphiphilic block copolymer includes a hydrophilic chain segment, a hydrophobic chain segment, and a linker for linking the hydrophilic chain segment to the hydrophobic chain segment. The linker contains an unsaturated structure, which can enhance the interaction between the poorly soluble drug and the copolymer to improve the drug loading ability and stability of the nanomicelle. The invention also relates to a nanomicelle drug-loading system, a preparation method thereof, and the use of the nanomicelle drug-loading system for preparing medicines for treating tumors, inflammation, diabetes, central nervous system diseases, cardiovascular diseases, and psychological disorders.

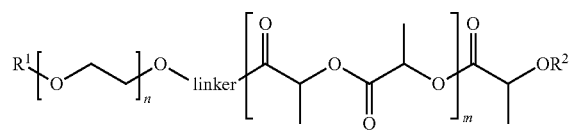

23 Claims, 10 Drawing Sheets

(56) References Cited

FOREIGN PATENT DOCUMENTS

| | | | |
|---|---|---|---|
| CN | 105399931 | A | 3/2016 |
| CN | 104961887 | B | 10/2016 |
| CN | 106265509 | A | 1/2017 |
| CN | 106349466 | A | 1/2017 |
| CN | 110156971 | A | 8/2019 |
| JP | 2001517603 | A | 10/2001 |
| JP | 2009102488 | A | 5/2009 |
| JP | 2014502286 | A | 1/2014 |
| JP | 2018068192 | A | 5/2018 |

OTHER PUBLICATIONS

Wuts, P. (2014). Greene's protective groups in organic synthesis. Hoboken, N.J: John Wiley & Sons, Inc.

European Extended Search Report issued in European Patent Application 19755134.4 dated Mar. 3, 2021, 7 pages.

Japanese Office Action issued in Japanese Patent Application 2020-543305 dated Jan. 26, 2021, 10 pages.

Chinese First Office Action issued in Chinese Patent Application 201980013304.2 dated Apr. 8, 2021, 17 pages.

Chinese First Office Action issued in Chinese Patent Application 201810153233.3 dated Mar. 22, 2021, 7 pages.

Sung Ho Kim et al., "A Supramolecularly Assisted Transformation of Block-Copolymer Micelles into Nanotubes", Angew. Chem. Int. Ed., 2009, vol. 48, 5 pages.

Wu et al., "Biocompatible poly(ethylene glycol)-poly(γ-cholesterrol-l-glutamate) coplymers: synthesis, characterization, and in vitro studies)", Polymer Chemistry, 2012, vol. 50, 6 pages.

Ding et al., "Preparation of photo-cross-linked pH-responsive polypeptide nanogels as potential carriers for controlled drug delivery", Journal of Materials Chemistry, 2011, vol. 21, 9 pages.

Lee et al., "Synthesis of Poly(ethylene glycol)/Polypeptide/Poly(D, L-lactide) Copolymers and Their Nanoparticles", Journal of Polymer Science Part A: Polymer Chemistry, vol. 49, 2011, 7 pages.

Ding et al., "Preparation of Multifunctional Drug Carrier for Tumor-Specific Uptake and Enhanced Intracellular Delivery through the Conjugation of Weak Acid Labile Linker", Bioconjugate Chem, 2009, vol. 20, 8 pages.

Chinese Office Action dated Jun. 17, 2021 issued in counterpart Chinese application 201980013304.2, 13 pages.

\* cited by examiner

AMPHIPHILIC BLOCK COPOLYMER, PREPARATION METHOD THEREOF AND NANOMICELLE DRUG-LOADING SYSTEM

CROSS-REFERENCE TO RELATED APPLICATIONS

This application is a U.S. National Stage application of PCT/CN2019/074816, filed 12 Feb. 2019, which claims the benefit of priority of Chinese Application No. 201810153233.3 filed on 13 Feb. 2018, the entire disclosure of which is incorporated herein by reference in its entirety.

FIELD OF INVENTION

The present disclosure relates to a novel polyether-linker-polyester amphiphilic block copolymer, a preparation method thereof, and a stable nanomicelle drug delivery system formed from the copolymer and a poorly soluble drug.

BACKGROUND OF THE INVENTION

The delivery of poorly soluble drugs has always been a problem in the drug formulation technology. Only the dissolved drugs can be absorbed by the gastrointestinal mucosal epithelial cells. According to statistics, more than 40% of the drugs currently on the market are poorly soluble drugs. With the general use of combinatorial chemistry and high-throughput screening in the research and development of new drugs, the portion of poorly soluble drugs has been continuously growing. The less soluble the drugs are, the lower oral bioavailability they will have and thus they are unsuitable for an oral preparation. In order to better deliver the poorly soluble drugs, the conventional method is to develop them into injections through increasing the solubility by pH-adjustment, salt-formation, adding solubilizer or dissolving drugs in oil. But in practice, these approaches also introduce some deficiencies in the meantime of increasing the drug solubility.

Taxanes such as paclitaxel, docetaxel, cabazitaxel, larotaxel, etc., have been widely used as antitumor drugs because they can induce and promote tubulin polymerization, protect tubulin from disassembly, and stabilize microtubules. Spindle apparatus and spindle filaments thus fail to organize during mitosis, which in turn inhibits cell division and proliferation, and exerts antitumor effects. However, taxanes are very hydrophobic and can only be administered by injection with anhydrous ethanol as a solvent. A large amount of polyoxyethylene castor oil or Tween 80 is usually used as a solubilizer to promote the dissolution of the drugs in the injection preparation. These solubilizers will cause allergic reactions and hematological toxicity. On one hand, patients are required to receive desensitization before administration. On the other hand, the therapeutic dose is limited, and the best therapeutic effect of taxanes cannot be exerted. In addition, taxanes will precipitate due to the decreased solubility when this kind of injection is diluted in blood, resulting in inaccurate dosages. Thus the therapeutic effects will be unstable unless the injection process is in precise control. Therefore, a novel, safe and stable drug delivery system is in urgent need.

The amphiphilic block polymers will self-assemble into copolymer micelles with a spherical core-shell structure in aqueous solution. The hydrophobic segment forms the core while the hydrophilic segment forms the shell. The inner core works as a container for hydrophobic drugs through solubilizing the drug, which will increase the drug-loading capacity and reduce toxic side effects. The shell protects the drug from degradation and improves the stability. After the micelles are diluted in the blood, the spherical core-shell structure is slowly dissociated and then the drug is released, which achieves the sustained release effect. The particle size of micelles, usually between 10-200 nm, is much larger than that of small molecule drugs, which slows down the excretion by the kidney and the absorption by the reticuloendothelial system, extends the circulation in the body, and improves bioavailability. For anti-tumor drugs, passive targeting to tumor cells, which improves tumor-selective distribution, enhances drug efficacy and reduces system side effects, can also be achieved through enhanced permeability and retention effect (EPR effect).

Among amphiphilic block copolymers, PEG-PLA (Poly(ethylene glycol)-poly(lactic acid) copolymers) has been studied most extensively and intensively. Approved by FDA as a non-ionic water-soluble polymer, PEG (polyethylene glycol) possesses good biocompatibility, can be easily cleared from the body and show very low toxicity to the human body. Therefore it is prevalently used as pharmaceutical excipients. PLA (poly(lactic acid)/polylactide) is one of the first studied biodegradable polyester materials. The final degradation products in the body are carbon dioxide and water. Lactic acid, as the intermediate metabolite, is also a regular metabolite that will not accumulate in the body or cause toxic side effects. Thus PEG-PLA is a promising safe biomedical material.

Samyang Biopharmaceuticals in South Korea is the first company that applies PEG-PLA for drug delivery in clinic. A micelle formulated paclitaxel for injection (trade name Genexol-PM) from Samyang has been launched into market. When paclitaxel is loaded, the highest content ratio of drug to polymer is 20:100, and the micelles become unstable over a period of 24 h at room temperature after dissolution, indicating low drug-loading capacity and poor stability (Pharmaceutical Research 2007, 24, 1508-1516). When the interaction between drug and polymer is weak, the formed micelles will dissociate quickly after entering the bloodstream, causing drug leakage, which fails to achieve effective drug-loading and passive targeted delivery. It was disclosed in patent CN103772686B that when the termini of PEG-PLA chain was modified with t-butoxycarbonyl protected phenylalanine, it could appropriately improve the stability of micelles, but the drug/copolymer ratio was still only 20:100 at most. As described in patent CN105287377A, modification of PLA terminal with 9-Fluorenylmethyloxycarbonyl and t-butoxycarbonyl double-protected lysine also helped stabilizing micelles while the drug/copolymer ratio was yet only 20:90. Although natural amino acids were used in these modifications, the presence of protective groups may generate metabolic by-products that are harmful to the human body when the copolymer enters the blood.

On the other hand, during the synthesis of the copolymer, the catalysts for initiating lactide polymerization reported above are stannous octoate, and the reaction temperature is about 130° C. Tin reagents are highly toxic, so trace residues will have great influence on the biosafety of the polymers. Researches suggest that excessive tin in polymers will make a significant interference on the dynamic stability of the micellar system. In addition, when poly(lactic acid) is polymerized at high temperature, the back-biting of the chain (J. Am. Chem. Soc. 2016, 138, 8674-8677) is prone to broaden the molecular weight distribution of the copolymer, resulting in uncontrollable drug release. In practical production, it usually requires very elaborate purification methods to obtain qualified copolymers suitable for drug delivery. For instance, patent CN106349466A described a method by membrane ultrafiltration to obtain a copolymer with narrow molecular weight distribution. Patent CN103768013A disclosed a method of cation exchange resin to reduce tin residue in the mixture introduced by the catalyst. According to the method described in patent CN103980466B, active metal sodium and organic naphthalene were employed as catalysts in place of stannous octoate. However, sophisticated operative skills are necessary as the active metal is very sensitive to air and moisture. Besides, a large amount of explosive and narcotic ethyl ether are involved in the precipitation and purification of the copolymer in the prior art, which is very dangerous in the scale-up production.

In conclusion, the existing drug-loaded micelles based on PEG-PLA show various defects such as low drug-loading (the maximum drug/copolymer ratio is only 20:90), harsh synthetic conditions and complicated purification methods. In order to realize safe, effective and stable micellar drug delivery, it is necessary to modify the structure of the copolymer in a more systematical manner to improve the drug-loading capacity and micellar stability to a greater extent while ensuring safety. Meanwhile, there also exists a need to develop a method for copolymer synthesis with stable and environmental-friendly process and controllable quality.

CONTENT OF THE INVENTION

The object of the disclosure is to provide a novel polyether-linker-polyester amphiphilic block copolymer and its green preparation process, as well as a stable drug delivery system derived from self-assembly of the copolymer and poorly soluable drugs. The present disclosure solves the defects of the micelle drug-loading system in the prior art, such as low drug content, poor stability, harsh reaction condition and cumbersome purification procedure of the copolymer, and so on.

The present disclosure adopts linker containing aromatic ring for the modification of amphiphilic copolymer. The linker with aromatic ring could form strong conjugation interaction (π-π stackling) with poorly soluable drugs, especially those drugs containing aromatic rings. The strong interaction could stably lock the drug molecules within the hydrophobic core of the micelle. In this way, it not only enhances the stability of drug loaded micelle, but also greatly increases the drug-loading content of the copolymer.

Further, by introduction of linker, the present disclosure modifies biocompatible polyethylene glycol with small molecule fragment containing aromatic ring. The modified polyethylene glycol serves as initiator for polymerization of lactide by the catalysis of DBU, TBD or MTBD, forming an amphiphilic block copolymer with the structure of $R^1$-PEG-linker-PLA-$R^2$, wherein $R^1$, $R^2$ are each independently hydroxyl protecting group or hydrogen. When the linker is derived from natural amino acid, the in vivo metabolism of the amphiphilic copolymer will be safe to human body. In such, the copolymer would possess distinct biological safety. Still further, the reaction condition is mild when the polymerization of lactide is catalyzed by DBU. It is thus easier to get copolymer with narrow polydispersity. On the other hand, DBU is less harmful and could be easily removed by acidic wash, without the safety concerns on residual tin metal. During the purification of the copolymer, MTBE is used for precipitation instead of $Et_2O$, thus achieving greater security in large scale production. The novel preparation process of the amphiphilic copolymer provided by the present disclosure is mild in reaction condition, easy in quality control and suitable for industrial production.

As proved by experiments, in the nanomicelle drug-loading system provided by the present disclosure, the mass ratio of drug to amphiphilic copolymer in the lyophilized formulation could reach as high as 70:100. After reconstitution by physiological saline, it could form clear solution with slightly blue opalescene at room temperature. And the solution could be stable for as long as 72 hours at room temperature. The micelle drug delivery system could remarkably increase the solubility of poorly soluable drugs with aromatic substituent. It could largely improve the therapeutic efficacy towards tumors through enhanced permeability and retention effect (EPR effect), and reduce the toxicity and side effects of the drugs.

In the first aspect, the present disclosure provides an amphiphilic block copolymer. The amphiphilic block copolymer contains hydrophilic chain, hydrophobic chain, and a linker used to connect the hydrophilic chain and the hydrophobic chain. The linker can be small molecular fragment containing one or more structures or functional groups selected from the group consisting of aromatic ring, carbon-carbon double bond, carbon-carbon triple bond, conjugated double bond and conjugated triple bond.

In the preferred embodiment, the aromatic ring, carbon-carbon double bond, carbon-carbon triple bond, conjugated double bond and conjugated triple bond in the linker can be located in the linear chain of the amphiphilic block copolymer, or in the side chain of the amphiphilic block copolymer.

In the preferred embodiment, the structure of the linker can be $C_1$-$C_{30}$ small molecular fragment substituted by aromatic ring in the linear chain or the side chain.

In the preferred embodiment, the $C_1$-$C_{30}$ small molecular fragment substituted by aromatic ring in the linear chain or the side chain contains or does not contain heteroatom. The heteroatom can be one or more heteroatoms selected from the group consisting of oxygen, nitrogen, sulfur and phosphorus.

In the preferred embodiment, the structure of the linker can be $C_1$-$C_{30}$ small molecular fragment; The $C_1$-$C_{30}$ small molecular fragment can be substituted by aromatic ring;

The aromatic ring substituent can be $C_6$-$C_{20}$ aryl, $C_6$-$C_{20}$ aryl substituted by $R^a$, $C_2$-$C_{20}$ heteroaryl or $C_2$-$C_{20}$ heteroaryl substituted by $R^b$;

The number of $R^a$ can be one or more, when the number of $R^a$ is more than one, $R^a$ can be the same or different;

The number of $R^b$ can be one or more. When the number of $R^b$ is more than one, $R^b$ can be the same or different;

$R^a$ and $R^b$ are each independently $C_1$-$C_6$ alkyl, $C_1$-$C_6$ alkoxy, $C_4$-$C_6$ cycloalkyl, halide, hydroxyl or nitro group;

The heteroatom in $C_2$-$C_{20}$ heteroaryl or $C_2$-$C_{20}$ heteroaryl substituted by $R^b$ can be O, S or N. The number of the heteroatom can be one or more. When the number of the heteroatoms is more than one, the heteroatoms can be the same or different.

In the preferred embodiment, in the $C_6$-$C_{20}$ aryl or $C_6$-$C_{20}$ aryl substituted by $R^a$, the $C_6$-$C_{20}$ aryl is $C_6$-$C_{10}$ aryl, preferably phenyl or naphthyl.

In the preferred embodiment, in the $C_2$-$C_{20}$ heteroaryl or $C_2$-$C_{20}$ heteroaryl substituted by $R^b$, the $C_2$-$C_{20}$ heteroaryl is $C_2$-$C_{10}$ heteroaryl, preferably $C_3$-$C_8$ heteroaryl, e.g. indolyl or imidazolyl.

In the preferred embodiment, in $R^a$ or $R^b$, $C_1$-$C_6$ alkyl is preferably $C_1$-$C_3$ alkyl.

In the preferred embodiment, in $R^a$ or $R^b$, $C_1$-$C_6$ alkoxy is preferably $C_1$-$C_3$ alkoxy.

In the preferred embodiment, $R^a$ or $R^b$ are each independently $C_1$-$C_3$ alkyl, $C_1$-$C_3$ alkoxy, halide, hydroxyl or nitro group.

In the preferred embodiment, the aromatic ring can be $C_6$-$C_{10}$ aryl (e.g. phenyl or naphthyl), $R^a$ substituted $C_6$-$C_{10}$ aryl (e.g. phenyl or naphthyl), $C_2$-$C_{10}$ heteroaryl (e.g. indolyl or imidazolyl), or $R^b$ substituted $C_2$-$C_{10}$ heteroaryl (e.g. indolyl or imidazolyl), wherein $R^a$ or $R^b$ are each independently $C_1$-$C_3$ alkyl, $C_1$-$C_3$ alkoxy, halide, hydroxyl or nitro group.

In the preferred embodiment, the $C_1$-$C_{30}$ small molecular fragment can be $C_2$-$C_{10}$ small molecular fragment.

In the preferred embodiment, the $C_1$-$C_{30}$ small molecular fragment can be substituted by 1-3 (e.g. 1 or 2) aryl ring.

In the preferred embodiment, the $C_1$-$C_{30}$ small molecular fragment can contain or not contain heteroatom substitution. The heteroatom can be one or more heteroatoms selected from the group consisting of oxygen, nitrogen, sulfur or phosphorus. The number of the heteroatom can be one or more, and is preferably 1-4 (e.g. 1, 2, 3 or 4).

In the preferred embodiment, the structure of the linker can be selected from the group consisting of:

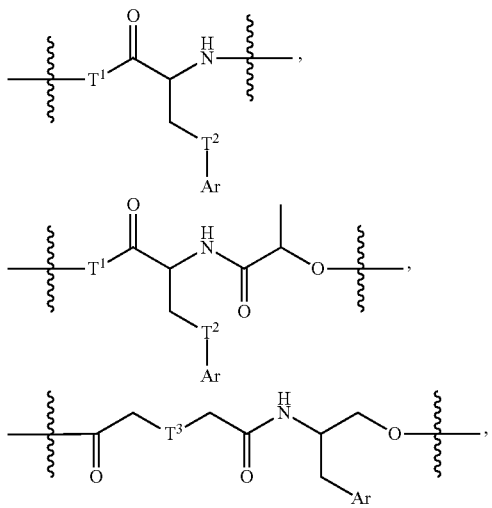

Wherein Ar is aryl ring, and the aryl ring is as defined as described before;

$T^1$ is single bond or

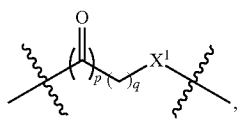

p is 0 or 1, q is 1, 2 or 3, X1 is —O—, —S—, or —NH—; $T^2$ is single bond or

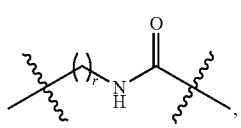

r is 0, 1, 2, 3, 4 or 5;

$T^2$ is single bond or

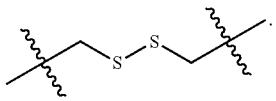 [SMILES: *CSSC*]

In the preferred embodiment, $T^1$ is single bond, $T^2$ is single bond.

In the preferred embodiment, $T^1$ is

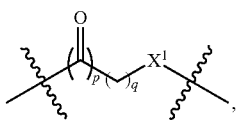

p is 0, q is 2, $X^1$ is —S— or —NH—, $T^2$ is single bond.

In the preferred embodiment, $T^1$ is

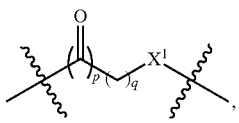

p is 1, q is 2, $X^1$ is —O—, $T^2$ is single bond.

In the preferred embodiment, the structure of the linker can be $C_1$-$C_{30}$ small molecular fragment derived from amino acids containing aromatic ring, from amino alcohol containing aromatic ring, or from peptide containing aromatic ring. The aromatic ring can also be from the protecting group of the hydroxy, thio, amino or carboxy functional group in the amino acid, amino alcohol or peptide. More preferably, the aromatic ring can be located in the side chain of the amino acid, amino alcohol or peptide, or be located in the protecting group of the hydroxy, thio, amino or carboxy functional group in the amino acid, amino alcohol or peptide.

In the preferred embodiment, in the amino acid with aromatic ring, the configuration of the amino acid can be R, S or racemic.

In the preferred embodiment, in the amino alcohol with aromatic ring, the configuration of the amino alcohol can be R, S or racemic.

In the preferred embodiment, in the amino acid with aromatic ring, the amino acid can be one or more amino acids selected from the group consisting of phenylalanine, histidine, tyrosine, tryptophan and 3-(2-naphthyl)-alanine.

In the preferred embodiment, in the peptide with aromatic ring, one or more building blocks can be derived from one or more amino acids selected from the group consisting of phenylalanine, histidine, tyrosine, tryptophan and 3-(2-naphthyl)-alanine.

In the preferred embodiment, the configuration of phenylalanine, histidine, tyrosine, tryptophan and 3-(2-naphthyl)-alanine can be R, S or racemic.

In the preferred embodiment, in the amino alcohol with aromatic ring, the amino alcohol can be one or more amino alcohols selected from the group consisting of phenylalaninol, histidinol, tyrosinol, tryptosol and 3-(2-naphthyl)-alaninol; Phenylalaninol, histidinol, tyrosinol, tryptosol and 3-(2-naphthyl)-alaninol can be reduced from phenylalanine, histidine, tyrosine, tryptophan and 3-(2-naphthyl)-alanine, respectively.

In the preferred embodiment, the configuration of phenylalaninol, histidinol, tyrosinol, tryptosol or 3-(2-naphthyl)-alaninol can be R, S or racemic.

In the preferred embodiment, in the $C_1$-$C_{30}$ small molecular fragment containing aromatic ring substitution in the linear chain or side chain, the aromatic ring from amino acids containing aromatic ring, from amino alcohol containing aromatic ring, or from peptide containing aromatic ring. The aromatic ring can also be from the protecting group of the hydroxy, thio, amino or carboxy functional group in the amino acid, amino alcohol or peptide. More preferably, the aromatic ring can be located in the side chain of the amino acid, amino alcohol or peptide, or be located in the protecting group of the hydroxy, thio, amino or carboxy functional group in the amino acid, amino alcohol or peptide.

In the preferred embodiment, the hydrophilic chain can be polyethylene glycol chain segment or mono-protected polyethylene glycol chain segment with the number-average molecular weight ranging from 400 to 20000. The mono-protected polyethylene glycol chain segment is preferably polyethylene glycol chain segment with protection at the terminal hydroxyl group.

In the preferred embodiment, the hydrophobic chain segment can be one chain segment selected from the group consisting of polylactide chain segment, mono-protected polylactide chain segment, polyglycolide chain segment, mono-protected polyglycolide chain segment, poly (lactide-co-glycolide) chain segment, mono-protected poly (lactide-co-glycolide) chain segment, polycaprolactone chain segment, mono-protected polycaprolactone chain segment, polycarbonate chain segment, mono-protected polycarbonate chain segment, polydioxanone chain segment and mono-protected polydioxanone, with the number-average molecular weight ranging from 400 to 20000. The mono-protected polylactide chain segment, mono-protected polyglycolide chain segment, mono-protected poly (lactide-co-glycolide) chain segment, mono-protected polycaprolactone chain segment, mono-protected polycarbonate chain segment, or mono-protected polydioxanone are each independently preferably chain segment with protection at the terminal hydroxyl group.

In the preferred embodiment, the hydrophobic chain segment can be polylactide chain segment or mono-protected polylactide chain segment with number-average molecular weight ranging from 400 to 20000. The mono-protected polylactide chain segment is preferably polylactide chain segment with protection at the terminal hydroxyl group.

In the preferred embodiment, the amphiphilic block copolymer can have the structure of: $R^1$—PEG-linker-PLA-$R^2$, wherein $R^1$ and $R^2$ are each independently hydroxyl protecting group or hydrogen;

PEG is polyethylene glycol chain segment with number-average molecular weight ranging from 400-20000; PLA is polylactide chain segment with number-average molecular weight ranging from 400 to 20000; The ratio of polyethylene glycol chain segment and polylactide chain segment in number-average molecular weight can be 1:(0.5-2).

In another aspect, the present disclosure also provides a preparation method for the amphiphilic block copolymer mentioned above.

The object of the present disclosure is implemented by the following technical solutions:

A method for the preparation of the above-mentioned amphiphilic block copolymer, comprising, 1) modification of polyethylene glycol or mono-protected polyethylene glycol (number average molecular weight ranging from 400 to 20000) with linker;

2) with catalyst in organic solvent, using the product from step 1) as initiator for polymerization of DL-lactide, L-lactide, D-lactide, glycolide, mixture of DL-lactide and glycolide with different ratio, mixture of L-lactide and glycolide with different ratio, mixture of D-lactide and glycolide with different ratio, caprolactone, mixture of bisphenol A and diphenyl carbonate, or p-dioxanone;

3) optionally, protecting the terminal hydroxyl group of the polymer from step 2).

In the preferred embodiment, the preparation method of the amphiphilic block copolymer can comprise the following steps:

1) modification of polyethylene glycol or mono-protected polyethylene glycol (number-average molecular weight ranging from 400 to 20000) with small molecular fragment containing aryl substitution to prepare $R^1$-PEG-linker;

2) dissolving $R^1$-PEG-linker and DL-lactide, or L-lactide, or D-lactide in organic solvent, adding catalyst to promote polymerization to prepare $R^1$-PEG-linker-PLA;

3) optionally, protecting the terminal hydroxyl group of PLA in $R^1$-PEG-linker-PLA to prepare $R^1$-PEG-linker-PLA-$R^2$.

Wherein the number-average molecular weight of the obtained PLA ranges from 400 to 20000;

$R^1$ and $R^2$ are each independently hydroxyl protecting group or hydrogen.

In the preferred embodiment, in the preparation method of the amphiphilic block copolymer, the catalyst from step 2) can be catalysts selected from the group consisting of 1,8-Diazabicyclo[5.4.0]undec-7-ene (DBU), stannous octoate, magnesium 2-ethylhexanoate, 1,5,7-Triazabicyclo[4.4.0]dec-5-ene (TBD) and 7-Methyl-1,5,7-triazabicyclo[4.4.0] dec-5-ene (MTBD). And the catalyst is preferably 1,8-Diazabicyclo[5.4.0]undec-7-ene (DBU) and/or stannous octoate.

In the preferred embodiment, in the preparation method of the amphiphilic block copolymer, step 2) is followed with an additional step, comprising purification of the obtained product (e.g. $R^1$-PEG-linker-PLA mentioned above).

In the preferred embodiment, in the preparation method of the amphiphilic block copolymer, step 3) is followed with an additional step, comprising purification of the obtained product (e.g. $R^1$-PEG-linker-PLA-$R^2$ mentioned above).

In the preferred embodiment, in the preparation method of the amphiphilic block copolymer, step 2) is followed with an additional step, comprising purification of the obtained product (e.g. $R^1$-PEG-linker-PLA mentioned above), and step 3) is followed with an additional step, comprising purification of the obtained product (e.g. $R^1$-PEG-linker-PLA-$R^2$ mentioned above).

In the preferred embodiment, the amphiphilic block copolymer can have the following structure:

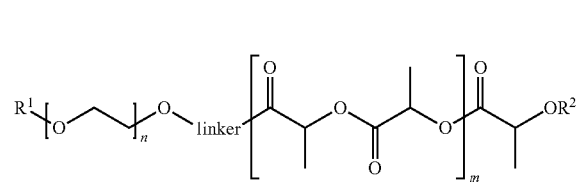

I wherein linker, $R^1$ and $R^2$ are as defined as described before;

n=8-455 (e.g. n=8, 9, 400 or 455); m=3-160 (e.g. m=3, 140 or 160).

In the preferred embodiment, n=9-455; m=3-140.

In the preferred embodiment, n=8-440; m=3-160.

In the preferred embodiment, the amphiphilic block copolymer can be selected from the group consisting of:

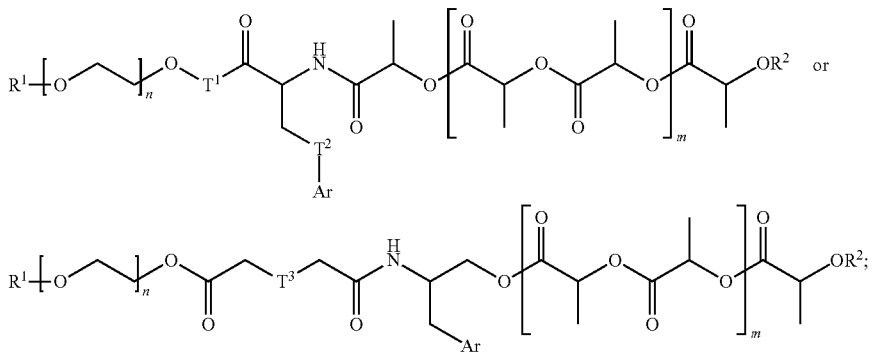

wherein $R^1$, $R^2$, n and m are as defined as described before;
Ar is aromatic ring as defined as described before;
$T^1$ is single bond or

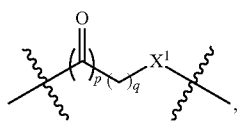

p is 0 or 1, q is 1, 2 or 3 (e.g. 2), $X^1$ can be —O—, —S— or —NH—;
$T^2$ is single bond or

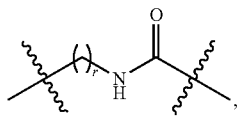

r is 0, 1, 2, 3, 4 or 5 (e.g. 3).
$T^3$ is single bond or

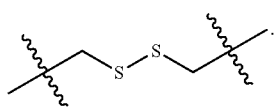 [SMILES: *CSSC*]

In the preferred embodiment, $T^1$ is single bond, $T^2$ is single bond.

In the preferred embodiment, $T^1$ is

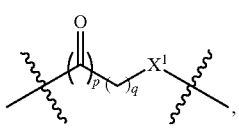

p is 0, q is 2, $X^1$ can be —S— or —NH—, $T^2$ is single bond.

In the preferred embodiment, $T^1$ is

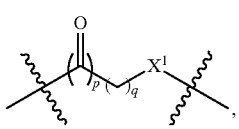

p is 1, q is 2, $X^1$ is —O—, $T^2$ is single bond.

In the preferred embodiment, the amphiphilic copolymer can have the following structure:

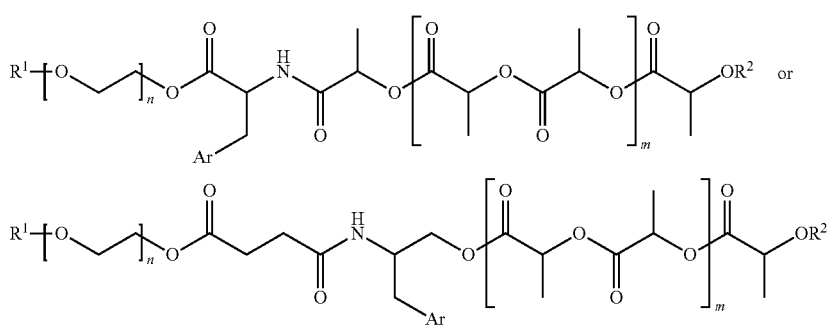

wherein $R^1$, $R^2$, and Ar are as defined as described before; n=8-440; m=3-160.
The amphiphilic block copolymer is preferably selected from the group consisting of:
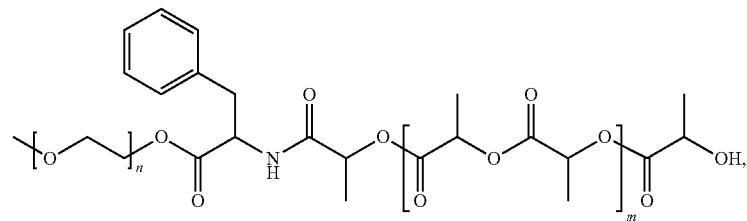
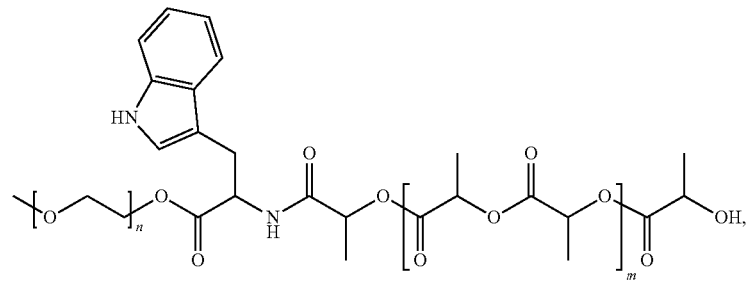
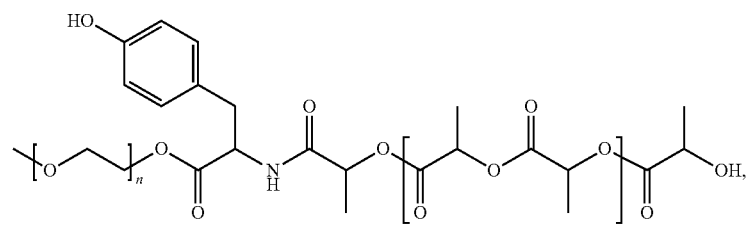
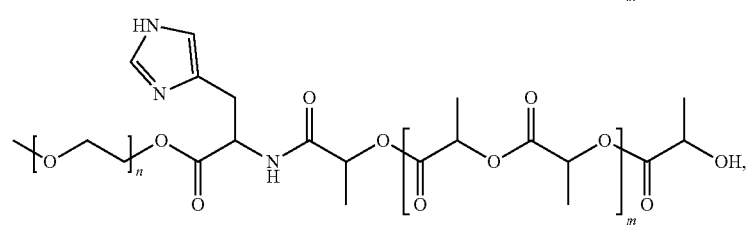
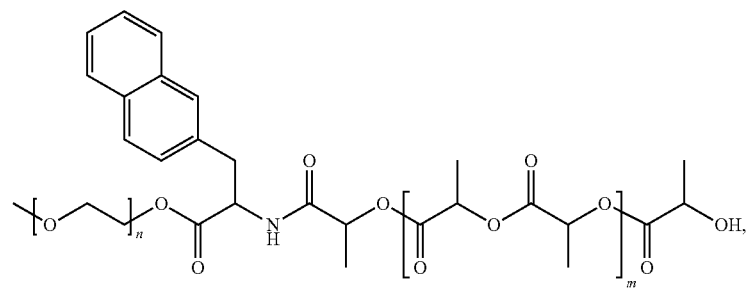
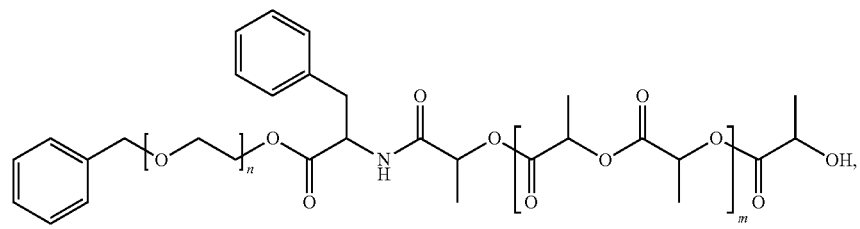

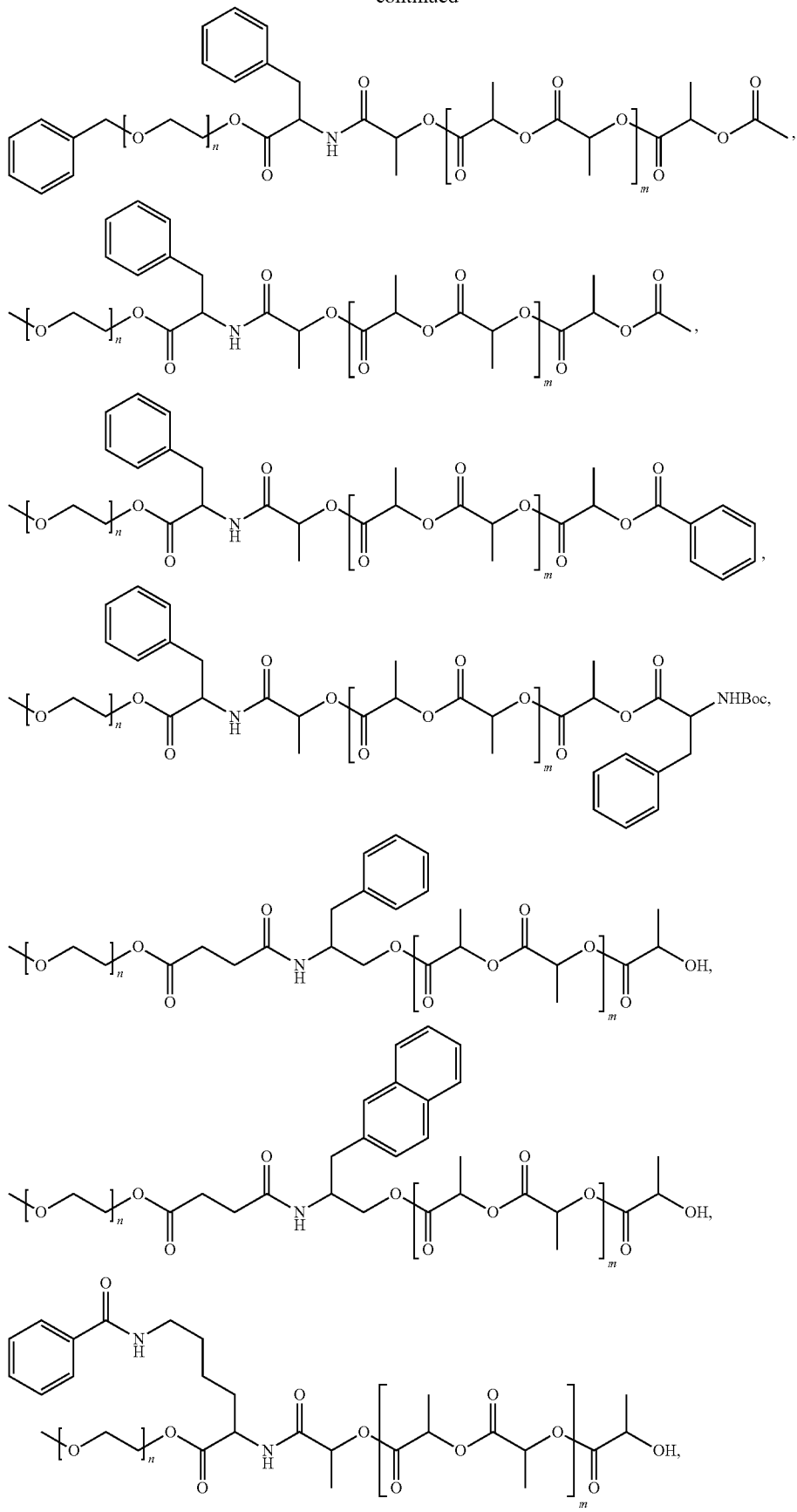

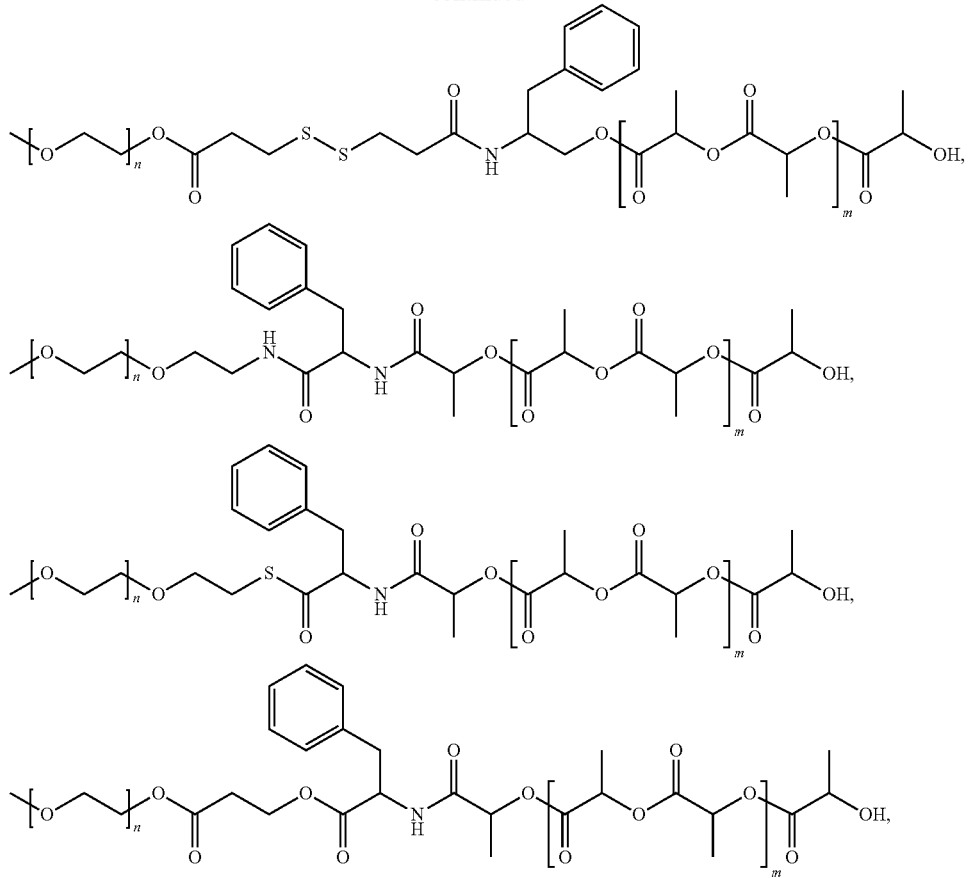
wherein n and m are as defined as described before;
In the preferred embodiment, the amphiphilic block copolymer can be selected from the group consisting of:
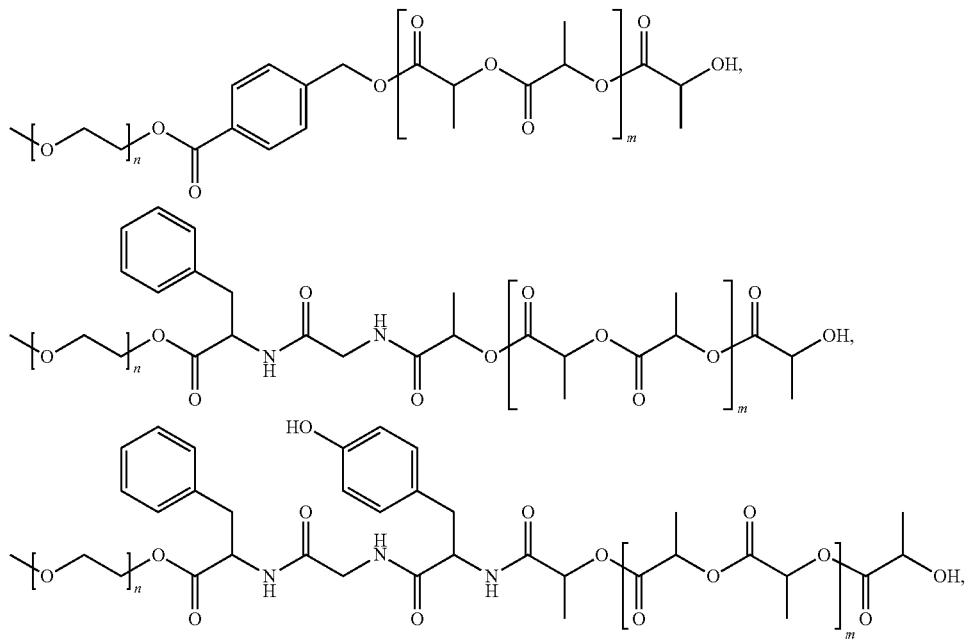
wherein n and m are as defined as described before;

The present disclosure also provides a polymer of formula II,

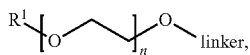  II wherein linker and n are as defined in the polymer of formula I;
$R^1$ is hydroxyl protecting group or hydrogen.

In the preferred embodiment, the polymer of formula II can be selected from the group consisting of:

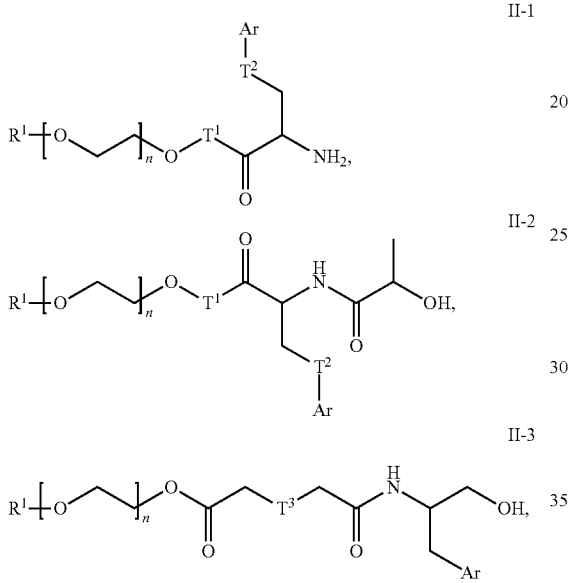

wherein $R^1$, n, $T^1$, $T^2$, $T^3$ and Ar are as defined as described before;

In the preferred embodiment, the polymer of formula II can be selected from the group consisting of:

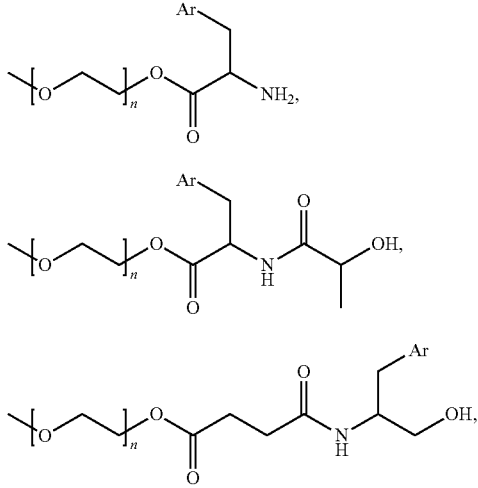

wherein n and Ar are as defined as described before.

The present disclosure also provides a method for the preparation of polymer of formula II, comprising modification of polymer of formula III with small molecular fragment,

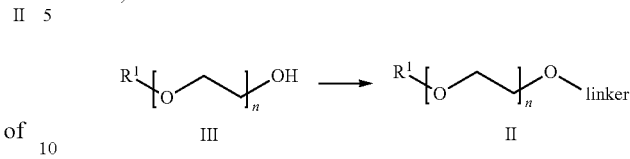

wherein linker and n are as defined in the polymer of formula I;
$R^1$ is hydroxyl protecting group or hydrogen.

The present disclosure also provides a method for the preparation of a polymer of formula II-1, comprising deprotection of the polymer of formula III-1,

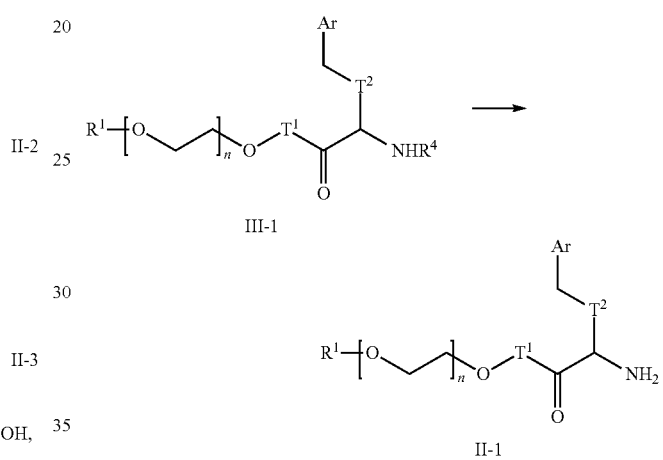

Wherein $R^1$, n, $T^1$, $T^2$ and Ar are as defined as mention before; $R^4$ is amino protecting group.

The present disclosure also provides a method for the preparation of a polymer of formula II-2, comprising deprotection of the polymer of formula III-2,

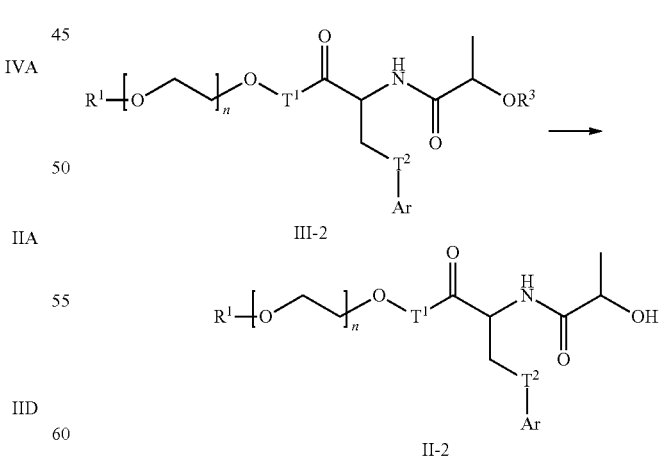

wherein $R^1$, n, $T^1$, $T^2$ and Ar are as defined as mentioned before; $R^3$ is hydroxyl protecting group.

In the preferred embodiment, the polymer of formula III-2 is prepared by the condensation reaction of the polymer of formula II-1 and the compound of formula VI-1,

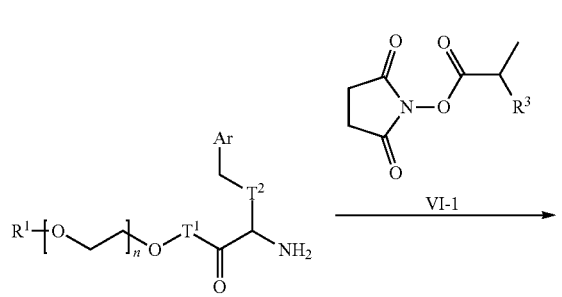

II-1

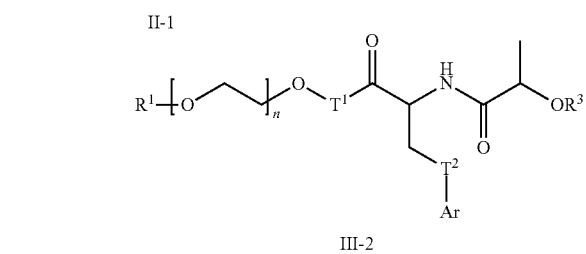

III-2 wherein R¹, n, T¹, T², Ar and R³ are as defined as described before.

The present disclosure also provides a method for the preparation of a polymer of formula II-3, comprising condensation reaction between the polymer of formula III-3 and the compound of formula IV-D,

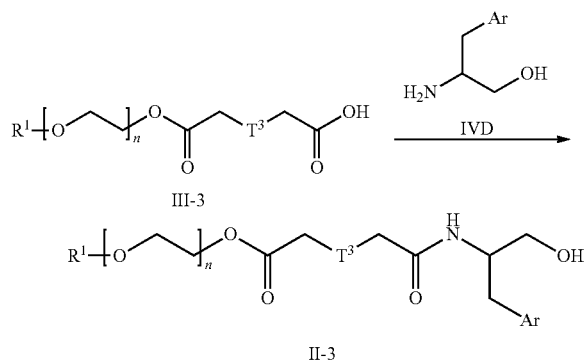

Wherein R¹, n, T³ and Ar are as defined as described before.

The present disclosure also provides a method for the preparation of an amphiphilic block copolymer of formula I, comprising the following steps:

1) in the presence of catalyst, initiating a polymerization reaction of lactide by the polymer of formula II as described before to prepare the copolymer of formula IA; wherein the lactide is DL-lactide, L-lactide or D-lactide; The catalyst is as defined as described before;

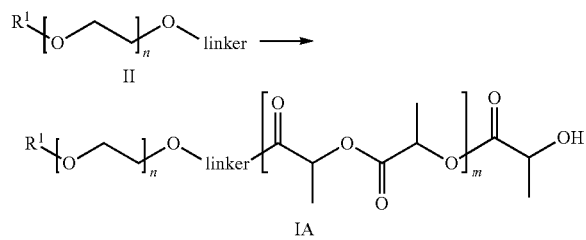

2) conducting a hydroxyl protection reaction of the copolymer of formula IA to prepare the amphiphilic block copolymer of formula I;

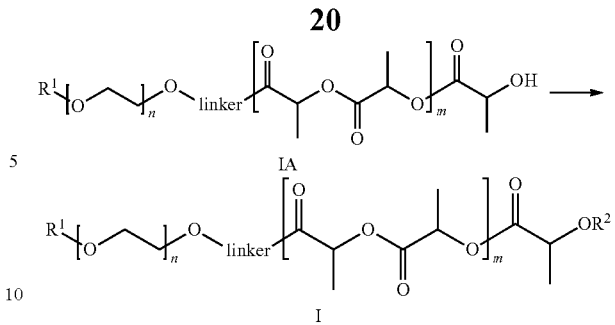

wherein linker, R¹, R², m and n are as defined as described before; when R² is hydrogen, it is not necessary to perform step 2).

In the preferred embodiment, in the method for the preparation of the amphiphilic block copolymer of formula I, the polymer of formula II is prepared by the following method, comprising modification of the polymer of formula III with small molecular fragment;

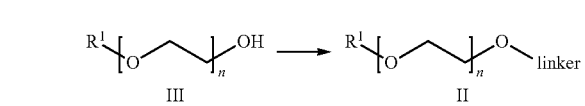

wherein linker, R¹ and n are as defined as described before.

In the preferred embodiment, the present disclosure provides a method for the preparation of an amphiphilic block copolymer of formula I,

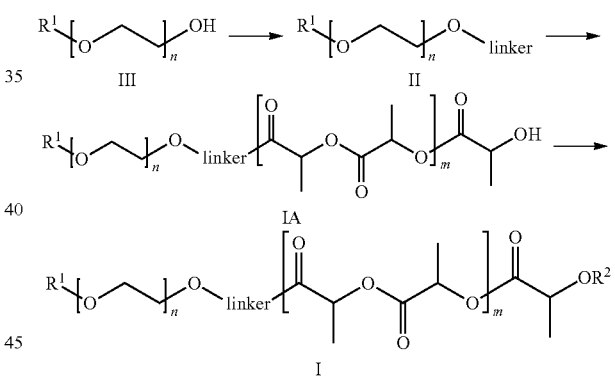

wherein the structure of the linker is small molecular fragment containing one or more functional groups selected from the group consisting of aromatic ring, carbon-carbon double bond, carbon-carbon triple bond, conjugated double bond and conjugated triple bond.

R¹ and R² are each independently hydroxyl protecting group or hydrogen;

n=8-440; m=3-160.

Specifically, comprising the following steps:

1) modification of the polymer of formula III with small molecular fragment to prepare the polymer of formula II;

2) in the presence of catalyst, initiating the polymerization of lactide by the polymer of formula II to prepare the copolymer of formula IA;

3) optionally, conducting hydroxyl protection reaction of the copolymer of formula IA to prepare the amphiphilic block copolymer or formula I.

The present disclosure also provides a method for the preparation of an amphiphilic block copolymer of formula IC',

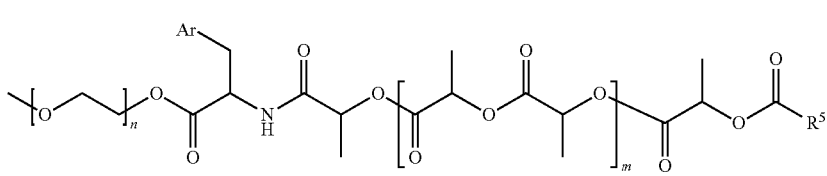

IC'

Wherein n, m and Ar are as defined as described before;

$R^5$ is substituted or unsubstituted $C_1$-$C_{10}$ alkyl, $C_6$-$C_{20}$ aryl or amino acid residue.

In the preferred embodiment, $R^5$ can be substituted or unsubstituted $C_1$-$C_6$ alkyl (e.g. methyl), $C_6$-$C_8$ aryl (e.g. phenyl), or amino acid residue

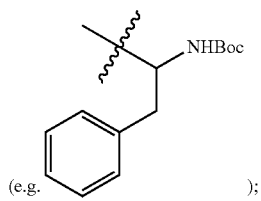 [SMILES: *C(Cc1ccccc1)NC(=O)OC(C)(C)C]

(e.g. );

$R^5$ is preferably unsubstituted $C_1$-$C_3$ alkyl (e.g. methyl), phenyl, or amino acid residue

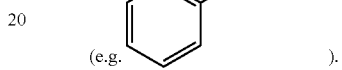

(e.g. ).

The present disclosure also provides a method for the preparation of the amphiphilic block copolymer of formula IC', comprising conducting acyl protecting reaction of the amphiphilic copolymer of formula IB,

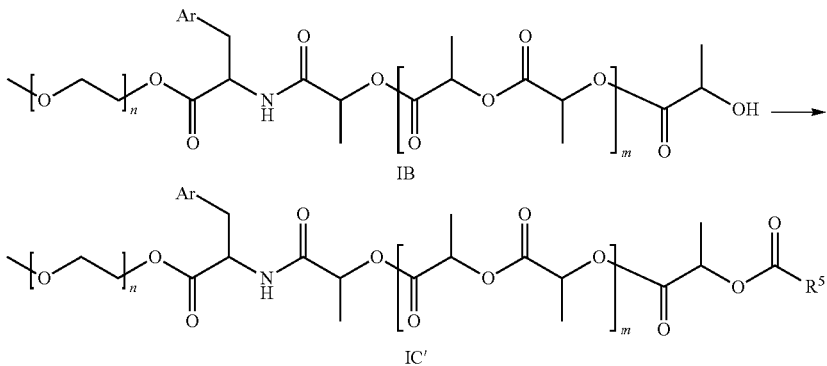

Wherein Ar, $R^5$, n and m are as defined as described before.

In the preferred embodiment, the present disclosure also provides an amphiphilic block copolymer of formula IC,

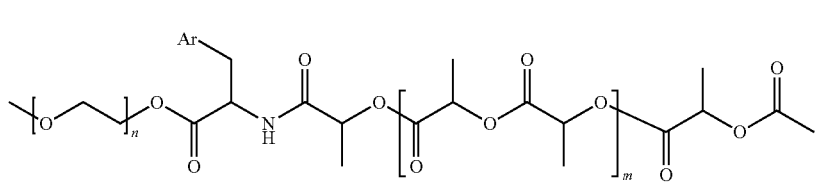

IC wherein n=8-440; m=3-160;

Ar can be substituted or unsubstituted aryl.

In the preferred embodiment, the present disclosure also provides a method for the preparation of the amphiphilic block copolymer of formula IC, comprising conducting acetyl protecting reaction of the amphiphilic block copolymer of formula IB,

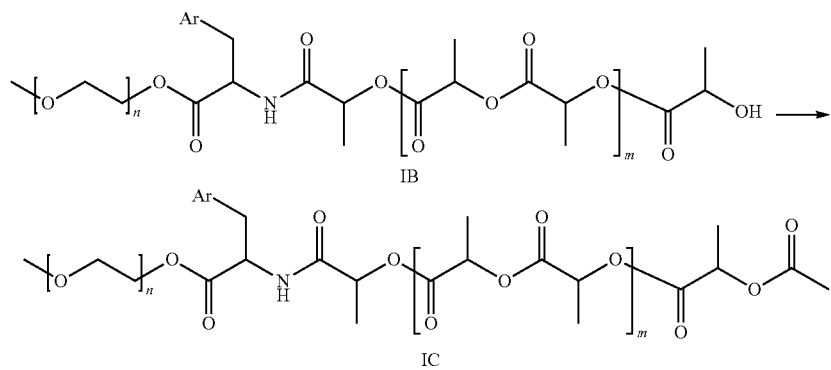

wherein n=8-440; m=3-160;

Ar can be substituted or unsubstituted aryl.

The present disclosure also provides an amphiphilic block copolymer of formula IB,

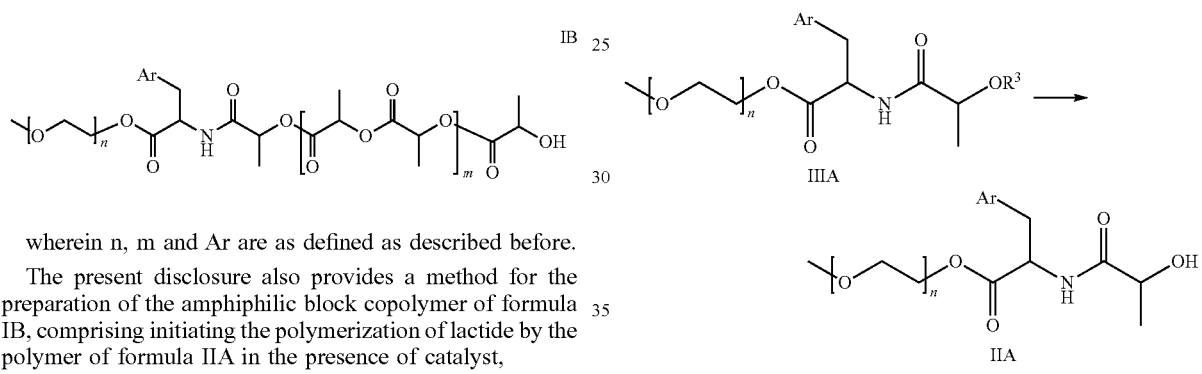

wherein n, m and Ar are as defined as described before.

The present disclosure also provides a method for the preparation of the amphiphilic block copolymer of formula IB, comprising initiating the polymerization of lactide by the polymer of formula IIA in the presence of catalyst,

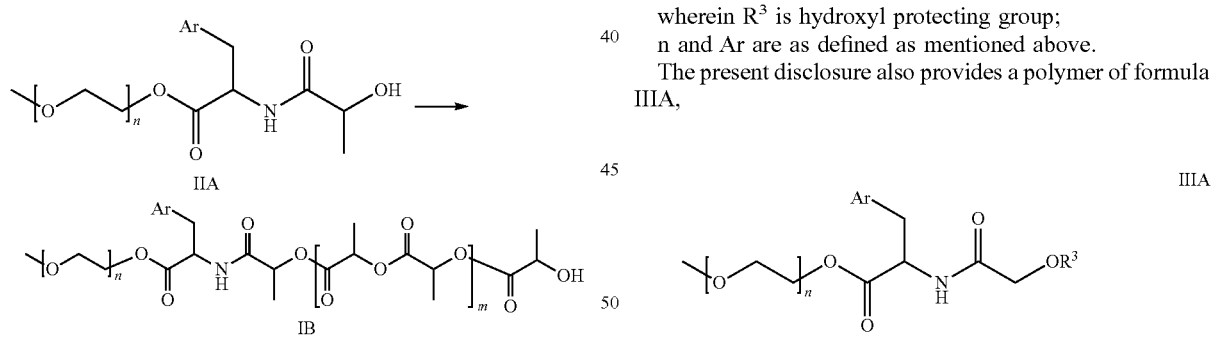

wherein n, m and Ar are as defined as described before.

The present disclosure also provides a polymer of formula IIA,

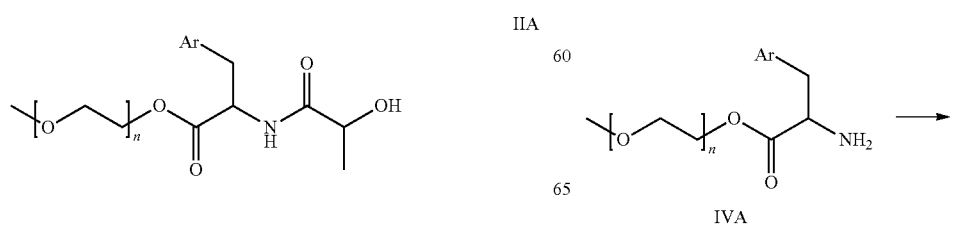

wherein n and Ar are as defined as described before.

The present disclosure also provides a method for the preparation of polymer of formula IIA, comprising conducting hydrolysis of the protecting group of the polymer of formula IIIA, wherein $R^3$ is hydroxyl protecting group;

n and Ar are as defined as mentioned above.

The present disclosure also provides a polymer of formula IIIA,

Wherein $R^3$, n and Ar are as defined as described before.

The present disclosure also provides a method for the preparation of polymer of formula IIIA, comprising conducting condensation reaction of the polymer of formula IVA, -continued

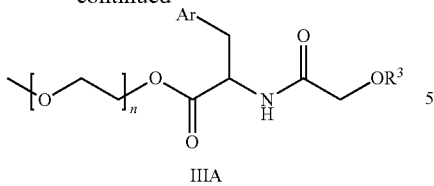

IIIA wherein $R^3$, n and Ar are as defined as described before.

The present disclosure also provide a polymer of formula IVA,

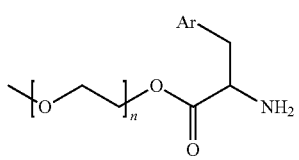

IVA wherein n and Ar are as defined as described before.

The present disclosure also provides a method for the preparation of the polymer of formula IVA, comprising conducting the hydrolysis of the amino protecting group of the polymer of formula VA,

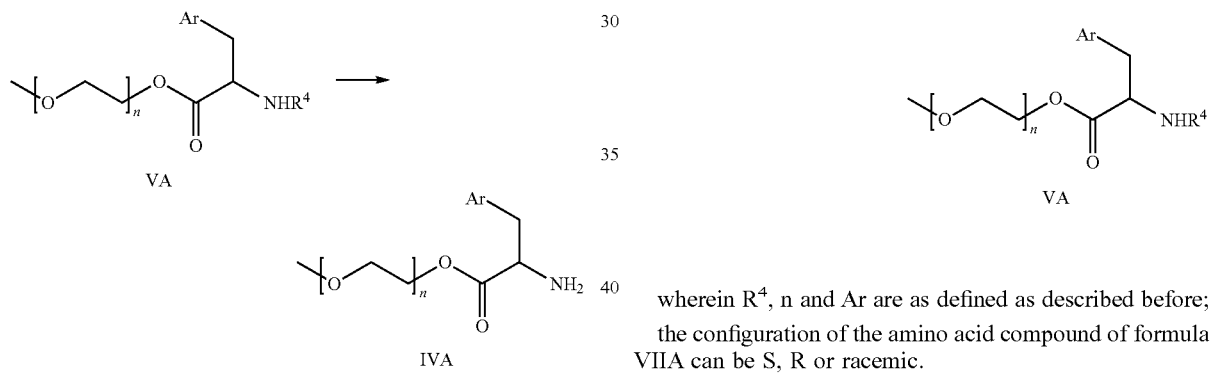

wherein $R^4$ is amino protecting group;
n and Ar are defined as described before.

The present disclosure also provides a polymer of formula VA,

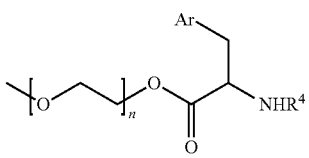

VA wherein $R^4$, n and Ar are as defined as described before.

The present disclosure also provides a method for the preparation of the polymer of formula VA, comprising conducting condensation reaction between the polymer of formula VIA and the compound of formula VIIA,

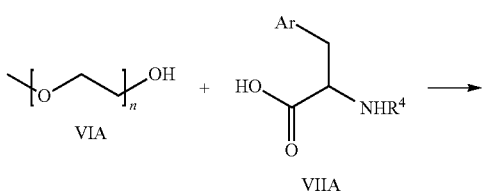

wherein $R^4$, n and Ar are as defined as described before;
the configuration of the amino acid compound of formula VIIA can be S, R or racemic.

In the preferred embodiment, the present disclosure provides a method for the preparation of the amphiphilic block copolymer of formula IB or IC',

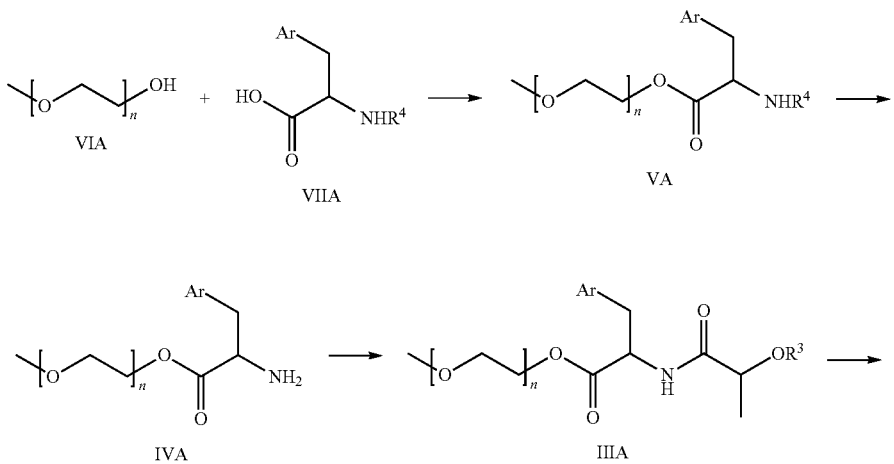

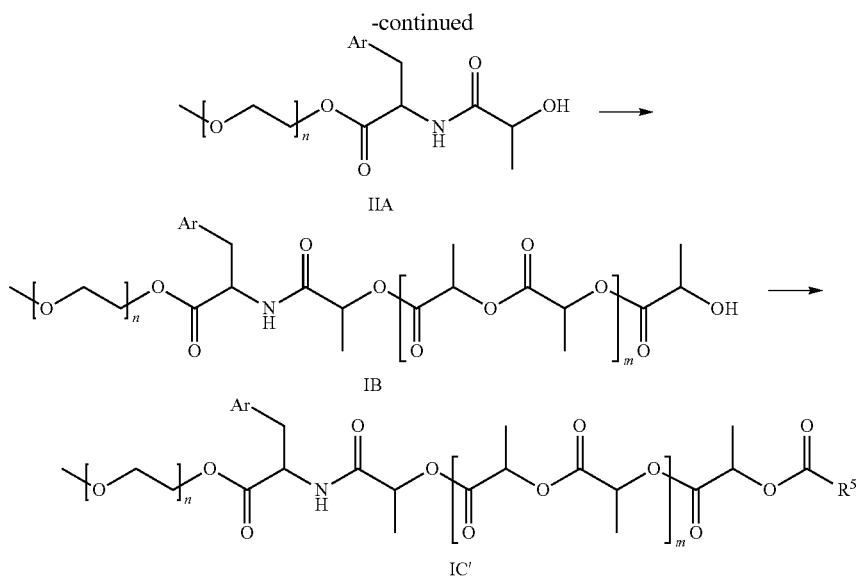

wherein n, m, $R^3$, $R^4$, $R^5$ and Ar are as defined as described before.

The configuration of the amino acid compound of formula VIIA can be S, R or racemic.

Specifically, comprising the following steps:

1) conducting condensation reaction between the polymer of formula VIA and the compound of formula VIIA to prepare the polymer of formula VA;

2) conducting deprotection reaction of the polymer of formula VA to prepare the polymer of formula IVA;

3) conducting condensation reaction of the polymer of formula IVA to prepare the polymer of formula IIIA, 4) conducting deprotection reaction of the polymer of formula IIIA to prepare the polymer of formula IIA;

5) initiating the polymerization of lactide by the polymer of formula IIA in the presence of catalyst to prepare the amphiphilic block copolymer of formula IB;

6) conducting esterification reaction of the amphiphilic block copolymer of formula IB in the present of acylation reagent to prepare the amphiphilic block copolymer of formula IC'.

In the preferred embodiment, in the preparation method for the amphiphilic block copolymer of formula IB or IC', step 5) is followed with an additional step comprising: purification of the amphiphilic block copolymer of formula IB.

The present disclosure also provides a preparation method for the amphiphilic block copolymer of formula IB, comprising initiating polymerization of lactide by the polymer of formula IVA in the presence of catalyst,

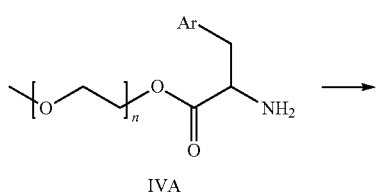

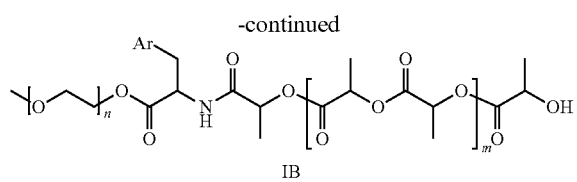

wherein n, m and Ar are as defined as described before.

In another preferred embodiment, the present disclosure also provides a method for the preparation of the amphiphilic block copolymer of formula IB,

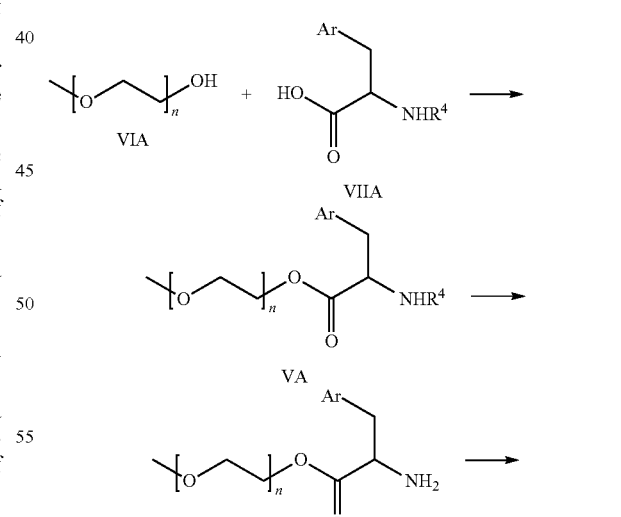

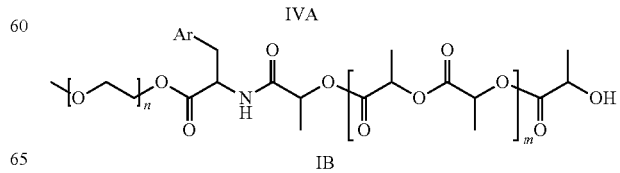

wherein R⁴, n, m and Ar are as defined as described before.

The configuration of the amino acid compound of formula VIIA can be S, R or racemic.

Specifically, comprising the following steps:
1) conducting condensation reaction between the polymer of formula VIA and the compound of formula VIIA to prepare the polymer of formula VA;
2) conducting deprotection reaction of the polymer of formula VA to prepare the polymer of formula IVA;
3) initiating polymerization of lactide by the polymer of formula IVA in the presence of catalyst to prepare the amphiphilic block copolymer of formula I.B;
4) optionally, conducting purification of the amphiphilic block copolymer.

The present disclosure also provides an amphiphilic block copolymer of formula ID,

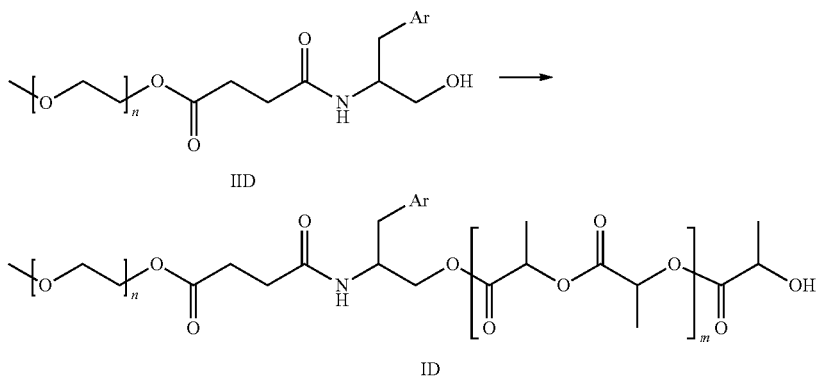

wherein n, m and Ar are as defined as described before.

The present disclosure also provides a method for the preparation of the amphiphilic block copolymer of formula ID, comprising initiating polymerization of lactide by the polymer of formula IID in the presence of catalyst,

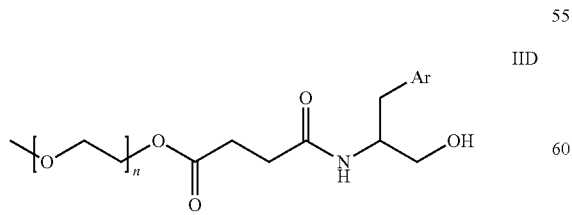

wherein n, m and Ar are as defined as described before.

The present disclosure also provides a polymer of formula IID,

IID

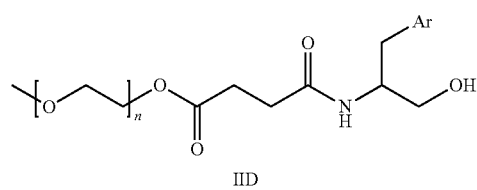

wherein n and Ar are as defined as described before.

The present disclosure also provides a method for preparation of the polymer of formula IID, comprising conducting condensation reaction between the polymer of formula IIID and the compound of formula IVD,

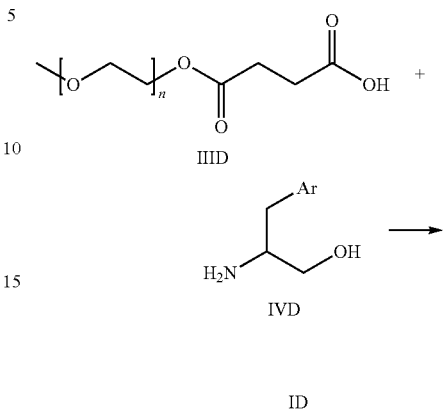

-continued

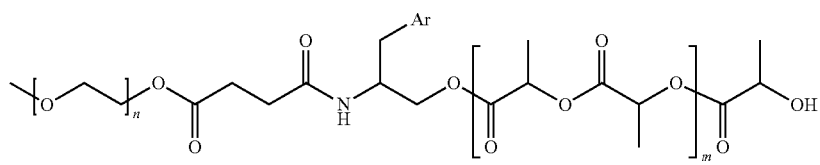

wherein n and Ar are as defined as described before;
the configuration of the amino alcohol compound of formula IVD can be S, R or racemic.

The present disclosure also provides a polymer of formula IIID,

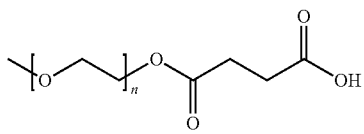

wherein n is as defined as described before.

The present disclosure also provides a method for the preparation of the polymer of formula IIID, comprising conducting ring opening reaction of the compound of formula VID by the polymer of formula VIA,

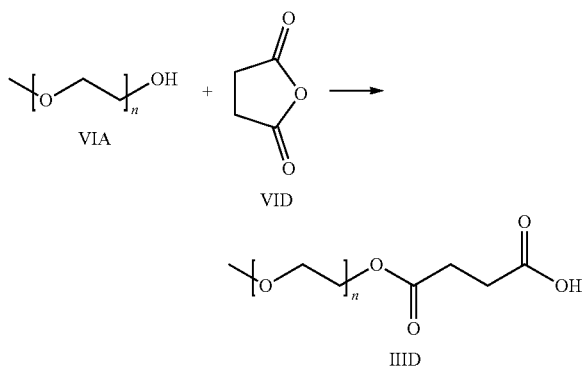

wherein n is as defined as described before.

In another preferred embodiment, the present disclosure provides a method for the preparation of the amphiphilic block copolymer of formula ID,

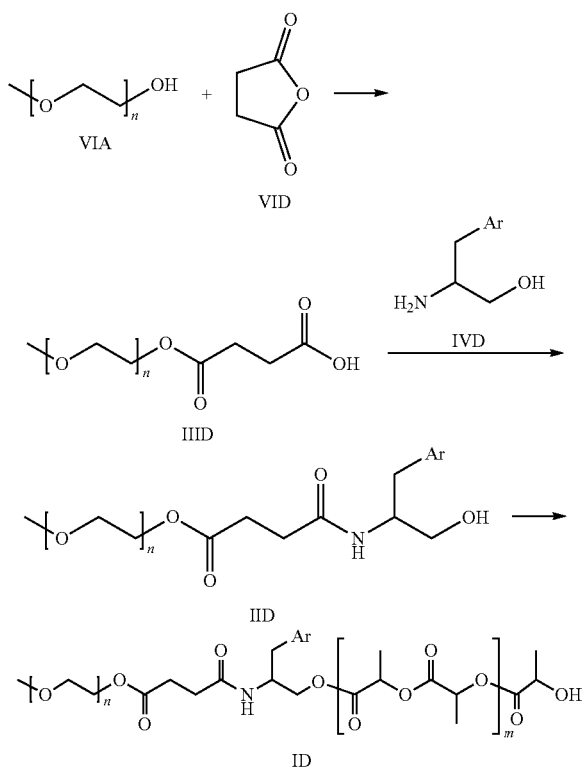

wherein n, m and Ar are as defined as described before.

The configuration of the amino alcohol compound of formula IVD can be S, R or racemic.

Specifically, comprising the following steps:

1) conducting ring opening reaction of the compound of formula VID by the polymer of formula VIA to prepare the polymer of formula IIID;

2) conducting condensation reaction between the polymer of formula IIID and the compound of formula IVD to prepare the polymer of formula IIID;

3) initiating polymerization of lactide by the polymer of formula IID in the presence of catalyst to prepare the amphiphilic block copolymer of formula ID;

In the preferred embodiment, step 3) is following by a step comprising: purification of the amphiphilic block copolymer of formula ID.

In the preferred embodiment of the present disclosure, the catalyst for initiating polymerization of lactide can be one or more catalysts selected from the group consisting of 1,8-Diazabicyclo[5.4.0]undec-7-ene (DBU), stannous octoate, Magnesium 2-ethylhexanoate, 1,5,7-Triazabicyclo[4.4.0]dec-5-ene (TBD) and 7-Methyl-1,5,7-triazabicyclo[4.4.0]dec-5-ene (MTBD). And the catalyst is preferably 1,8-Diazabicyclo[5.4.0]undec-7-ene (DBU) and/or stannous octoate.

The present disclosure also provides a method for the purification of the amphiphilic block copolymer, comprising:

dissolving the amphiphilic block copolymer crude prepared according to the present disclosure in organic solvent, sequentially washing with diluted acid (e.g. diluted hydrochloric acid) and saturated sodium chloride, concentration, adding precipitant to precipitate the polymer, filtration to get pure amphiphilic block copolymer in solid form.

In the preferred embodiment, in the purification method of the amphiphilic block copolymer, the organic solvent can be dichloromethane.

In the preferred embodiment, the precipitant can be methyl t-butyl ether (MTBE).

In the preferred embodiment, the crude amphiphilic block copolymer from the present disclosure is dissolved in dichloromethane, sequentially washed with diluted hydrochloric acid and saturated sodium chloride, dried with anhydrous sodium sulfate, filtered and concentrated to remain a small amount of dichloromethane, or concentrated to dryness and dissolved again with a small amount of dichloromethane; the dichloromethane solution is treated with MTBE to induce precipitation of the polymer; the solid is filtered and dried under vacuum to get pure amphiphilic block copolymer in solid form.

The object of the present disclosure is also to provide a nanomicelle drug-loading system by the amphiphilic block copolymer mentioned above and poorly soluable drug.

The technical solution provided by the present invention is as follows:

a nanomicelle drug-loading system, comprising at least the amphiphilic block copolymer from the present disclosure and drug.

In the preferred embodiment, the drug is preferably poorly soluable drug.

In the preferred embodiment, the weight ratio of the drug and the amphiphilic block copolymer is (0.5-100):100, preferably (1-70):100.

In the preferred embodiment, the poorly soluable drug is at least one drug selected from the group consisting of paclitaxel, docetaxel, cabazitaxel, 7-epipaclitaxel, t-acetylpaclitaxel, 10-deacetylpaclitaxel, 10-deacetyl-7-epipaclitaxel, 7-xylosylpaclitaxel, 10-des acetyl-7-glutarylpaclitaxel, 7-N,N-dimethylglycylpaclitaxel, 7-L-alanylpaclitaxel, larotaxel, doxorubicin, epirubicin, SN-38, irinotecan, topotecan, cyclophosphamide, ifosfamide, estramustine, mitoxantrone, amsacrine, cisplatin, carboplatin, oxaliplatin, etoposide, teniposide, vinblastine, vincristine, vinorelbine, vindesine, maytansine, harringtonine, homoharringtonine, mitomycin, bleomycin, daunorubicin, idarubicin, doxorubicin, epirubicin, gemcitabine, capecitabine, fludarabine, cladribine, bortezomib, carfilzomib, ixazomib, carmustine, fluorouracil, cytarabine, cyclosporin A, sirolimus, temsirolimus, everolimus, eribulin, trabectedin, fulvestrant, letrozole, temozolomide, raloxifene, tamoxifen, lenalidomide, ixabepilone, methotrexate, pemetrexed, enzalutamide, abiraterone, bendamustine, curcumin, resveratrol, indomethacin, huperzine A, acyclovir, allopurinol, amiodarone, azathioprine, benazepril, calcitriol, candesartan, eprosartan, carbidopa/levodopa, clarithromycin, clozapine, desmopressin acetate, diclofenac, enalapril, famotidine, felodipine, fenofibrate, fentanyl, fexofenadine, fosinopril, furosemide, glibenclamide, scopolamine, imipramine, itraconazole, levothyroxine, atorvastatin, lovastatin, meclizine, megestrol, thiopurine, metolazone, mometasone, nabumetone, omeprazole, paroxetine, propafenone, quinapril, simvastatin, sirolimus, tacrolimus, tizanidine, risperidone, olanzapine, ziprasidone, rivastigmine, naloxone, naltrexone, sirolimus, tacrolimus, carmustine, progesterone, estrogen, estradiol, levonorgestrel, norethisterone, ixabepilone, epothilone, rapamycin, plicamycin, vancomycin, amphotericin B, etoposide, doxycycline, itraconazole, fluconazole, voriconazole, posaconazole, ketoconazole, testosterone, progesterone, triamcinolone, dexamethasone, tenoxicam, piroxicam, ibuprofen, caspofungin, micafungin, olaparib, butylphthalide, combretastatin, GW6471, COX-II inhibitor, aromatase inhibitor, peptide drugs and a mixture thereof.

In the preferred embodiment, the nanomicelle drug-loading system also contain pharmaceutically acceptable pharmaceutical ingredient.

In the preferred embodiment, the weight percent of the pharmaceutical ingredient in the whole system can be 0-99.9%, preferably 0-50%.

In the preferred embodiment, the pharmaceutical ingredient can be freeze-dried excipient.

In the preferred embodiment, the freeze-dried excipient can be one or more excipients selected from the group consisting of lactose, mannose, sucrose, trehalose, fructose, glucose, sodium alginate and gelatin.

In the preferred embodiment, the weight percent of the freeze-dried excipient in the whole system can be 0-99.9%, preferably 0-50%.

In the preferred embodiment, the nanomicelle drug-loading system at least comprises the amphiphilic block copolymer from the present disclosure, poorly soluable drug and pharmaceutically acceptable pharmaceutical ingredient.

The nanomicelle drug-loading system from the present disclosure can be used in the preparation of a drug in treating cancer, inflammation, diabetes, central nervous disease, cardiovascular disease, mental disease, etc, preferably cancer and central nervous disease.

The effective treatment amount in the present disclosure refers to the amount that the nanomicelle drug-loading system mentioned above could effectively treat the diseases (specifically cancer and central nervous disease, etc.).

The nanomicelle drug-loading system in the present disclosure can be administrated by oral, inhalation or injection, preferably injection, generally in the form of lyophilized powder formulation. In addition, the dosage can be determined by those skilled in the art according to the dosage of the prior anti-tumor drug, and adjusted according to the individual situation.

The present disclosure also provides a method for the preparation of the nanomicelle drug-loading system, comprising dialysis, solvent evaporation or thin-film rehydration, preferably thin-film rehydration.

The present disclosure also provides a method for the preparation of the nanomicelle drug-loading system by the amphiphilic block copolymer and the drug containing aromatic ring, comprising dialysis, solvent evaporation or thin-film rehydration, preferably thin-film rehydration.

General procedure of thin-film rehydration comprises: dissolving the polymer and drug in a certain ratio in organic solvent, evaporating the organic solvent, redissolving with injection water at 20° C.-80° C. to prepare drug-loading micelle solution. Optionally, adding freeze-dry excipient to the micelle solution, filter sterilization and freeze-drying to prepare micelle lyophilized powder.

FIG. 21 shows the core-shell structural diagram of the micelle without any modification (the stretched shell representing PEG, the core part representing PLA, the spot representing poorly soluable drug). When the aromatic functional group was located at the termini of PEG and PLA chain, as described in patent CN103772686B and CN105287377A, all of the aromatic functional groups are crowded in the most central of the core part, so that the region for drug dissolution through mutual interaction is very limited. It is thus not suitable for significantly increasing the drug loading capacity compared to the unmodified PEG-PLA. While in the case of the present disclosure, the aromatic functional group is located between PEG and PLA chain segment. Practically, it can be homogeneously distributed in interaction part of the core-shell structure. Hence, the surface area for effective interaction with poorly soluable drug, especially drug with aromatic ring, could be distinctly increased, as shown in FIG. 23. The drug-loading capacity and micellar stability was simultaneously improved.

Compared to the prior art, the present disclosure possesses the following advantages:

1) The present disclosure adopts small molecular fragment, especially amino acid, amino alcohol or peptide equipped with aromatic ring, as a linker to connect the polyethylene glycol and the polylactide. In one aspect, the introduction of aromatic ring improved the hydrophobic property of the obtained amphiphilic block copolymer. In another aspect, during the process of self-assembly to micelle, the enhanced conjugation interaction between the aromatic rings both from the amphiphic block copolymer and the poorly soluable drug could significantly increase the drug-loading capacity, and improve the stability of the micellar drug. The mass ratio of drug to copolymer in the lyophilized micellar powder can reach as high as 70:100. After redissolved by physiological saline, the solution could be stable for more than 72 h. As shown in FIG. 15, when the drug loading content (mass ratio of drug to copolymer) is 20:100 by the unmodified PEG-PLA (copolymer from Samyang, Korea), a visual opacitas appeared in 6 h after redissolution. An obvious particle precipitation appeared in 24 h. When the amphiphilic block copolymer modified with aromatic ring in the present disclosure is used for loading paclitaxel in the ratio of 20:100 (mass ratio of drug to copolymer), it is still clear in 72 h after redissolution. As indicated in FIG. 16, when the drug loading content was 20:100, 30:100, 40:100 or even 60:100, the micellar solution of the amphiphilic block copolymer from the present disclosure and the paclitaxel was still clear in 72 h;

2) The linker in the present disclosure is small molecular fragment with aromatic ring. When the linker is derived from natural amino acid fragment with aromatic ring, the metabolism in vivo is safe. Thus the copolymer is a safe biological material;

3) The catalyst, especially DBU in the present disclosure, can initiate the polymerization of lactide at room temperature without rigid moisture or oxygen free operation. The molecular weight distribution of the obtained copolymer is narrow. The catalyst could be easily removed by acidic wash. The purification is simple and without the the safety concerns on residual tin metal;

4) The present disclosure adopts safer precipitant than ethyl ether during the purification of the copolymer. Methyl t-butyl ether is more suitable for large scale production.

5) As proved by experiments, the lyophilized formulation from the nanomicelle drug-loading system by the amphiphilic block copolymer in the present disclosure could be quickly redissolved and dispersed into a clear solution with blue opalescene. The solution is stable for more than 72 h without obvious drug precipitation. It could exert EPR effect and show superior pharmacokinetic and pharmacodynamic property after injection in vivo, therefore is potential for industrial application.

Unless otherwise indicated, the terms used herein have the following meanings:

"Aryl" refers to a 6- to 14-membered all-carbon monocyclic ring or polycyclic fused ring (a fused ring system means that each ring in the system shares an adjacent pair of carbon atoms with another ring in the system) with a conjugated π-electron system, preferably 6- to 10-membered, more preferably phenyl group and naphthyl group, most preferably phenyl group. The aryl group could be substituted or unsubstituted. When the aryl group is substituted, the substituent(s) is preferably one or more groups independently selected from the group consisting of alkyl, alkenyl, alkynyl, alkoxy, alkylthio, alkylamino, halogen, mercapto, hydroxyl, nitro, cyano, cycloalkyl, heterocycloalkyl, aryl, heteroaryl, cycloalkyoxy, heterocycloalkoxy, cycloalkylthio, and heterocycloalkylthio, more preferably hydroxyl.

The hydroxyl, thio and carboxy protecting groups used in the present disclosure are appropriate hydroxyl, thio and carboxy protecting groups known in the art. See the hydroxyl protecting groups described in "Protective Groups in Organic Synthesis", 5Th Ed. T. W. Greene & P. G. M. Wuts. For example, the hydroxyl protecting groups are preferably C1-10 alkyl or substituted alkyl groups, e.g. methyl, tert-butyl, allyl, benzyl, methoxymethyl, ethoxyethyl, 2-tetrahydropyranyl (THP), etc. The hydroxyl protecting groups can also be (C1-10 alkyl or aryl)acyl groups, e.g. formyl, acetyl, benzoyl, etc. The hydroxyl protecting groups can also be (C1-6 alkyl or C6-10 aryl)sulfonyl groups or (C1-6 alkoxy or C6-10 aryloxy)carbonyl groups. The hydroxyl protecting groups can also be (C1-10 alkyl or aryl)3silyl group, e.g. triethylsilyl, triisopropylsilyl, tert-butyldimethylsilyl, tert-butyldiphenylsilyl, etc.

The amino protecting groups used in the present disclosure are appropriate amino protecting groups known in the art. See the amino protecting groups described in "Protective Groups in Organic Synthesis", 5Th Ed. T. W. Greene & P. G. M. Wuts. For example, the amino protecting groups are preferably acyl or alkyloxycarbonyl, e.g. formyl, acetyl, tertbutoxycarbonyl, benzyloxycarbonyl, fluorenylmethyloxycarbonyl, trichloroethoxycarbonyl, etc.

The poorly soluable drugs used in the present disclosure are those drugs with solubility less than 1 g/1000 mL in aqueous media according to Chinese Pharmacopoeia.

In the present disclosure, number-average molecular weight is calculated based on H-NMR.

DETAILED DESCRIPTION OF THE PREFERRED EMBODIMENTS

Figure 1:
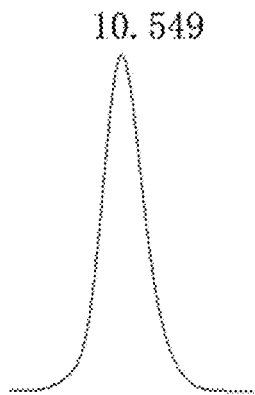
FIG. 1 is the gel permeation chromatograph of the copolymer of formula Ia, PDI=1.07.
Figure 2:
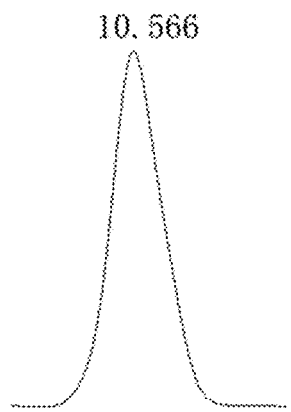
FIG. 2 is the gel permeation chromatograph of the copolymer of formula Ib, PDI=1.05.
Figure 3:
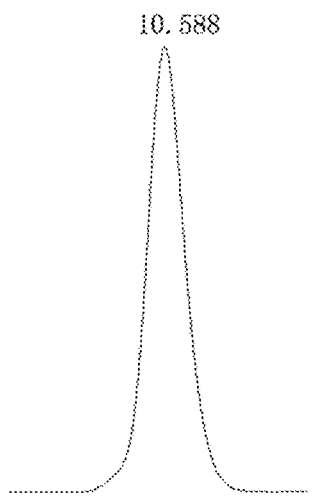
FIG. 3 is the gel permeation chromatograph of the copolymer of formula Ic, PDI=1.07.
Figure 4:
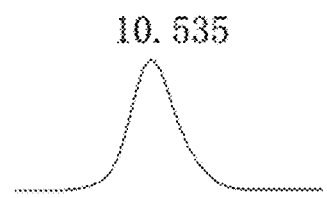
FIG. 4 is the gel permeation chromatograph of the copolymer of formula Id, PDI=1.07.
Figure 5:
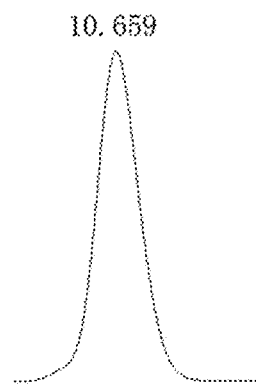
FIG. 5 is the gel permeation chromatograph of the copolymer of formula Ie, PDI=1.06.
Figure 6:
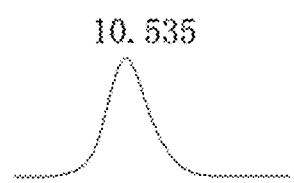
FIG. 6 is the gel permeation chromatograph of the copolymer of formula Il, PDI=1.07.
Figure 7:
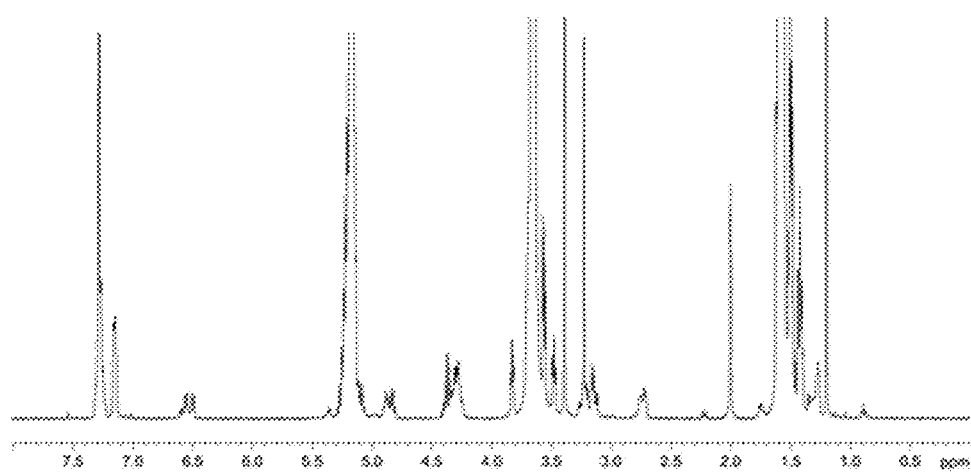
FIG. 7 is the H-NMR spectrum of the copolymer of formula Ia.
Figure 8:
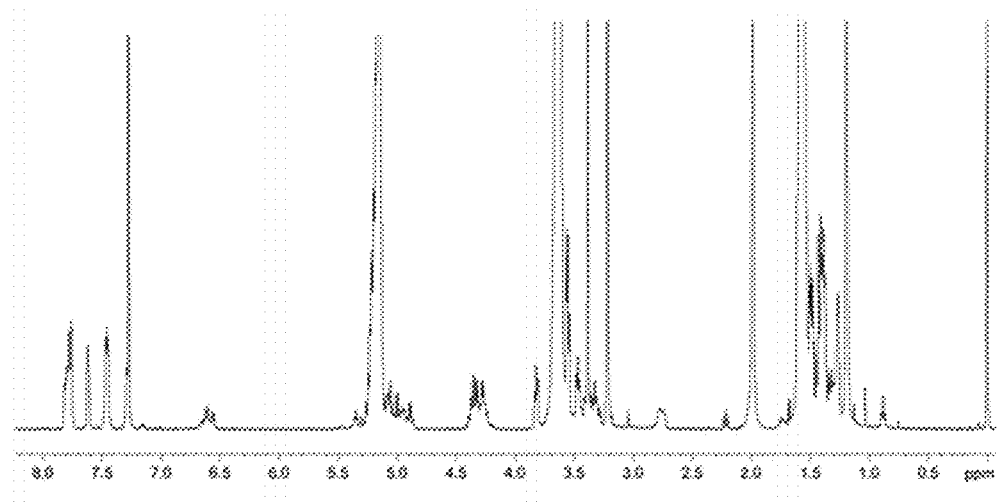
FIG. 8 is the H-NMR spectrum of the copolymer of formula Ib.
Figure 9:
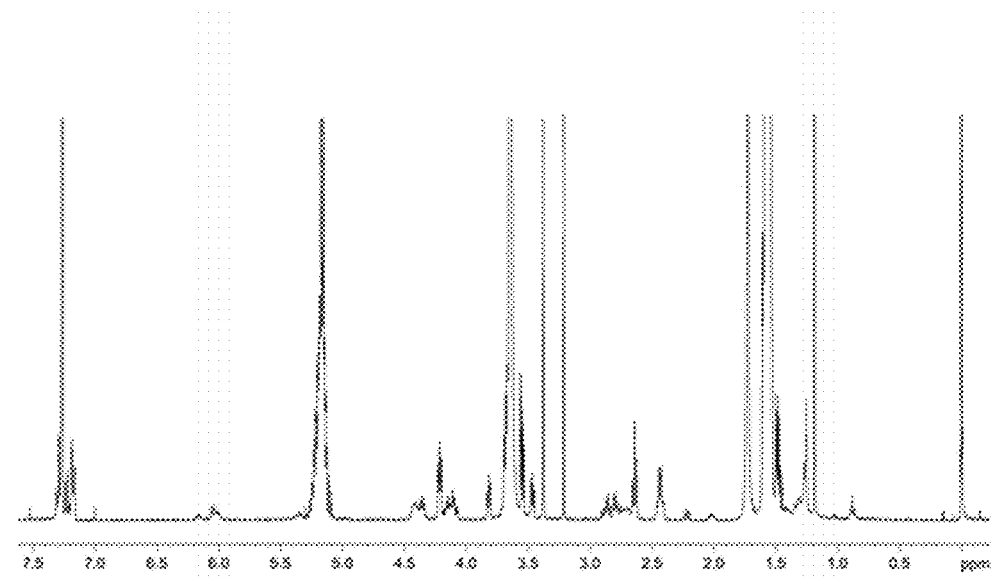
FIG. 9 is the H-NMR spectrum of the copolymer of formula Ic.
Figure 10:
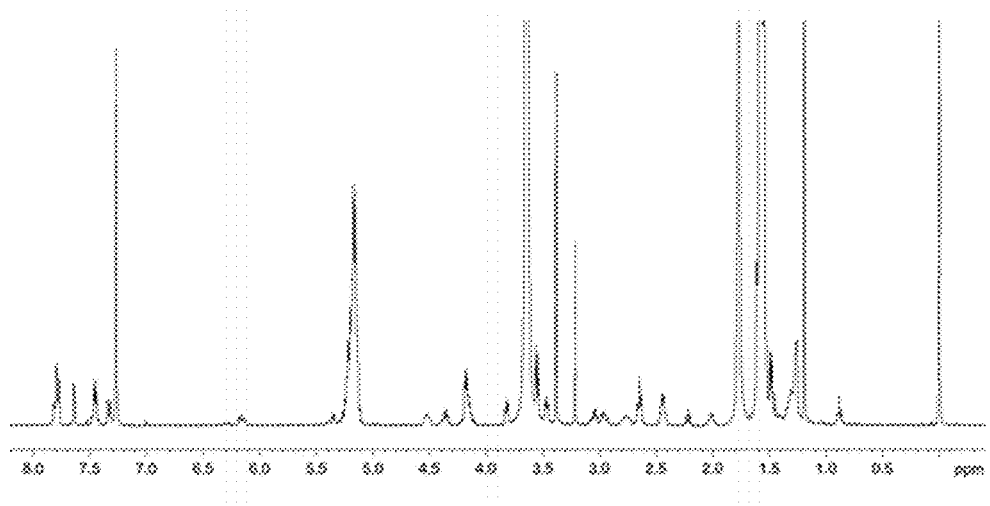
FIG. 10 is the H-NMR spectrum of the copolymer of formula Id.
Figure 11:
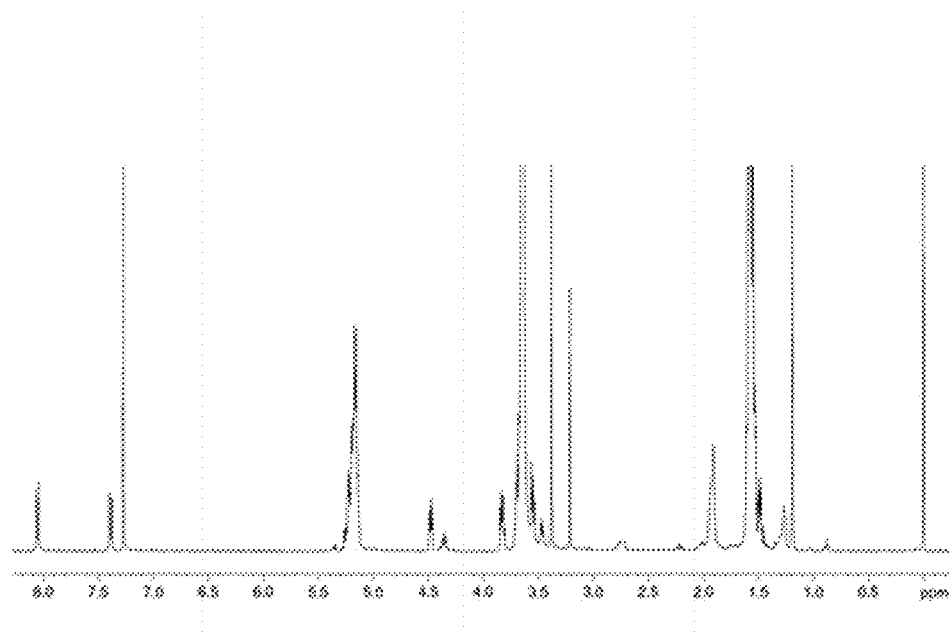
FIG. 11 is the H-NMR spectrum of the copolymer of formula Ie.
Figure 12:
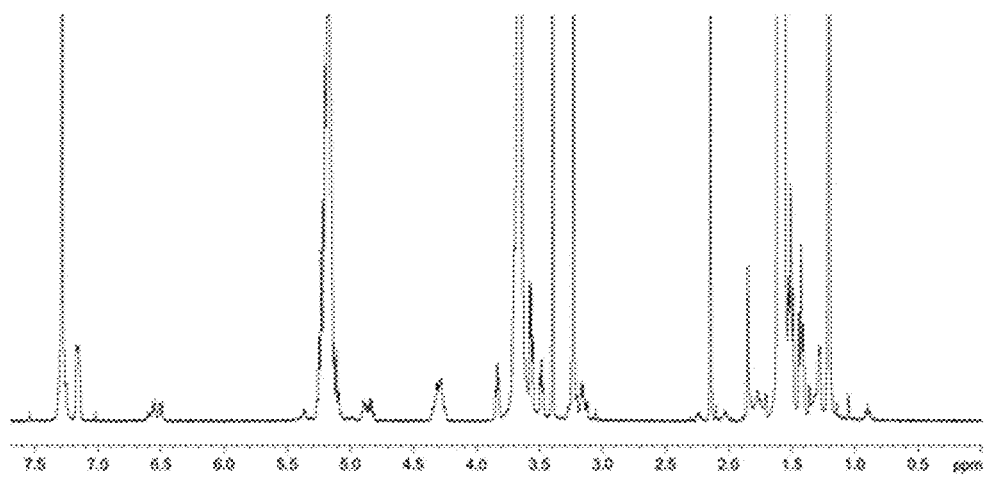
FIG. 12 is the H-NMR spectrum of the copolymer of formula Il.

The present disclosure provides specific embodiments, but the present disclosure is not limited thereto. Those concrete conditions and experimental methods which are not defined in the specific embodiments can follow conventional methods and conditions, or can be selected from commercial instructions.

Example 1: Preparation of the Compound of Formula VIa 4.48 g lactic acid was added to the flask, and dissolved by 100 mL dichloromethane. After imidazole (16.2 g) was added and dissolved, TBSCl (18 g) was then added under stirring. The reaction was stirred at room temperature for 16 h and quenched by water. Workup and concentration to get crude intermediate. The crude intermediate was dissolved by 200 mL MeOH and 100 mL K2CO3 aqueous solution. The resulting solution was stirred at room ambient temperature for 3 h, extracted by EtOAc, concentrated to get the second crude intermediate. The second crude intermediate was dissolved by 50 mL dichloromethane. After addition of DCC (7 g) and NHS (5.4 g), the reaction was stirred at room temperature for 16 h. After filtration, the filtrate was concentrated to get a solid-liquid mixture crude. Purification by silica gel chromatography yielded 8.6 g compound of formula VIa.

$^1$H NMR (400 MHz, Chloroform-d) δ 4.64 (q, J=6.8 Hz, 1H), 2.95-2.71 (m, 4H), 1.63-1.49 (m, 3H), 0.90 (s, 9H), 0.12 (d, J=4.8 Hz, 6H).

Example 2: Preparation of the Compound of Formula Va 10 g polyethylene glycol monomethyl ether (number-average molecular weight of 2000) was added to the flask, dissolved by 50 mL dichloromethane. Under stirring, Boc-protected L-phenylalanine (3.6 g), EDCI (5.71 g) and DMAP (1.52 g) were sequentially added to the mixture. The reaction was stirred at room temperature for 24 h and sequentially washed with 1 N hydrochloric acid, saturated sodium hydrocarbonate. After separation and concentration to remain a small amount of dichloromethane, MTBE was used for precipitation. The solid was filtered over Buchner funnel to get 5.9 g compound of formula Va.

$^1$H NMR (400 MHz, Chloroform-d) δ7.26 (m, 5H), 4.99 (d, J=8.3 Hz, 1H), 4.59 (m, 1H), 4.32-4.17 (m, 2H), 3.62 (s, 197H), 3.36 (s, 3H), 3.08 (m, 2H), 1.40 (s, 9H).

Example 3: Preparation of the Compound of Formula IVa 8 g compound of formula Va was added to the flask, and dissolved by 15 mL dichloromethane. Under stirring, 10 mL trifluoroacetic acid was added and the solution was stirred at room temperature for 18 h. After pH was adjusted to 7-8, the mixture was extracted by dichloromethane. After separation and concentration to remain a small amount of dichloromethane, MTBE was used for precipitation. The solid was filtered over Buchner funnel to get 6 g compound of formula IVa.

$^1$H NMR (400 MHz, Chloroform-d) δ7.26 (m, 5H), 4.33-4.19 (m, 2H), 4.01-3.41 (m, 195H), 3.37 (s, 3H), 3.18-2.97 (m, 2H).

Example 4: Preparation of the Compound of Formula IIIa 1.8 g compound of formula IVa was added to the flask, and dissolved by 20 mL dichloromethane. Under stirring, compound of formula VIa (0.4 g) was added and the reaction was continued to stir for 18 h at room temperature. MTBE was used for precipitation. The solid was filtered over Buchner funnel to get 1.2 g compound of formula IIIa.

$^1$H NMR (400 MHz, Chloroform-d) δ7.26 (m, 6H), 4.87 (m, J=8.6, 5.7 Hz, 1H), 4.31-4.10 (m, 3H), 3.62 (m, 188H), 3.35 (s, 3H), 3.19-3.04 (m, 2H), 1.29 (d, J=6.7 Hz, 3H), 0.81 (s, 9H), 0.02 (d, J=14.2 Hz, 6H).

Example 5: Preparation of the Compound of Formula IIa

Acetic acid (6 g) was added to the solution of KF (2 g) in 40 mL H2O. To the solution was added compound of formula IIIa (6 g). The reaction was stirred at room temperature for 24 h. After pH was adjusted to 7-8, the resulting mixture was extracted by dichloromethane. The organic phase was separated and washed by brine and precipitated by MTBE. The solid was filtered over Buchner funnel to get 4 g compound of formula IIa.

$^1$H NMR (400 MHz, Chloroform-d) δ7.26 (m, 6H), 4.89 (m, 1H), 4.41-4.08 (m, 3H), 3.63 (s, 191H), 3.36 (s, 3H), 3.27-3.03 (m, 2H), 1.31 (d, J=6.8 Hz, 3H).

Example 6: Preparation of the Compound of Formula Ia 1.65 g compound of formula IIa and DL-lactide (1.54 g) were sequentially added to the flask, and dissolved by 8 mL dichloromethane under stirring. After addition of DBU (46 mg), the reaction was stirred at room temperature for 1 h. The solution was diluted by 50 mL dichloromethane. The organic phase was sequentially washed by 1 N hydrochloric acid and brine. MTBE was used for precipitation. The solid was filtered over Buchner funnel to get 2.5 g compound of formula Ia. The molecular weight was calculated to be 3900 according to H-NMR. PDI (polydisperity index) was 1.07 according to GPC (gel permeation chromatography).

$^1$H NMR (400 MHz, DMSO-$d_6$) δ8.54-8.37 (m, 1H), 7.35-7.14 (m, 5H), 5.48 (d, J=5.9 Hz, 1H), 5.18 (m, 22H), 5.01 (m, 1H), 4.53-4.42 (m, 1H), 4.16 (m, 3H), 3.50 (s, 189H), 3.24 (s, 3H), 3.12-2.91 (m, 2H), 1.57-1.17 (m, 76H).

Example 7: Preparation of the Compound of Formula Va'

10 g polyethylene glycol monomethyl ether (number-average molecular weight of 2000) was added to the flask, dissolved by 50 mL dichloromethane. Under stirring, Boc-protected phenylalanine (3.6 g), EDCI (5.71 g) and DMAP (1.52 g) were sequentially added to the mixture. The reaction was stirred at room temperature for 24 h and sequentially washed with 1 N hydrochloric acid, saturated sodium hydrocarbonate. After separation and concentration to remain a small amount of dichloromethane, MTBE was used for precipitation. The solid was filtered over Buchner funnel to get 9.5 g compound of formula Va'.

¹H NMR (400 MHz, Chloroform-d) δ7.26 (m, 5H), 4.99 (d, J=8.3 Hz, 1H), 4.59 (m, 1H), 4.32-4.17 (m, 2H), 3.62 (s, 197H), 3.36 (s, 3H), 3.08 (m, 2H), 1.40 (s, 9H).

Example 8: Preparation of the Compound of Formula IVa'

8 g compound of formula Va' was added to the flask, and dissolved by 15 mL dichloromethane. Under stirring, 10 mL trifluoroacetic acid was added and the solution was stirred at room temperature for 18 h. After pH was adjusted to 7-8, the mixture was extracted by dichloromethane. After separation and concentration to remain a small amount of dichloromethane, MTBE was used for precipitation. The solid was filtered over Buchner funnel to get 6 g compound of formula IVa'.
¹H NMR (400 MHz, Chloroform-d) δ7.26 (m, 5H), 4.33-4.19 (m, 2H), 4.01-3.41 (m, 195H), 3.37 (s, 3H), 3.18-2.97 (m, 2H).

Example 9: Preparation of the Compound of Formula Ia'

1.65 g compound of formula IIa and DL-lactide (1.54 g) were sequentially added to the flask, and dissolved by 8 mL toluene under stirring. After addition of stannous octoate (46 mg), the reaction was stirred at 80° C. for 5 h. The solution was diluted by 50 mL dichloromethane. The organic phase was sequentially washed by 1 N hydrochloric acid and brine. MTBE was used for precipitation. The solid was filtered over Buchner funnel to get 2.5 g compound of formula Ia'. The molecular weight was calculated to be 3900 according to H-NMR. PDI (polydisperity index) was 1.04 according to GPC (gel permeation chromatography).
¹H NMR (400 MHz, DMSO-$d_6$) δ8.54-8.37 (m, 1H), 7.35-7.14 (m, 5H), 5.48 (d, J=5.9 Hz, 1H), 5.18 (m, 22H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 1.57-1.17 (m, 76H).

Example 10: Preparation of the Compound of Formula Vb 3 g polyethylene glycol monomethyl ether (number-average molecular weight of 2000) was added to the flask, dissolved by 20 mL dichloromethane. Under stirring, the mixture was sequentially added Boc-protected 3-(2-naphthyl)-alanine (1.4 g), EDCI (1.71 g) and DMAP (0.55 g). The reaction was stirred at room temperature for 18 h and sequentially washed with 1 N hydrochloric acid, saturated sodium hydrocarbonate. MTBE was used for precipitation. The solid was filtered over Buchner funnel to get 2.5 g compound of formula Vb.
¹H NMR (400 MHz, Chloroform-d) δ 7.83-7.73 (m, 3H), 7.63-7.58 (m, 1H), 7.49-7.40 (m, 2H), 7.26 (d, 2H), 5.03 (d, J=8.2 Hz, 1H), 4.67 (dt, J=8.1, 5.9 Hz, 1H), 4.35-4.17 (m, 2H), 3.63 (m, 188H), 3.37 (s, 3H), 3.25 (m, 2H), 1.39 (s, 9H).

Example 11: Preparation of the Compound of Formula IVb 2.7 g compound of formula Vb was added to the flask, and dissolved by 10 mL dichloromethane. Under stirring, 8 mL trifluoroacetic acid was added and the solution was stirred at room temperature for 5 h. After pH was adjusted to 7-8, the mixture was extracted by dichloromethane. After separation and concentration to remain a small amount of dichloromethane, MTBE was used for precipitation. The solid was filtered over Buchner funnel to get 2.5 g compound of formula IVb.
¹H NMR (400 MHz, Chloroform-d) δ 7.78 (t, J=8.0 Hz, 3H), 7.66 (s, 1H), 7.44 (m, 2H), 7.33 (m, 1H), 4.26 (m, 2H), 3.85 (m, 1H), 3.63 (s, 191H), 3.36 (s, 3H), 3.30-3.17 (m, 1H), 3.05 (dd, J=13.5, 7.7 Hz, 1H).

Example 12: Preparation of the Compound of Formula IIIb 2.5 g compound of formula IVb was added to the flask, and dissolved by 10 mL dichloromethane. Under stirring, compound of formula VIa (0.5 g) was added and the reaction was continued to stir for 12 h at room temperature. MTBE was used for precipitation. The solid was filtered over Buchner funnel to get 2.4 g compound of formula IIIb.
¹H NMR (400 MHz, Chloroform-d) δ7.26 (m, 6H), 4.87 (m, J=8.6, 5.7 Hz, 1H), 4.31-4.10 (m, 3H), 3.62 (m, 188H), 3.35 (s, 3H), 3.19-3.04 (m, 2H), 1.29 (d, J=6.7 Hz, 3H), 0.81 (s, 9H), 0.02 (d, J=14.2 Hz, 6H).

Example 13: Preparation of the Compound of Formula IIb

Acetic acid (2.4 g) was added to the solution of KF (0.8 g) in 20 mL H2O. To the solution was added compound of formula IIIb (2.4 g). The reaction was stirred at room temperature for 6 h. After pH was adjusted to 7-8, the resulting mixture was extracted by dichloromethane. The organic phase was separated and washed by brine and precipitated by MTBE. The solid was filtered over Buchner funnel to get 1.2 g compound of formula IIb.
¹H NMR (400 MHz, Chloroform-d) δ 7.84-7.70 (m, 3H), 7.60 (d, J=1.6 Hz, 1H), 7.50-7.37 (m, 2H), 7.12 (d, J=8.3 Hz, 1H), 4.97 (m, 1H), 4.33-4.12 (m, 3H), 3.63 (s, 189H), 3.36 (s, 5H), 1.31 (d, J=6.8 Hz, 3H).

Example 14: Preparation of the Compound of Formula Ib 1 g compound of formula IIb and DL-lactide (0.73 g) were sequentially added to the flask, and dissolved by 10 mL toluene under stirring. After addition of magnesium 2-ethylhexanoate (24 mg), the reaction was stirred at 90° C. for 3 h. The solution was diluted by dichloromethane. The organic phase was sequentially washed by 1 N hydrochloric acid and brine. MTBE was used for precipitation. The solid was filtered over Buchner funnel to get 1.2 g compound of formula Ib. The molecular weight was calculated to be 4200 according to H-NMR. PDI was 1.05 according to GPC.
¹H NMR (400 MHz, Chloroform-d) δ 7.77 (m, 3H), 7.60 (d, J=4.3 Hz, 1H), 7.44 (m, 2H), 7.26 (s, 1H), 6.69-6.50 (m, 1H), 5.28-4.82 (m, 22H), 4.30 (m, 3H), 3.63 (s, 185H), 3.37 (s, 5H), 2.74 (d, J=14.1 Hz, 1H), 1.66-1.33 (m, 67H).

Example 15: Preparation of the Compound of Formula IIIc 10 g polyethylene glycol monomethyl ether (number-average molecular weight of 2000) was added to the flask, dissolved by 50 mL dichloromethane. Under stirring, the mixture was sequentially added succinic anhydride (1 g) and DMAP (0.6 g). After stirring for 5 h, the reaction mixture was precipitated by MTBE. The solid was filtered over Buchner funnel to get 7 g compound of formula IIIc.

¹H NMR (400 MHz, Chloroform-d) δ 4.25 (q, J=4.1 Hz, 2H), 3.63 (m, 186H), 3.37 (s, J=2.9 Hz, 3H), 2.63 (m, 4H).

Example 16: Preparation of the Compound of Formula IIc 3.5 g compound of formula IIIc was added to the flask, and dissolved by 15 mL DMF. Under stirring, the mixture was sequentially added phenylalaninol (0.8 g), EDCI (1.9 g) and HOBT (1.34 g). After stirring at room temperature for 18 h, the organic phase was sequentially washed with 1 N hydrochloric acid and brine, then precipitated by MTBE. The solid was filtered over Buchner funnel to get 2.5 g compound of formula IIc.

¹H NMR (400 MHz, Chloroform-d) δ 7.26 (s, 5H), 6.24 (d, J=8.0 Hz, 1H), 4.28-4.19 (m, 2H), 4.14 (m, 1H), 3.63 (m, 195H), 3.37 (s, 3H), 3.02 (s, 1H), 2.86 (d, J=7.4 Hz, 2H), 2.79-2.56 (m, 2H), 2.50-2.38 (m, 2H).

Example 17: Preparation of the Compound of Formula Ic 1 g compound of formula IIc, D-lactide (0.42 g) and L-lactide (0.42 g) were sequentially added to the flask, and dissolved by 10 mL dichloromethane under stirring. After addition of DBU (30 mg), the reaction was stirred at 50° C. for 10 min. The organic phase was sequentially washed by 1 N hydrochloric acid and brine. MTBE was used for precipitation. The solid was filtered over Buchner funnel to get 1.2 g compound of formula Ic. The molecular weight was calculated to be 4000 according to H-NMR. PDI was 1.07 according to GPC.

¹H NMR (400 MHz, Chloroform-d) δ7.26 (s, 5H), 6.19-5.96 (m, 1H), 5.17 (m, 23H), 4.36 (td, 2H), 4.27-4.05 (m, 4H), 3.64 (s, 197H), 3.38 (s, 3H), 2.93-2.68 (m, 2H), 2.64 (t, J=6.9 Hz, 2H), 2.48-2.38 (m, 2H), 1.66-1.43 (m, 73H).

Example 18: Preparation of the Compound of Formula IId 2.5 g compound of formula IIIc was added to the flask, and dissolved by 15 mL DMF. Under stirring, the mixture was sequentially added 3-(2-naphthyl)-alaninol (0.8 g), EDCI (0.9 g) and HOBT (0.5 g). After stirring at room temperature for 24 h, the organic phase was sequentially washed with 1 N hydrochloric acid, saturated NaHCO₃ aqueous solution and brine, then precipitated by MTBE. The solid was filtered over Buchner funnel to get 2 g compound of formula IId.

¹H NMR (400 MHz, Chloroform-d) δ 7.83-7.71 (m, 3H), 7.67 (d, J=1.6 Hz, 1H), 7.51-7.33 (m, 3H), 6.29 (d, J=7.9 Hz, 1H), 4.31-4.13 (m, 3H), 3.63 (s, 193H), 3.37 (s, 3H), 3.03 (d, J=7.5 Hz, 3H), 2.80-2.57 (m, 2H), 2.44 (m, 2H).

Example 19: Preparation of the Compound of Formula Id 1 g compound of formula IId, D-lactide (0.41 g) and L-lactide (0.41 g) were sequentially added to the flask, and dissolved by 10 mL dichloromethane under stirring. After addition of DBU (28 mg), the reaction was stirred at 25° C. for 1 h. The organic phase was sequentially washed by 1 N hydrochloric acid and brine. MTBE was used for precipitation. The solid was filtered over Buchner funnel to get 1.2 g compound of formula Id. The molecular weight was calculated to be 4000 according to H-NMR. PDI was 1.07 according to GPC.

¹H NMR (400 MHz, Chloroform-d) δ 7.79 (t, J=8.7 Hz, 3H), 7.63 (s, 1H), 7.45 (m, 2H), 7.37-7.30 (m, 1H), 6.32-6.08 (m, 1H), 5.31-5.06 (m, 23H), 4.52 (s, 1H), 4.35 (p, J=6.8 Hz, 1H), 4.15 (ddd, J=17.4, 6.6, 5.6 Hz, 4H), 3.63 (d, J=3.0 Hz, 200H), 3.37 (s, 3H), 3.11-2.89 (m, 2H), 2.75 (s, 1H), 2.64 (t, J=6.9 Hz, 2H), 2.44 (dd, J=6.8, 3.1 Hz, 2H), 1.67-1.43 (m, 73H).

Example 20: Preparation of the Compound of Formula IIIe 8 g polyethylene glycol monomethyl ether (number-average molecular weight of 2000) was added to the flask, dissolved by 100 mL dichloromethane. Under stirring, the mixture was sequentially added p-formylbenzoic acid (2.5 g), DCC (6.56 g) and DMAP (2.18 g). After stirring at room temperature for 10 h, the reaction mixture was precipitated by MTBE. The solid was filtered over Buchner funnel to get 5.5 g compound of formula IIIe.

¹H NMR (400 MHz, Chloroform-d) δ 10.08 (s, 1H), 8.26-8.14 (m, 2H), 8.00-7.88 (m, 2H), 4.52-4.45 (m, 2H), 3.62 (s, 189H), 3.36 (s, 3H).

Example 21: Preparation of the Compound of Formula IIe 2.5 g compound of formula IIIe was added to the flask, dissolved by 50 mL ethanol. Under stirring, the mixture was added sodium borohydride (100 mg). After stirring for 1 h, the reaction mixture was sequentially washed with 1 N hydrochloric acid and brine. The organic phase was precipitated by MTBE. The solid was filtered and dried under vacuum at room temperature to get 0.8 g compound of formula IIe.

¹H NMR (400 MHz, Chloroform-d) δ 8.02 (d, J=8.2 Hz, 2H), 7.42 (d, J=8.0 Hz, 2H), 4.74 (d, J=5.7 Hz, 2H), 4.45 (m, 2H), 3.62 (m, 203H), 3.36 (s, 3H), 2.65 (t, J=6.1 Hz, 1H).

Example 22: Preparation of the Compound of Formula Ie 0.8 g compound of formula IIe, DL-lactide (0.7 g) were sequentially added to the flask, and dissolved by 10 mL dichloromethane. After addition of DBU (16 mg), the reaction was stirred at 10° C. for 30 min. The organic phase was sequentially washed by 1 N hydrochloric acid and brine. MTBE was used for precipitation. The solid was filtered and dried under vacuum at room temperature to get 0.8 g compound of formula Ie. The molecular weight was calculated to be 3800 according to H-NMR. PDI was 1.06 according to GPC.

¹H NMR (400 MHz, Chloroform-d) δ 8.14-7.95 (m, 2H), 7.37 (d, J=8.0 Hz, 2H), 5.31-5.09 (m, 20H), 4.53-4.41 (m, 2H), 4.34 (p, J=6.8 Hz, 1H), 3.63 (m, 200H), 3.37 (s, 3H), 2.73 (d, J=14.5 Hz, 1H), 1.68-1.41 (m, 60H).

Example 23: Preparation of the Compound of Formula If

According to the synthetic route of the compound of formula Ia, using polyethylene glycol monomethyl ether (number-average molecular weight of 4000), racemic tryptophan, DL-lactide as starting material, through introduction of linker to initiate polymerization, to get compound of formula If. The molecular weight was calculated to be 7900 according to H-NMR. PDI was 1.07 according to GPC.

¹H NMR (400 MHz, DMSO-d₆) δ10.5 (s, 1H), 7.62 (d, 1H), 7.30 (d, 1H), 7.18 (s, 1H), 7.12 (m, 2H), 5.48 (d, J=5.9 Hz, 1H), 5.18 (m, 54H), 5.01 (m, 1H), 4.53-4.42 (m, 1H), 4.16 (m, 3H), 3.50 (s, 364H), 3.24 (s, 3H), 3.30-3.12 (m, 2H), 1.57-1.17 (m, 160H).

Example 24: Preparation of the Compound of Formula Ig

According to the synthetic route of the compound of formula Ia, using polyethylene glycol monomethyl ether (number-average molecular weight of 5000), tyrosine, DL-lactide as starting material, through introduction of linker to initiate polymerization, to get compound of formula Ig. The molecular weight was calculated to be 10000 according to H-NMR. PDI was 1.09 according to GPC.

¹H NMR (400 MHz, DMSO-d₆) δ7.15 (d, 2H), 6.8 (d, 2H), 5.48 (d, J=5.9 Hz, 1H), 5.33 (s, 1H), 5.18 (m, 68H), 5.01 (m, 1H), 4.53-4.42 (m, 1H), 4.16 (m, 3H), 3.50 (s, 455H), 3.24 (s, 3H), 3.42-3.20 (m, 2H), 1.57-1.17 (m, 208H).

Example 25: Preparation of the Compound of Formula Ih

According to the synthetic route of the compound of formula Ia, using polyethylene glycol monomethyl ether (number-average molecular weight of 2000), histidine, DL-lactide as starting material, through introduction of linker to initiate polymerization, to get compound of formula Ih. The molecular weight was calculated to be 5000 according to H-NMR. PDI was 1.05 according to GPC.

¹H NMR (400 MHz, DMSO-d₆) δ12.0 (s, 1H), 8.77 (s, 1H), 7.63 (s, 1H), 5.48 (d, J=5.9 Hz, 1H), 5.18 (m, 42H), 5.01 (m, 1H), 4.53-4.42 (m, 1H), 4.16 (m, 3H), 3.50 (s, 180H), 3.24 (s, 3H), 3.82-3.56 (m, 2H), 1.57-1.17 (m, 126H).

Example 26: Preparation of the Compound of Formula Ii

According to the synthetic route of the compound of formula Ia, using polyethylene glycol monobenzyl ether (number-average molecular weight of 2000), phenylalanine, DL-lactide as starting material, through introduction of linker to initiate polymerization, to get compound of formula Ih. The molecular weight was calculated to be 4000 according to H-NMR. PDI was 1.06 according to GPC.

¹H NMR (400 MHz, DMSO-d₆) δ8.54-8.37 (m, 1H), 7.45 (d, 2H), 7.38-7.14 (m, 8H), 5.48 (d, J=5.9 Hz, 1H), 5.18 (m, 23H), 5.01 (m, 1H), 4.82 (s, 2H), 4.53-4.42 (m, 1H), 4.16 (m, J=27.5, 12.4, 6.1 Hz, 3H), 3.50 (s, 189H), 3.12-2.91 (m, 2H), 1.57-1.17 (m, 68H).

Example 27: Preparation of the Compound of Formula Ij

According to the synthetic route of the compound of formula Ia, using polyethylene glycol monobenzyl ether (number-average molecular weight of 10000), phenylalanine, glycine, DL-lactide as starting material, through introduction of linker to initiate polymerization, to get compound of formula Ij. The molecular weight was calculated to be 20000 according to H-NMR. PDI was 1.08 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 138H), 5.01 (m, 1H), 4.53-4.42 (m, 1H), 4.16 (m, J=27.5, 12.4, 6.1 Hz, 3H), 4.03 (s, 2H), 3.50 (s, 910H), 3.24 (s, 3H), 3.12-2.91 (m, 2H), 1.57-1.17 (m, 421H).

Example 28: Preparation of the Compound of Formula Ik

According to the synthetic route of the compound of formula Ia, using polyethylene glycol monomethyl ether (number-average molecular weight of 6000), phenylalanine, glycine, D-tyrosine, DL-lactide as starting material, through introduction of linker to initiate polymerization, to get compound of formula Ik. The molecular weight was calculated to be 14000 according to H-NMR. PDI was 1.07 according to GPC.

¹H NMR (400 MHz, DMSO-d₆) δ8.54-8.37 (m, 1H), 7.35-7.14 (m, 5H), 7.10 (d, 2H), 6.75 (d, 2H), 5.48 (d, J=5.9 Hz, 1H), 5.18 (m, 108H), 5.01 (m, 1H), 4.53-4.42 (m, 1H), 4.16 (m, 3H), 3.50 (s, 545H), 3.24 (s, 3H), 3.08-2.88 (m, 2H), 3.12-2.91 (m, 2H), 1.57-1.17 (m, 320H).

Example 29: Preparation of the Compound of Formula Il

According to the synthetic route of the compound of formula Ia, using polyethylene glycol monomethyl ether (number-average molecular weight of 2000), phenylalanine, DL-lactide as starting material, through introduction of linker to initiate polymerization, and protecting the termini of PLA by acetyl group to get compound of formula Il. The molecular weight was calculated to be 7000 according to H-NMR. PDI was 1.06 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 66H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 2.03 (s, 3H), 1.57-1.17 (m, 200H).

Example 30: Preparation of the Compound of Formula Im

According to the synthetic route of the compound of formula Ia, using polyethylene glycol monomethyl ether (number-average molecular weight of 2000), phenylalanine, DL-lactide as starting material, through introduction of linker to initiate polymerization, and protecting the termini of PLA by benzoyl group to get compound of formula Im. The molecular weight was calculated to be 4500 according to H-NMR. PDI was 1.06 according to GPC.

¹H NMR (400 MHz, DMSO-d₆) δ8.54-8.37 (m, 1H), 8.00 (d, 2H), 7.63 (d, 1H), 7.58 (dd, 2H), 7.35-7.14 (m, 5H), 5.48 (d, J=5.9 Hz, 1H), 5.18 (m, 30H), 5.01 (m, 1H), 4.53-4.42 (m, 3H), 4.16 (m, J=27.5, 12.4, 6.1 Hz, 3H), 3.50 (s, 181H), 3.24 (s, 3H), 3.12-2.91 (m, 2H), 2.56 (t, 2H), 1.57-1.17 (m, 91H).

Example 31: Preparation of the Compound of Formula In

According to the synthetic route of the compound of formula Ia, using polyethylene glycol monomethyl ether (number-average molecular weight of 2000), phenylalanine, DL-lactide as starting material, through introduction of linker to initiate polymerization, and protecting the termini of PLA by Boc-protected phenylalanine to get compound of formula In. The molecular weight was calculated to be 5000 according to H-NMR. PDI was 1.04 according to GPC.

¹H NMR (400 MHz, DMSO-d₆) δ8.54-8.37 (m, 1H), 7.35-7.14 (m, 10H), 5.48 (d, J=5.9 Hz, 1H), 5.18 (m, 37H), 5.01 (m, 2H), 4.53-4.42 (m, 3H), 4.16 (m, J=27.5, 12.4, 6.1 Hz, 3H), 3.50 (s, 180H), 3.24 (s, 3H), 3.12-2.91 (m, 4H), 2.56 (t, 2H), 1.57-1.17 (m, 112H).

Example 32: Preparation of the Compound of Formula Io

According to the synthetic route of the compound of formula Ia, using polyethylene glycol monomethyl ether (number-average molecular weight of 2000), benzoyl-protected lysine, DL-lactide as starting material, through introduction of linker to initiate polymerization, to get compound of formula Io. The molecular weight was calculated to be 4000 according to H-NMR. PDI was 1.08 according to GPC.

¹H NMR (400 MHz, DMSO-d₆) δ8.50 (m, 1H), 8.05 (d, 2H), 7.72 (d, 1H), 7.58 (dd, 2H), 5.48 (d, J=5.9 Hz, 1H), 5.18 (m, 22H), 5.01 (m, 1H), 4.53-4.42 (m, 1H), 4.16 (m, 3H), 3.50 (s, 182H), 3.32 (t, 2H), 3.24 (s, 3H), 3.12-2.91 (m, 2H), 1.78 (m, 2H), 1.57-1.17 (m, 78H).

Example 33: Preparation of the Compound of Formula Ip

According to the synthetic route of the compound of formula Ia, using polyethylene glycol monomethyl ether (number-average molecular weight of 2000), dithiodipropionic acid, phenylalanine, DL-lactide as starting material, through introduction of linker to initiate polymerization, to get compound of formula Ip. The molecular weight was calculated to be 4300 according to H-NMR. PDI was 1.09 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 25H), 5.01 (m, 1H), 4.53-4.42 (m, 1H), 4.16 (m, 3H), 3.50 (s, 180H), 3.24 (s, 3H), 3.12-2.91 (m, 4H), 2.80 (t, 2H), 2.58 (t, 2H), 2.44 (t, 2H), 1.57-1.17 (m, 76H).

Example 34: Preparation of the Compound of Formula Iq

According to the synthetic route of the compound of formula Ia, using polyethylene glycol monomethyl ether (number-average molecular weight of 2000), phthalimide, Boc-protected phenylalanine, DL-lactide as starting material, through introduction of linker to initiate polymerization, to get compound of formula Iq. The molecular weight was calculated to be 5000 according to H-NMR. PDI was 1.07 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 39H), 5.01 (m, 1H), 4.53-4.42 (m, 3H), 4.16 (m, J=27.5, 12.4, 6.1 Hz, 3H), 3.57 (t, 2H), 3.50 (s, 180H), 3.24 (s, 3H), 3.12-2.91 (m, 2H), 2.64 (t, 2H), 2.56 (t, 2H), 1.57-1.17 (m, 118H).

Example 35: Preparation of the Compound of Formula Ir

According to the synthetic route of the compound of formula Ia, using polyethylene glycol monomethyl ether (number-average molecular weight of 2000), thioacetic acid, Boc-protected phenylalanine, DL-lactide as starting material, through introduction of linker to initiate polymerization, to get compound of formula Ir. The molecular weight was calculated to be 6000 according to H-NMR. PDI was 1.07 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 53H), 5.01 (m, 1H), 4.53-4.42 (m, 3H), 4.16 (m, J=27.5, 12.4, 6.1 Hz, 3H), 3.50 (s, 180H), 3.28 (t, 2H), 3.24 (s, 3H), 3.12-2.91 (m, 2H), 2.88 (t, 2H), 2.56 (t, 2H), 1.57-1.17 (m, 160H).

Example 36: Preparation of the Compound of Formula Is

According to the synthetic route of the compound of formula Ia, using polyethylene glycol monomethyl ether (number-average molecular weight of 4000), butyrolactone, Boc-protected phenylalanine, DL-lactide as starting material, through introduction of linker to initiate polymerization, to get compound of formula Is. The molecular weight was calculated to be 8000 according to H-NMR. PDI was 1.07 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 54H), 5.01 (m, 1H), 4.53-4.42 (m, 3H), 4.16 (m, J=27.5, 12.4, 6.1 Hz, 3H), 3.50 (s, 364H), 3.24 (s, 3H), 3.12-2.91 (m, 2H), 2.56 (t, 2H), 1.57-1.17 (m, 162H).

Example 37: Preparation of the Compound of Formula It

According to the synthetic route of the compound of formula Ia', using polyethylene glycol monomethyl ether (number-average molecular weight of 5000), Boc-protected phenylalanine, DL-lactide as starting material, through introduction of linker to initiate polymerization, to get compound of formula It. The molecular weight was calculated to be 9000 according to H-NMR. PDI was 1.07 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 54H), 5.01 (m, 1H), 4.53-4.42 (m, 1H), 4.16 (m, J=27.5, 12.4, 6.1 Hz, 3H), 3.50 (s, 454H), 3.24 (s, 3H), 3.12-2.91 (m, 2H), 1.57-1.17 (m, 160H).

Example 38: Preparation of the Compound of Formula Iu

According to the synthetic route of the compound of formula Ia', using polyethylene glycol monomethyl ether (number-average molecular weight of 3000), Boc-protected D-phenylalanine, DL-lactide as starting material, through introduction of linker to initiate polymerization, to get compound of formula It. The molecular weight was calculated to be 8000 according to H-NMR. PDI was 1.07 according to GPC.

¹H NMR (400 MHz, DMSO-d₆) δ8.54-8.37 (m, 1H), 7.35-7.14 (m, 5H), 5.48 (d, J=5.9 Hz, 1H), 5.18 (m, 68H), 5.01 (m, 1H), 4.53-4.42 (m, 1H), 4.16 (m, J=27.5, 12.4, 6.1 Hz, 3H), 3.50 (s, 274H), 3.24 (s, 3H), 3.12-2.91 (m, 2H), 1.57-1.17 (m, 208H).

Example 39: Preparation of the Compound of Formula Iv

According to the synthetic route of the compound of formula Ia', using polyethylene glycol monomethyl ether (number-average molecular weight of 10000), Boc-protected L-tryptophan, DL-lactide as starting material, through introduction of linker to initiate polymerization, to get compound of formula Iv. The molecular weight was calculated to be 30000 according to H-NMR. PDI was 1.07 according to GPC.

$^1$H NMR (400 MHz, DMSO-d$_6$) δ10.5 (s, 1H), 7.62 (d, 1H), 7.30 (d, 1H), 7.18 (s, 1H), 7.12 (m, 2H), 5.48 (d, J=5.9 Hz, 1H), 5.18 (m, 278H), 5.01 (m, 1H), 4.53-4.42 (m, 1H), 4.16 (m, 3H), 3.50 (s, 908H), 3.24 (s, 3H), 3.30-3.12 (m, 2H), 1.57-1.17 (m, 840H).

Example 40: Preparation of the Compound of Formula Iw

According to the synthetic route of the compound of formula Ia', using polyethylene glycol monomethyl ether (number-average molecular weight of 20000), Fmoc-protected L-phenylalanine, glycine, DL-lactide as starting material, through introduction of linker to initiate polymerization, to get compound of formula It. The molecular weight was calculated to be 40000 according to H-NMR. PDI was 1.07 according to GPC.

$^1$H NMR (400 MHz, DMSO-d$_6$) δ8.54-8.37 (m, 1H), 7.35-7.14 (m, 5H), 5.48 (d, J=5.9 Hz, 1H), 5.18 (m, 275H), 5.01 (m, 1H), 4.53-4.42 (m, 1H), 4.16 (m, J=27.5, 12.4, 6.1 Hz, 3H), 3.50 (s, 1818H), 3.24 (s, 3H), 3.12-2.91 (m, 2H), 1.57-1.17 (m, 842H).

Example 41: Preparation of the Compound of Formula Ix

According to the synthetic route of the compound of formula Ia', using polyethylene glycol monomethyl ether (number-average molecular weight of 2000) (1 g), Boc-protected L-phenylalanine (132 mg), DL-lactide (970 mg) as starting material, through introduction of linker to initiate polymerization, to get compound of formula Ix. The molecular weight was calculated to be 4200 according to H-NMR. PDI was 1.07 according to GPC.

$^1$H NMR (400 MHz, DMSO-d$_6$) δ8.54-8.37 (m, 1H), 7.35-7.14 (m, 5H), 5.48 (d, J=5.9 Hz, 1H), 5.18 (m, 26H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 1.57-1.17 (m, 79H).

Example 42: Preparation of the Compound of Formula Iy

According to the synthetic route of the compound of formula Ia, using polyethylene glycol monomethyl ether (number-average molecular weight of 2000) (1 g), Boc-protected L-phenylalanine (132 mg), DL-lactide (1.22 g) as starting material, through introduction of linker to initiate polymerization, to get compound of formula Iy. The molecular weight was calculated to be 4700 according to H-NMR. PDI was 1.07 according to GPC.

$^1$H NMR (400 MHz, DMSO-d$_6$) δ8.54-8.37 (m, 1H), 7.35-7.14 (m, 5H), 5.48 (d, J=5.9 Hz, 1H), 5.18 (m, 33H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 1.57-1.17 (m, 99H).

Example 43: Preparation of the Compound of Formula Iz

According to the synthetic route of the compound of formula Ia, using polyethylene glycol monomethyl ether (number-average molecular weight of 2000) (1 g), Boc-protected L-phenylalanine (132 mg), DL-lactide (2.73 g) as starting material, through introduction of linker to initiate polymerization, to get compound of formula Iz. The molecular weight was calculated to be 5000 according to H-NMR. PDI was 1.07 according to GPC.

$^1$H NMR (400 MHz, DMSO-d$_6$) δ8.54-8.37 (m, 1H), 7.35-7.14 (m, 5H), 5.48 (d, J=5.9 Hz, 1H), 5.18 (m, 37H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 1.57-1.17 (m, 110H).

Example 44: Preparation of the Compound of Formula Iaa

According to the synthetic route of the compound of formula Ia, using polyethylene glycol monomethyl ether (number-average molecular weight of 2000) (1 g), Boc-protected L-phenylalanine (132 mg), DL-lactide (1.47 g) as starting material, through introduction of linker to initiate polymerization, to get compound of formula Iaa. The molecular weight was calculated to be 5200 according to H-NMR. PDI was 1.07 according to GPC.

$^1$H NMR (400 MHz, DMSO-d$_6$) δ8.54-8.37 (m, 1H), 7.35-7.14 (m, 5H), 5.48 (d, J=5.9 Hz, 1H), 5.18 (m, 40H), 5.01 (m, 1H), 4.53-4.42 (m, 1H), 4.16 (m, J=27.5, 12.4, 6.1 Hz, 3H), 3.50 (s, 189H), 3.24 (s, 3H), 3.12-2.91 (m, 2H), 1.57-1.17 (m, 123H).

Example 45: Preparation of the Lyophilized Polymeric Micellar Formulation of Paclitaxel 500 mg amphiphilic block copolymer of formula Ia and 100 mg paclitaxel were added into 500 mL flask, and dissolved by 100 mL acetonitrile. The solution was placed in the shaker and shaked for 30 min at room temperature. A transparent thin film was formed around the wall of the flask after evaporation of acetonitrile. 150 mL pure water at 30° C. was immediately introduced to this flask, and a homogeneous solution with obvious blue opalescence was formed upon shaking. The solution was filtered over 0.22 μm filtration membrane, and freeze-dried into a white powder in the lyophilizer. The content of paclitaxel in the solid was 16% as detected by HPLC.

The lyophilized powder was redissolved by physiological saline to a solution with the concentration of 5 mg/mL. The solution was stable for more than 72 h at room temperature.

Example 46: Preparation of the Lyophilized Polymeric Micellar Formulation of Paclitaxel 500 mg amphiphilic block copolymer of formula Ia and 150 mg paclitaxel were added into 500 mL flask, and dissolved by 100 mL acetonitrile. The solution was placed in the shaker and shaked for 30 min at room temperature. A transparent thin film was formed around the wall of the flask after evaporation of acetonitrile. 150 mL pure water at 30° C. was immediately introduced to this flask, and a homogeneous solution with obvious blue opalescence was formed upon shaking. The solution was filtered over 0.22 μm filtration membrane, and freeze-dried into a white powder in the lyophilizer. The content of paclitaxel in the solid was 23% as detected by HPLC.

The lyophilized powder was redissolved by physiological saline to a solution with the concentration of 5 mg/mL. The solution was stable for more than 72 h at room temperature.

Figure 13:
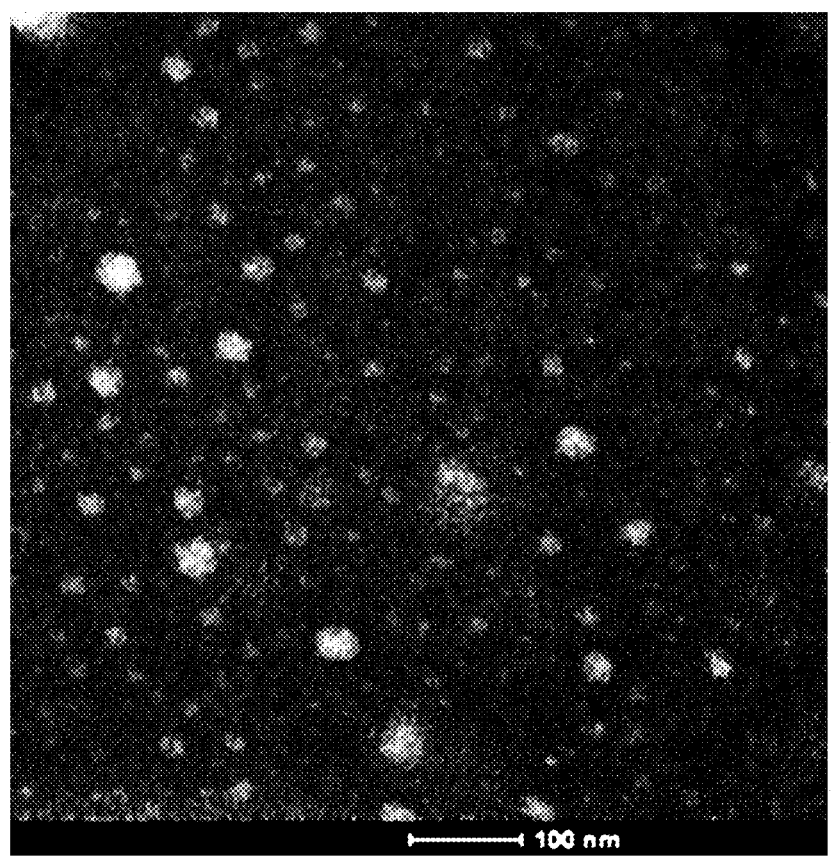
FIG. 13 is the transmission electron micrograph of the micelle by the copolymer of formula Ia and paclitaxel.
Figure 14:
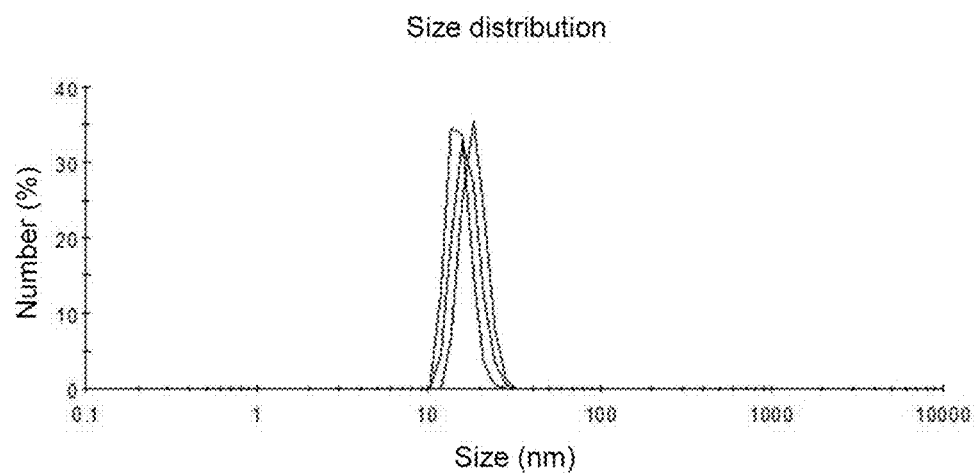
FIG. 14 is the particle size distribution diagram of the micelle formed by the copolymer of formula Ia and paclitaxel.
Figure 15:
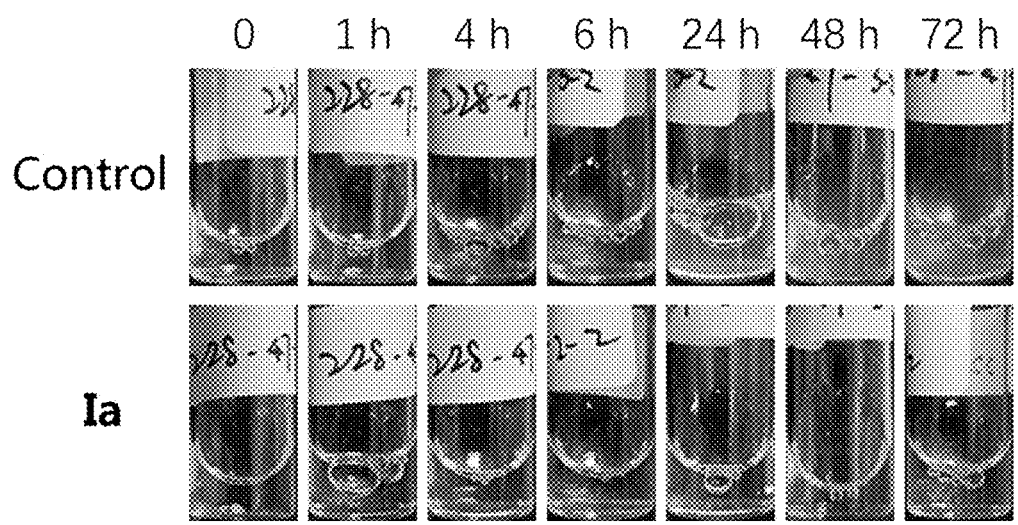
FIG. 15 is a graph showing the stability comparison of the micelle formed by unmodified PEG-PLA (from Samyang, Korea) and paclitaxel (weight ratio of paclitaxel and the copolymer as 20:100), and the micelle formed by the copolymer of formula Ia in the present disclosure and paclitaxel (weight ratio of paclitaxel and the copolymer as 20:100)
Figure 16:
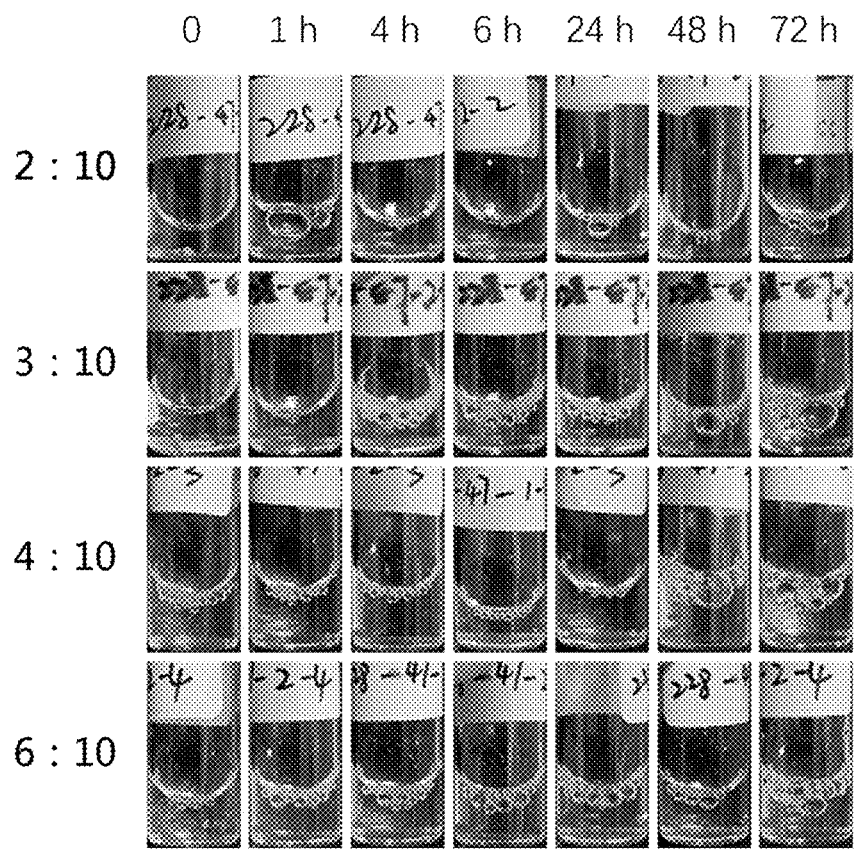
FIG. 16 is a graph showing the stability comparison of the micelles formed by paclitaxel and the copolymer of formula Ia in different ratio.

Example 47: Preparation of the Lyophilized Polymeric Micellar Formulation of Paclitaxel 500 mg amphiphilic block copolymer of formula Ia and 200 mg paclitaxel were added into 500 mL flask, and dissolved by 100 mL acetonitrile. The solution was placed in the shaker and shaked for 2 h at room temperature. A transparent thin film was formed around the wall of the flask after evaporation of acetonitrile. 150 mL pure water at 60° C. was immediately introduced to this flask, and a homogeneous solution with obvious blue opalescence was formed upon shaking. The solution was filtered over 0.22 µm filtration membrane, and freeze-dried into a white powder in the lyophilizer. The content of paclitaxel in the solid was 28% as detected by HPLC. The result for particle size measurement was shown in FIG. 14. The average particle size was 20.2 nm after taking the average of three tests. The transmission electron micrograph was shown in FIG. 13.

The lyophilized powder was redissolved by physiological saline to a solution with the concentration of 5 mg/mL. The solution was stable for more than 72 h at room temperature.

Example 48: Preparation of the Lyophilized Polymeric Micellar Formulation of Paclitaxel 500 mg amphiphilic block copolymer of formula Ia and 300 mg paclitaxel were added into 500 mL flask, and dissolved by 100 mL acetonitrile. The solution was placed in the shaker and shaked for 30 min at room temperature. A transparent thin film was formed around the wall of the flask after evaporation of acetonitrile. 150 mL pure water at 30° C. was immediately introduced to this flask, and a homogeneous solution with obvious blue opalescence was formed upon shaking. The solution was filtered over 0.22 µm filtration membrane, and freeze-dried into a white powder in the lyophilizer. The content of paclitaxel in the solid was 37% as detected by HPLC.

The lyophilized powder was redissolved by physiological saline to a solution with the concentration of 5 mg/mL. The solution was stable for more than 72 h at room temperature.

Example 49: Preparation of the Lyophilized Polymeric Micellar Formulation of Paclitaxel 500 mg amphiphilic block copolymer of formula Ib and 300 mg paclitaxel were added into 500 mL flask, and dissolved by 100 mL acetonitrile. The solution was placed in the shaker and shaked for 1 h at room temperature. A transparent thin film was formed around the wall of the flask after evaporation of acetonitrile. 150 mL pure water at 50° C. was immediately introduced to this flask, and a homogeneous solution with obvious blue opalescence was formed upon shaking. The solution was filtered over 0.22 µm filtration membrane, and freeze-dried into a white powder in the lyophilizer. The content of paclitaxel in the solid was 37% as detected by HPLC.

The lyophilized powder was redissolved by physiological saline to a solution with the concentration of 5 mg/mL. The solution was stable for more than 72 h at room temperature.

Example 50: Preparation of the Lyophilized Polymeric Micellar Formulation of Paclitaxel 500 mg amphiphilic block copolymer of formula Ib and 50 mg paclitaxel were added into 500 mL flask, and dissolved by 100 mL acetonitrile. The solution was placed in the shaker and shaked for 1 h at room temperature. A transparent thin film was formed around the wall of the flask after evaporation of acetonitrile. 150 mL pure water at 50° C. was immediately introduced to this flask, and a homogeneous solution with obvious blue opalescence was formed upon shaking. The solution was filtered over 0.22 µm filtration membrane, and freeze-dried into a white powder in the lyophilizer. The content of paclitaxel in the solid was 9% as detected by HPLC.

The lyophilized powder was redissolved by physiological saline to a solution with the concentration of 3 mg/mL. The solution was stable for more than 72 h at room temperature.

Example 51: Preparation of the Lyophilized Polymeric Micellar Formulation of Paclitaxel 500 mg amphiphilic block copolymer of formula Ic and 150 mg paclitaxel were added into 500 mL flask, and dissolved by 100 mL acetonitrile. The solution was placed in the shaker and shaked for 30 min at room temperature. A transparent thin film was formed around the wall of the flask after evaporation of acetonitrile. 150 mL pure water at 30° C. was immediately introduced to this flask, and a homogeneous solution with obvious blue opalescence was formed upon shaking. The solution was filtered over 0.22 µm filtration membrane, and freeze-dried into a white powder in the lyophilizer. The content of paclitaxel in the solid was 23% as detected by HPLC.

The lyophilized powder was redissolved by physiological saline to a solution with the concentration of 5 mg/mL. The solution was stable for more than 72 h at room temperature.

Example 52: Preparation of the Lyophilized Polymeric Micellar Formulation of Docetaxel 200 mg amphiphilic block copolymer of formula Ib and 80 mg docetaxel were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 20° C. was immediately introduced to this flask, and a homogeneous solution with obvious blue opalescence was formed upon shaking. The solution was filtered over 0.22 µm filtration membrane, and freeze-dried into a white powder in the lyophilizer. The content of docetaxel in the solid was 28% as detected by HPLC.

The lyophilized powder was redissolved by physiological saline to a solution with the concentration of 5 mg/mL. The solution was stable for more than 48 h at room temperature.

Example 53: Preparation of the Lyophilized Polymeric Micellar Formulation of Eribulin 200 mg amphiphilic block copolymer of formula Ic and 40 mg eribulin were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 µm filtration membrane, and freeze-dried into a white powder in the lyophilizer. The content of eribulin in the solid was 17% as detected by HPLC.

The lyophilized powder was redissolved by physiological saline to a solution with the concentration of 5 mg/mL. The solution was stable for more than 48 h at room temperature.

Example 54: Preparation of the Lyophilized Polymeric Micellar Formulation of Irinotecan 200 mg amphiphilic block copolymer of formula Id and 40 mg irinotecan were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 60° C. was immediately introduced to this flask, and a homogeneous solution with obvious blue opalescence was formed upon shaking. The solution was filtered over 0.22 μm filtration membrane, and freeze-dried into a white powder in the lyophilizer. The content of irinotecan in the solid was 16% as detected by HPLC.

The lyophilized powder was redissolved by physiological saline to a solution with the concentration of 3 mg/mL. The solution was stable for more than 24 h at room temperature.

Example 55: Preparation of the Lyophilized Polymeric Micellar Formulation of SN-38

200 mg amphiphilic block copolymer of formula Ih and 20 mg SN-38 were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of SN-38 in the solid was 9% as detected by HPLC.

The lyophilized powder was redissolved by physiological saline to a solution with the concentration of 1.5 mg/mL. The solution was stable for more than 24 h at room temperature.

Example 56: Preparation of the Lyophilized Polymeric Micellar Formulation of Fulvestrant 200 mg amphiphilic block copolymer of formula Ih and 70 mg fulvestrant were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of fulvestrant in the solid was 25% as detected by HPLC.

The lyophilized powder was redissolved by physiological saline to a solution with the concentration of 2 mg/mL. The solution was stable for more than 72 h at room temperature.

Example 57: Preparation of the Lyophilized Polymeric Micellar Formulation of Bortezomib 200 mg amphiphilic block copolymer of formula Iu and 70 mg bortezomib were added into 250 mL flask, and dissolved by 50 mL dichloromethane. The solution was placed in the shaker and shaked for 2 h at room temperature. A transparent thin film was formed around the wall of the flask after evaporation of dichloromethane. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of bortezomib in the solid was 25% as detected by HPLC.

The lyophilized powder was redissolved by physiological saline to a solution with the concentration of 2 mg/mL. The solution was stable for more than 72 h at room temperature.

Example 58: Preparation of the Lyophilized Polymeric Micellar Formulation of GW6471

200 mg amphiphilic block copolymer of formula Is and 50 mg GW6471 were added into 250 mL flask, and dissolved by 50 mL acetone. The solution was placed in the shaker and shaked for 2 h at room temperature. A transparent thin film was formed around the wall of the flask after evaporation of acetone. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of GW6471 in the solid was 20% as detected by HPLC.

The lyophilized powder was redissolved by physiological saline to a solution with the concentration of 2 mg/mL. The solution was stable for more than 72 h at room temperature.

Example 59: Preparation of the Lyophilized Polymeric Micellar Formulation of Voriconazole 200 mg amphiphilic block copolymer of formula Ix and 70 mg voriconazole were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of voriconazole in the solid was 25% as detected by HPLC.

The lyophilized powder was redissolved by physiological saline to a solution with the concentration of 2 mg/mL. The solution was stable for more than 72 h at room temperature.

Example 60: Preparation of the Lyophilized Polymeric Micellar Formulation of Dexamethasone 200 mg amphiphilic block copolymer of formula Iy and 90 mg dexamethasone were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 μm filtration membrane, and freeze-dried into a white powder in the lyophilizer. The content of dexamethasone in the solid was 30% as detected by HPLC.

The lyophilized powder was redissolved by physiological saline to a solution with the concentration of 2 mg/mL. The solution was stable for more than 72 h at room temperature.

Example 61: Preparation of the Lyophilized Polymeric Micellar Formulation of Olaparib 200 mg amphiphilic block copolymer of formula Iz and 100 mg olaparib were added into 250 mL flask, and dissolved by 50 mL acetonitrile. The solution was placed in the shaker and shaked for 2 h at room temperature. A transparent thin film was formed around the wall of the flask after evaporation of acetonitrile. 50 mL pure water at 40° C. was immediately introduced to this flask, and a homogeneous solution with obvious blue opalescence was formed upon shaking. The solution was filtered over 0.22 μm filtration membrance, and freeze-dried into a white powder in the lyophilizer. The content of olaparib in the solid was 33% as detected by HPLC.

The lyophilized powder was redissolved by physiological saline to a solution with the concentration of 2 mg/mL. The solution was stable for more than 72 h at room temperature.

Example 62: Preparation of the Lyophilized Polymeric Micellar Formulation of Combretastatin 200 mg amphiphilic block copolymer of formula Iaa and 70 mg combretastatin were added into 250 mL flask, and dissolved by 50 mL dichloromethane. The solution was placed in the shaker and shaked for 2 h at room temperature. A transparent thin film was formed around the wall of the flask after evaporation of dichloromethane. 50 mL pure water at 40° C. was immediately introduced to this flask, and a homogeneous solution with obvious blue opalescence was formed upon shaking. The solution was filtered over 0.22 μm filtration membrance, and freeze-dried into a white powder in the lyophilizer. The content of combretastatin in the solid was 25% as detected by HPLC.

The lyophilized powder was redissolved by physiological saline to a solution with the concentration of 2 mg/mL. The solution was stable for more than 72 h at room temperature.

Example 63 Pharmacokinetics in Rats 1.1 Animals

Male SD rats (6-8 weeks, 200-250 g) were obtained from Shanghai Sippr-BK laboratory animal Co., Ltd., with animal certificate number 2008001682093.

1.2 Sample Preparation

1) Micellar paclitaxel: paclitaxel lyophilized powder prepared from Example 46 of the present invention. The weight ratio of paclitaxel to copolymer Ia (PEG-linker-PLA) is 30:100.

2) Genexol-PM: lyophilized powder of paclitaxel-load micelle of Samyang. The weight ratio of paclitaxel to copolymer (PEG-PLA) is 20:100.

3) Paclitaxel injection: purchased from Beijing SL Pharmaceutical Co., Ltd., 30 mg/5 mL*10, batch number: 20170501.

Lyophilized powder of micellar paclitaxel or Genexol-PM: An appropriate amount of normal saline was added to an appropriate amount of sample. The mixture was shaken at a speed of 200 r/min in shaker for about 20 minutes until it becomes clear prior to intravenous injection.

1.3 Drug Administration

Intravenous injection: 3 male SD rats were administered intravenously for each compound after overnight fasting, at a dose of 3 mg/kg, with a volume of 3 mL/kg.

1.4 Methods

Pre-dose and 0.0833, 0.25, 0.5, 1, 2, 4, 6, 8, and 24 hours post-dose, blood samples of each animal were collected by jugular vein puncture (approximately 0.15 mL at each time point). All collected samples were transferred to a pre-chilled EDTA-K2 tube or a pre-chilled plastic microcentrifuge tube containing 3 μL 0.5M EDTA-K2 as an anticoagulant and were placed on wet ice until centrifuged. Each collected blood sample was centrifuged at 4° C. for 15 minutes, and the plasma was collected. All plasma was stored in a freezer at about −80° C. until LCMS/MS detection.

1.5 Pharmacokinetic Results

The pharmacokinetic parameters of each group are set forth in the following Table 1.

TABLE 1

| PK parameters | Micellar paclitaxel (from example 46) | Genexol-PM | Paclitaxel injection |
|---|---|---|---|
| Dose | i.v. (3 mg/kg) | i.v. (3 mg/kg) | i.v. (3 mg/kg) |
| $C_0$ (ng/mL) | 415 ± 63.2 | 547 ± 191 | 3224 ± 140 |
| $T_{1/2}$ (h) | 8.96 ± 4.08 | 5.84 ± 1.52 | 6.54 ± 0.59 |
| $AUC_{0-36h}$ (ng · h/mL) | 424 ± 125 | 457 ± 163 | 2576 ± 54.8 |
| $AUC_{0-inf}$ (ng · h/mL) | 465 ± 148 | 501 ± 142 | 2612 ± 48.5 |
| Cl (mL/min/kg) | 92.8 ± 25.1 | 105 ± 28.8 | 19.1 ± 0.35 |
| Vdss (L/kg) | 46.2 ± 9.10 | 39.6 ± 5.06 | 5.51 ± 0.57 |

1.6 Conclusion

1) A single intravenous injection of an equal dose (10 mg/kg) was given to SD rats. The plasma exposure to paclitaxel from the micellar paclitaxel group of the present disclosure is significantly lower than that of paclitaxel injection group and that of Genexol-PM (Samyang, Korea) group, which indicates that the stability of the micellar paclitaxel of the present disclosure in vivo is significantly superior to that of the Genexol-PM (Samyang, Korea) and paclitaxel injection, and that the micellar paclitaxel of the present disclosure may be safer.

2) The half-life of paclitaxel in the micellar paclitaxel group of the present disclosure is significantly higher than that of paclitaxel injection group and Genexol-PM (Samyang, Korea) group, indicating that the micellar paclitaxel of the present disclosure may possess better therapeutic effects.

Example 64 Pharmacodynamic Study of Micellar Paclitaxel of this Invention on a Mouse Colo-205 Model 2.1 Animals Female BALb/c nude mice (5 weeks, 14-16 g) were obtained from Shanghai Sippr-BK laboratory animal Co., Ltd., with animal certificate number 20130016001491.

2.2 Feeding Conditions

Animals are fed in the experimental environment once arrived for 7 days before the experiment starting. Animals were housed in SPF animal house with IVC (Individually Ventilated Cages, 4 mice per cage) system. Animal information card of each cage indicated the number, sex, strain, date received, dosing schedule, experiment No., group, and experiment start date of animals in the cage. All of the cages, bedding and drinking water were sterilized before use. Cages, feed and water were changed twice a week.

2.3 Establishment of Xenograft Model

Human colorectal cancer Colo-205 cells (ATCC-CCL-222) were cultured in monolayer in vitro, in RPMI 1640 medium with 10% fetal bovine serum, 100 U/mL penicillin and 100 μg/mL streptomycin, in a incubator at 37° C. and 5% CO2. Routine digestion with trypsin-EDTA was performed twice a week. When the cell density reached 80%-90%, the cells were collected and counted. 0.2 mL (5×10$^6$ cells) Colo-205 cells were subcutaneously inoculated on the right back of each mouse. When the average tumor volume reached 163 mm$^3$, animals were randomized into groups.

2.4 Sample Preparation

1) Micellar paclitaxel: paclitaxel lyophilized powder prepared from Example 46 of the present disclosure. The weight ratio of paclitaxel to copolymer Ia (PEG-linker-PLA) is 30:100.

2) Genexol-PM: lyophilized powder of paclitaxel-load micelle of Samyang. The weight ratio of paclitaxel to copolymer (PEG-PLA) is 20:100.

3) Paclitaxel injection: purchased from Beijing SL Pharmaceutical Co., Ltd., 30 mg/5 ml*10, batch number: 20170501.

Lyophilized powder of micellar paclitaxel or Genexol-PM: An appropriate amount of normal saline was added to an appropriate amount of sample. The mixture was shaken at a speed of 200 r/min in shaker for about 20 minutes until it became clear prior to intravenous injection.

2.5 Drug Administration

Dosing schedules are presented in Table 2. Tumor volume under the skin, and weight of nude mice was measured 2-3 times a week.

TABLE 2

| No. | Group | Dose (mg/kg) | Administration Route | Quality | Cycle |
|---|---|---|---|---|---|
| 1 | Vehicle | 15 | IV | 6 | IV × 14 days |
| 2 | Micellar paclitaxel | 15 | IV | 6 | IV × 14 days |
| 3 | Genexol-PM | 15 | IV | 6 | IV × 14 days |
| 3 | Paclitaxel injection | 15 | IV | 6 | IV × 14 days |

Note: Dosing volume was calculated based on body weight. The dosing volume was 10 μL/g.

2.6 Analysis and Evaluation

Evaluation index: The tumor growth inhibition TGI (%) ratio or relative tumor proliferation T/C (%) ratio were used for evaluation, where T represents the experimental group and C represents the control group.

Calculation of T/C (%): If $T>T_0$, T/C (%)=$(T-T_0)/(C-C_0)\times 100\%$, if $T<T_0$, T/C (%)=$(T-T_0)/T_0\times 100\%$, where T and C represent tumor volumes at the end of the experiment, $T_0$ and $C_0$ represent tumor volumes at the beginning of the experiment.

Calculation of rate TGI (%): TGI (%)=$(1-T/C)\times 100\%$.

Evaluation criteria: Activity was defined as T/C (%)≤40 (that is, TGI (%)≥60%), and P<0.05 of statistical test.

2.7 Pharmacological Results

Figure 17:
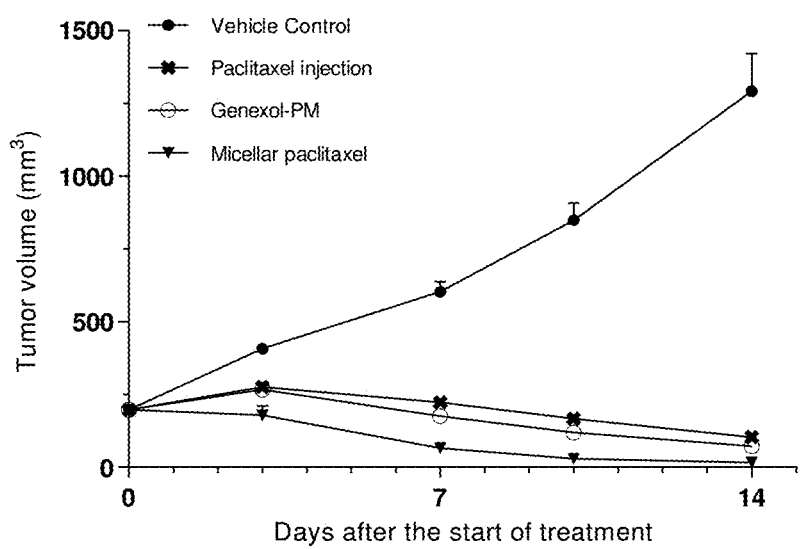
FIG. 17 is the inhibition effect graph of micellar paclitaxel from the present disclosure, micellar paclitaxel from Genexol-PM, and paclitaxel injection on the Colo-205 tumor volume.
Figure 18:
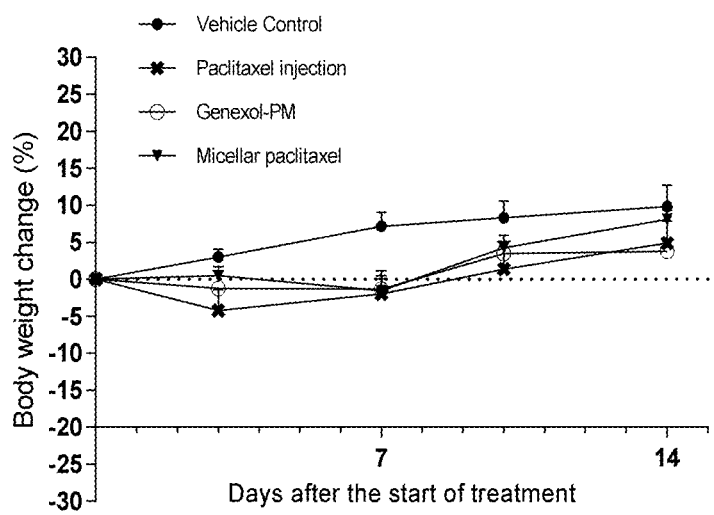
FIG. 18 is changing curve graph of micellar paclitaxel from the present disclosure, micellar paclitaxel from Genexol-PM, and paclitaxel injection on the weight of nude mice.

The inhibitory effects of micellar paclitaxel, Genexol-PM and paclitaxel injection on the Colo-205 tumor volume are shown in Table 3 and FIG. 17, and the weight change of nude mice is shown in FIG. 18.

TABLE 3

Inhibition effect of each group on Colo-205 tumor volume

| Group | route | Tumor volume (mm³) (day 0) | Tumor volume (mm³) (day 14) | T/C (%) | TGI (%) | P value |
|---|---|---|---|---|---|---|
| Vehicle | iv | 198 ± 12 | 1292 ± 129 | — | — | — |
| Micellar paclitaxel (15 mg/kg) | iv | 198 ± 10 | 16 ± 5 | −91.92 | 191.92 | 0.024 |
| Genexol-PM (15 mg/kg) | iv | 198 ± 13 | 72 ± 14 | −63.64 | 163.64 | 0.06 |
| Paclitaxel injection (15 mg/kg) | iv | 198 ± 15 | 103 ± 21 | −47.98 | 147.98 | 0.01 |

The results show:

1) The micellar paclitaxel of the present disclosure, Genexol-PM, and paclitaxel injection notably inhibits tumor growth of Colo-205 xenografted tumors. The efficacy of the micellar paclitaxel group of the present disclosure is better than that of the Genexol-PM group and paclitaxel injection group 2) In paclitaxel injection groups, the animals had dysuria and some death happened. Rupture of bladder were found after dead animals were dissected. All the animals in the micellar paclitaxel group of the present disclosure appeared normal, indicating that the safety of the micellar paclitaxel of the present invention is better than that of paclitaxel injection.

Example 65 Pharmacodynamic Study of Micellar Paclitaxel of this Invention on a Mouse MCF-7 Model 3.1 Animals Female BALb/c nude mice (6-8 weeks, 18-20 g) were obtained from Shanghai Lingchang Biotech Co., Ltd., with animal certificate number 2013001829943.

3.2 Feeding Conditions

Same as Example 2.2.

3.3 Establishment of Xenograft Model

Human breast cancer MCF-7 cells (ECACC 86012803) were cultured in monolayer in vitro, in EMEM(EBSS) medium with 2 mM Glutamine, 1% Nonessential Amino Acids (NEAA), 10% fetal bovine serum, 100 U/mL penicillin and 100 μg/mL streptomycin, in a incubator at 37° C. and 5% $CO_2$. Routine digestion with trypsin-EDTA was performed twice a week. When the cell density reached 80%-90%, the cells were collected and counted. 0.2 mL ($1\times10^7$ cells) MCF-7 cells mixing with Matrigel(v:v=1:1) were subcutaneously inoculated on the right back of each mouse. When the average tumor volume reached 209 mm³, animals were randomized into groups.

3.4 Sample Preparation

1) Micellar paclitaxel: paclitaxel lyophilized powder prepared from Example 36 of the present invention. The weight ratio of paclitaxel to copolymer Ia (PEG-linker-PLA) is 30:100.

2) Genexol-PM: lyophilized powder of paclitaxel-load micelle of Samyang. The weight ratio of paclitaxel to copolymer (PEG-PLA) is 20:100.

3) Paclitaxel injection: purchased from Beijing SL Pharmaceutical Co., Ltd., 30 mg/5 mL*10, batch number: 20170501.

Lyophilized powder of micellar paclitaxel or Genexol-PM: An appropriate amount of normal saline was added to an appropriate amount of sample. The mixture was shaken at a speed of 200 r/min in shaker for about 20 minutes until it became clear prior to intravenous injection.

3.5 Drug Administration

Dosing schedules are presented in Table 3. Tumor volume under the skin, and weight of nude mice was measured 2-3 times a week.

TABLE 4

| No. | Group | Dose (mg/kg) | Administration route | Quality | Cycle |
|-----|-------|--------------|----------------------|---------|-------|
| 1 | Vehicle | 15 | IV | 6 | IV × 14 days |
| 2 | Micellar paclitaxel | 15 | IV | 6 | IV × 14 days |
| 3 | Genexol-PM | 15 | IV | 6 | IV × 14 days |
| 3 | Paclitaxel injection | 15 | IV | 6 | IV × 14 days |

Note: Dosing volume was calculated based on body weight. The dosing volume was 10 μL/g.

3.6 Analysis and Evaluation

Evaluation index: The tumor growth inhibition TGI (%) ratio or relative tumor proliferation T/C (%) ratio was used for evaluation, where T represents the experimental group and C represents the control group.

Calculation of T/C (%): If $T>T_0$, T/C (%)=$(T-T_0)/(C-C_0)\times 100\%$, if $T<T_0$, T/C (%)=$(T-T_0)/T_0\times 100\%$, where T and C represent tumor volumes at the end of the experiment, $T_0$ and $C_0$ represent tumor volumes at the beginning of the experiment.

Calculation of rate TGI (%): TGI (%)=$(1-T/C)\times 100\%$.

Evaluation criteria: Activity was defined as T/C (%)≤40 (that is, TGI (%)≥60%), and P<0.05 of statistical test.

3.7 Pharmacological Results

Figure 19:
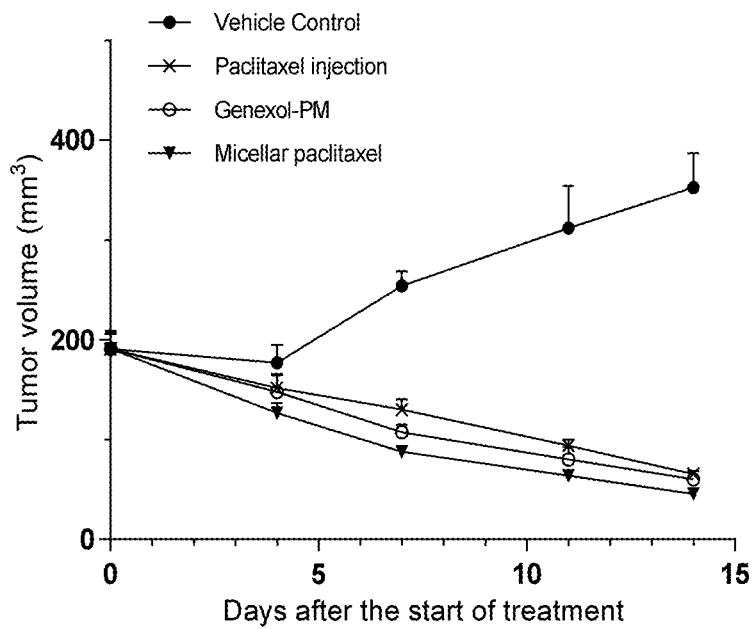
FIG. 19 is inhibition effect graph of micellar paclitaxel from the present disclosure, micellar paclitaxel from Genexol-PM, and paclitaxel injection on the MCF-7 tumor volume.
Figure 20:
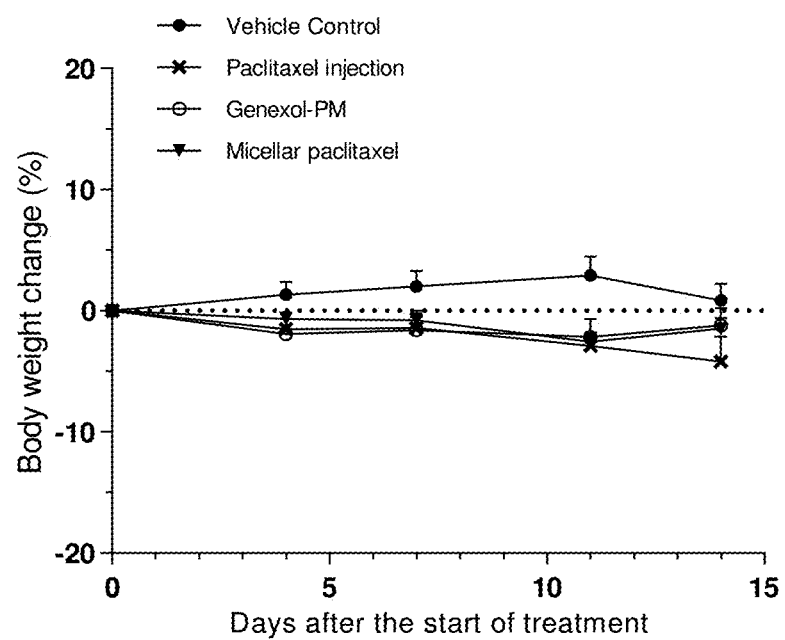
FIG. 20 is changing curve graph of micellar paclitaxel from the present disclosure, micellar paclitaxel from Genexol-PM, and paclitaxel injection on the weight of nude mice.
Figure 21:
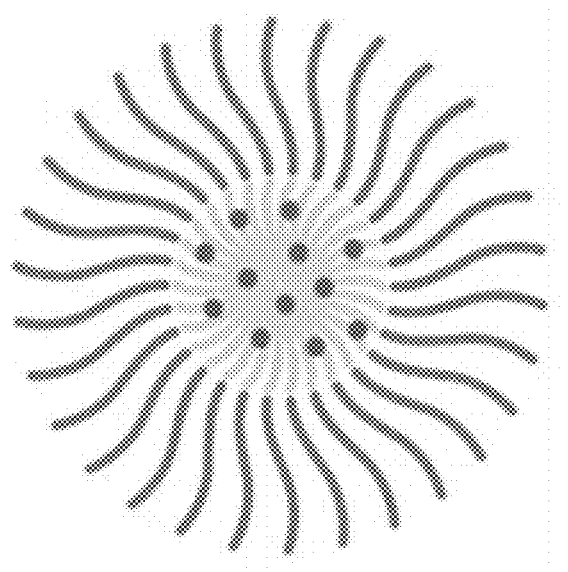
FIG. 21 is the state diagram of micelle from unmodified PEG-PLA.
Figure 22:
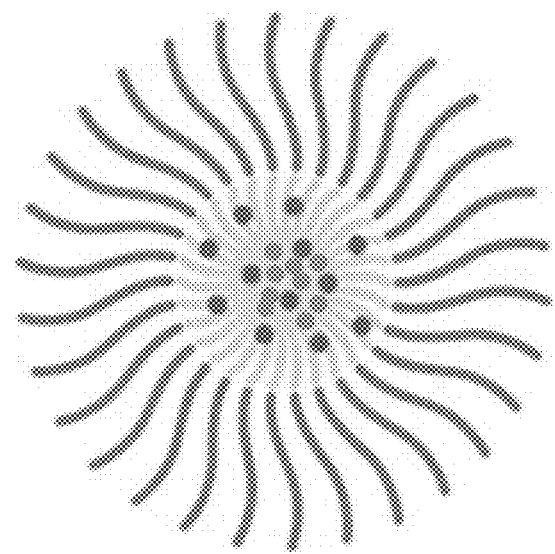
FIG. 22 is the state diagram of micelle from PEG-PLA with modification at the termini of PLA.
Figure 23:
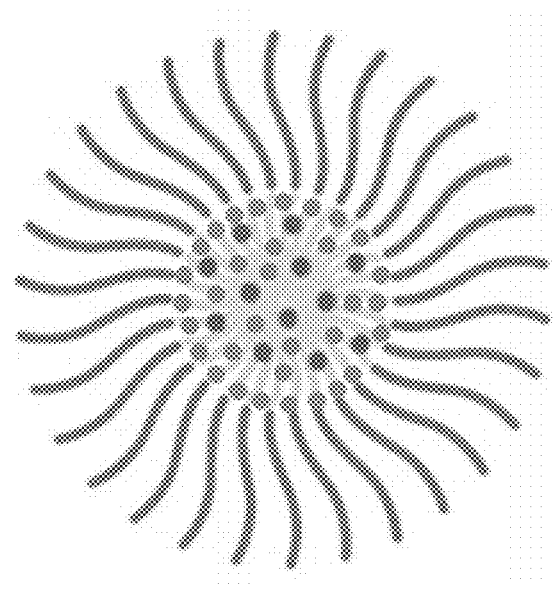
FIG. 23 is the state diagram of micelle from PLA-linker-PLA in the present disclosure.

The inhibitory effects of micellar paclitaxel of the present disclosure, Genexol-PM and paclitaxel injection on the MCF-7 tumor volume are set forth in Table 4 and FIG. 19, and the weight change of nude mice is set forth in FIG. 20.

TABLE 5

Inhibition effect of each group on MCF-7 tumor volume

| Group | route | Tumor volume ($mm^3$) (day 0) | Tumor volume ($mm^3$) (day 14) | T/C (%) | TGI (%) | P value |
|-------|-------|-------------------------------|--------------------------------|---------|---------|---------|
| Vehicle | iv | 191 ± 15 | 353 ± 5 | — | — | — |
| Micellar paclitaxel (15 mg/kg) | iv | 191 ± 18 | 45 ± 4 | −76.44 | 176.44 | 0.018 |
| Genexol-PM (15 mg/kg) | iv | 191 ± 15 | 60 ± 9 | −68.59 | 168.59 | 0.015 |
| Paclitaxel injection (15 mg/kg) | iv | 191 ± 17 | 65 ± 5 | −65.97 | 165.97 | 0.01 |

The results showed:

1) The micellar paclitaxel of the present disclosure, Genexol-PM, and paclitaxel injection significantly inhibits tumor growth of MCF-7 xenografted tumors. The efficacy of the micellar paclitaxel group of the present disclosure is better than that of the other two groups.

2) In paclitaxel injection groups, the animals had dysuria and some death happened. Rupture of bladder were found after dead animals were dissected. All the animals in the micellar paclitaxel group of the present disclosure appeared normal, indicating that the safety of the micellar paclitaxel of the present disclosure is better than that of paclitaxel injection.

List of abbreviations in the present disclosure is shown in table 6

TABLE 6

| Abbreviation | Full name |
|--------------|-----------|
| DBU | 1,8-Diazabicyclo[5.4.0]undec-7-ene |
| Me-PEG | Polyethyleneglycol monomethyl ether |
| PLA | Polylactic acid/Polylactide |
| Boc | t-Butoxycarbonyl |
| Fmoc | 9-Fluorenylmethyloxycarbonyl |
| TBSCl | Tertbutyldimethylsilyl chloride |
| DCC | Dicyclohexylcarbodiimide |
| NHS | N-hydroxy succinimide |
| EDCI | 1-(3-Dimethylaminopropyl)-3-ethylcarbodiimide Hydrochloride |
| DMAP | N,N-dimethylaminopyridine |
| Mn | Number-average molecular weight |

Structural formulas of some compounds in the Examples are shown in table 7

TABLE 7

| No. | Formula |
|-----|---------|
| Ia | (structure shown; $M_n = 3900$) |

TABLE 7-continued
| No. | Formula |
|---|---|
| Ib | 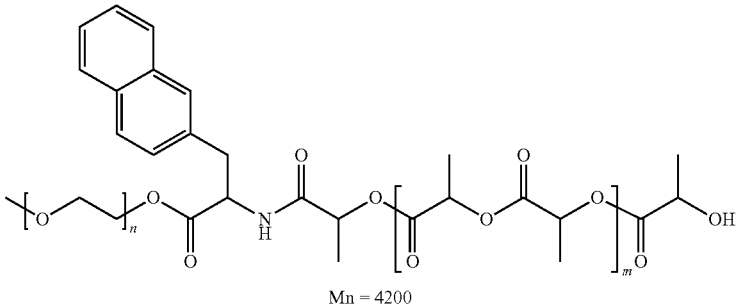<br>Mn = 4200 |
| Ic | 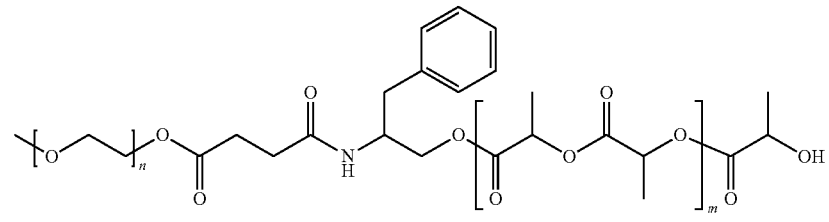<br>Mn = 4000 |
| Id | 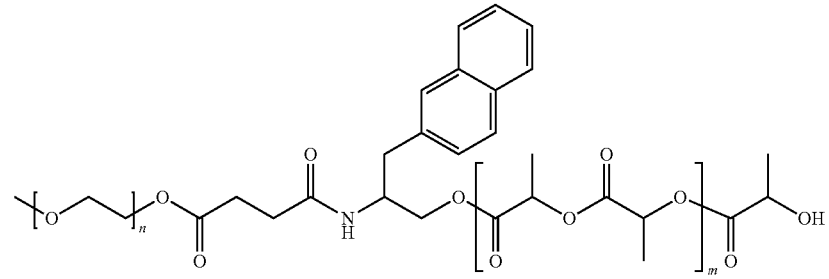<br>Mn = 4000 |
| Ie | 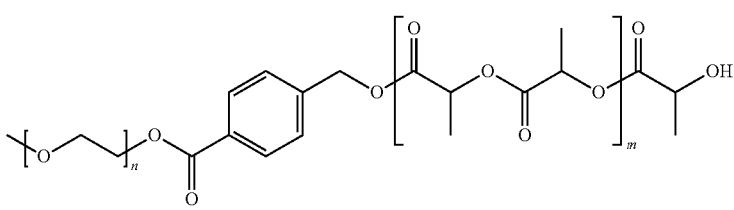<br>Mn = 3800 |
| If | 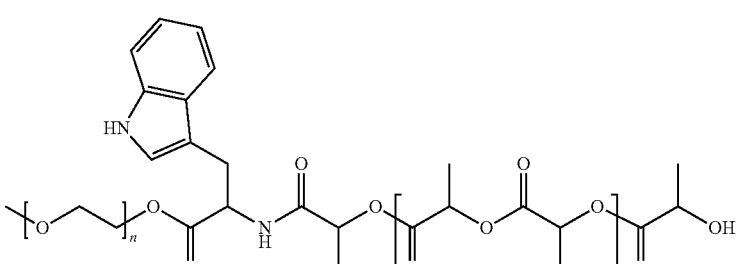<br>Mn = 7900 |

TABLE 7-continued
| No. | Formula |
|---|---|
| Ig | 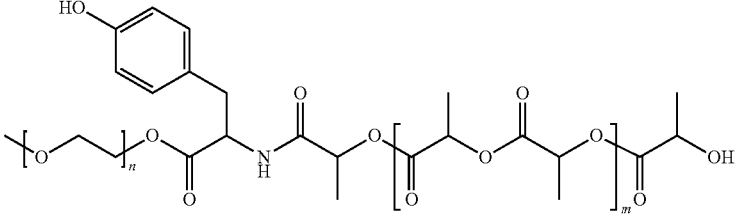  Mn = 10000 |
| Ih | 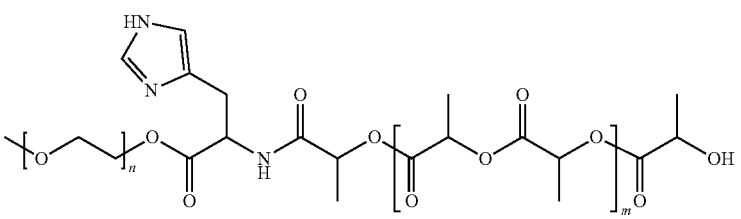  Mn = 5000 |
| Ii | 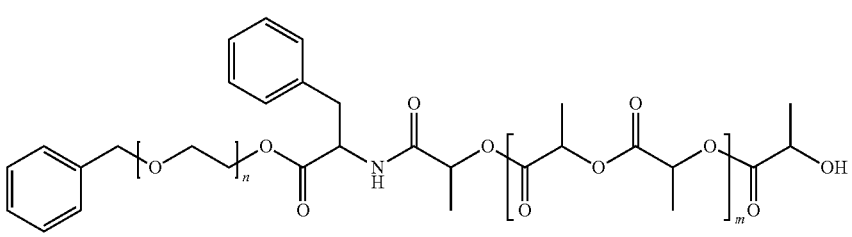  Mn = 4000 |
| Ij | 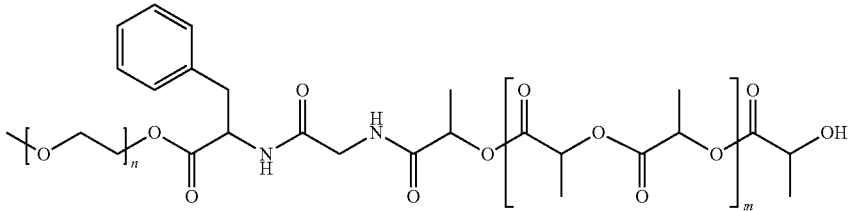  Mn = 20000 |
| Ik | 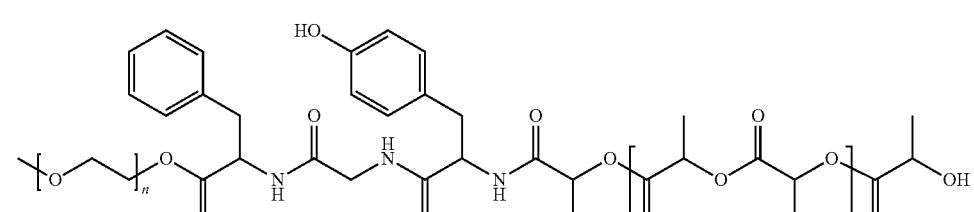  Mn = 14000 |
| Il | 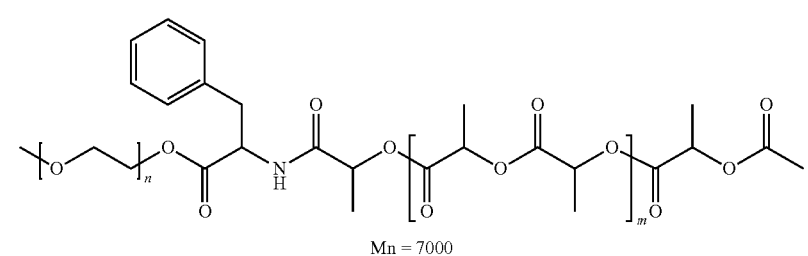  Mn = 7000 |

TABLE 7-continued
| No. | Formula |
|---|---|
| Im | 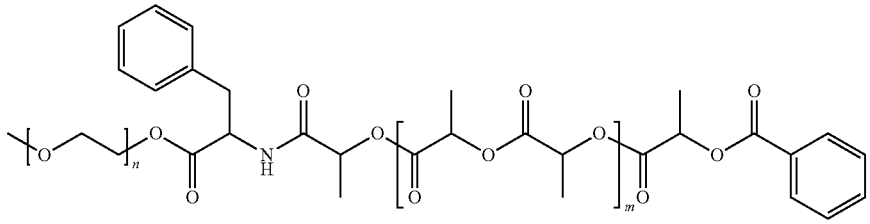 Mn = 4500 |
| In | 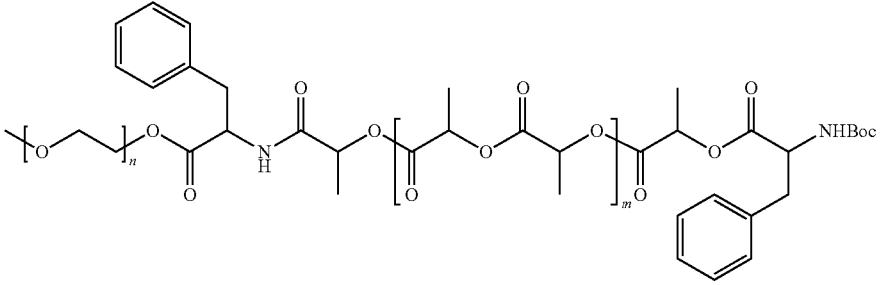 Mn = 5000 |
| Io | 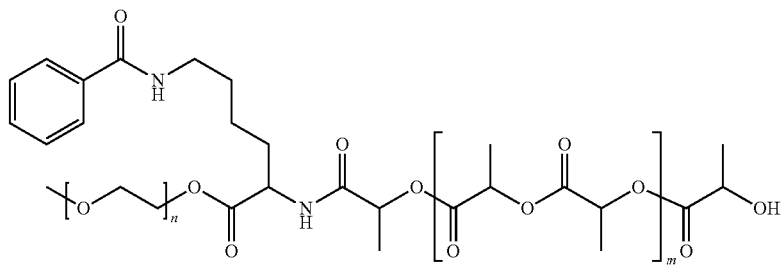 Mn = 4000 |
| Ip | 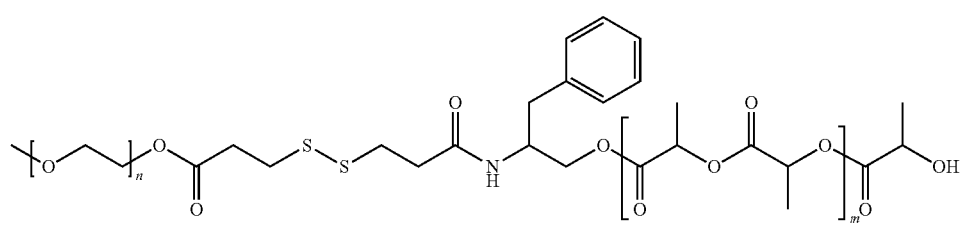 Mn = 4300 |
| Iq | 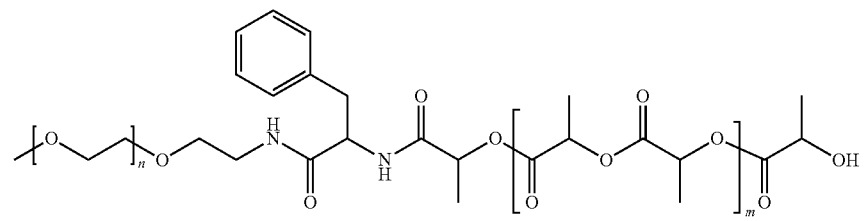 Mn = 5000 |

TABLE 7-continued
| No. | Formula |
|---|---|
| Ir | 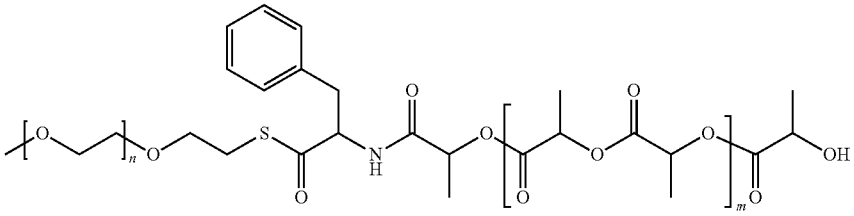<br>Mn = 6000 |
| Is | 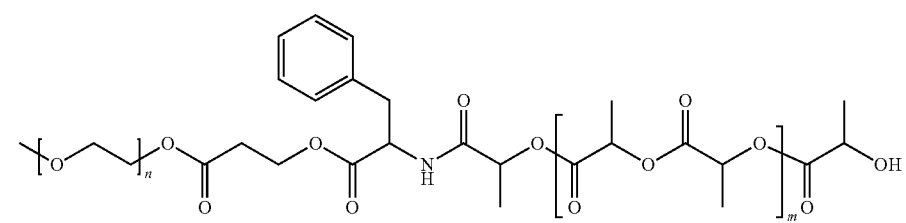<br>Mn = 8000 |
| It | 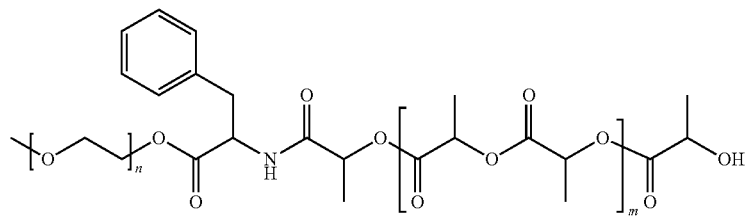<br>Mn = 9000 |
| Iu | 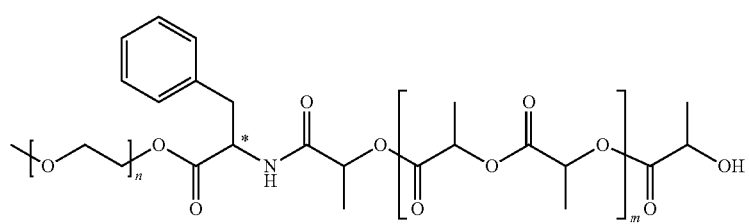<br>Mn = 8000 |
| Iv | 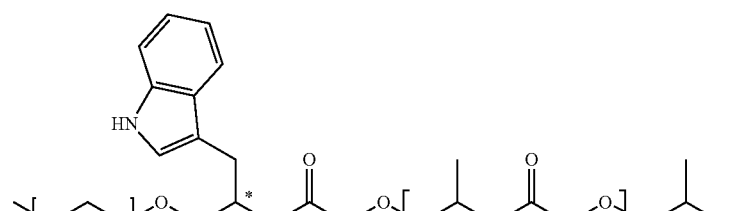<br>Mn = 30000 |

TABLE 7-continued

| No. | Formula |
|---|---|
| Iw | Mn = 40000 |
| Ix | Mn = 4200 |
| Iy | Mn = 4700 |
| Iz | Mn = 5000 |
| Ia' | Mn = 3900 |
| Iaa | Mn = 5200 |

TABLE 7-continued

| No. | Formula |
|---|---|
| IIa | (structure: mPEG-O-C(=O)-CH(CH2Ph)-NH-C(=O)-CH(OH)-CH3) |
| IIb | (structure: mPEG-O-C(=O)-CH(CH2-2-naphthyl)-NH-C(=O)-CH(OH)-CH3) |
| IIc | (structure: mPEG-O-C(=O)-CH2CH2-C(=O)-NH-CH(CH2Ph)-CH2OH) |
| IId | (structure: mPEG-O-C(=O)-CH2CH2-C(=O)-NH-CH(CH2-2-naphthyl)-CH2OH) |
| IIe | (structure: mPEG-O-C(=O)-C6H4-CH2OH) |
| IIIa | (structure: mPEG-O-C(=O)-CH(CH2Ph)-NH-C(=O)-CH(OTBS)-CH3) |

TABLE 7-continued
| No. | Formula |
|---|---|
| IIIb | 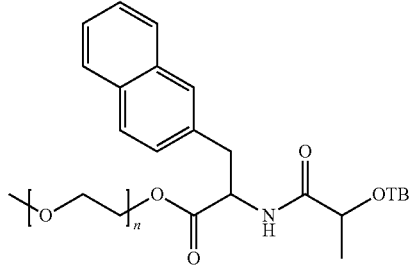 |
| IIIc | 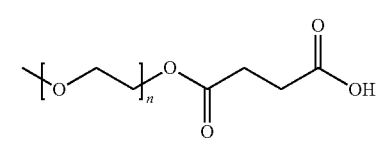 |
| IIIe | 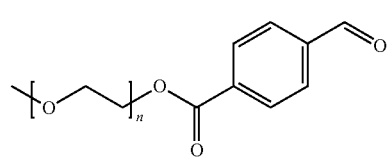 |
| IVa | 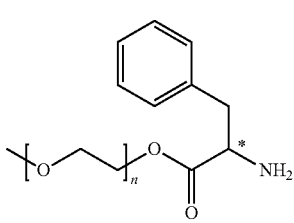 |
| IVb | 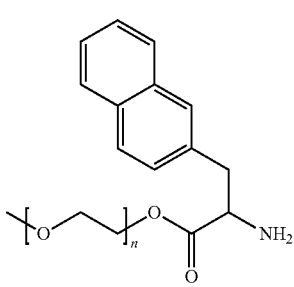 |
| Va | 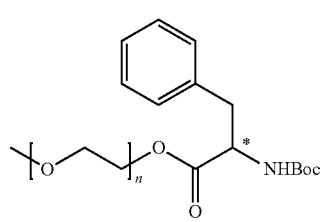 |
| Vb | 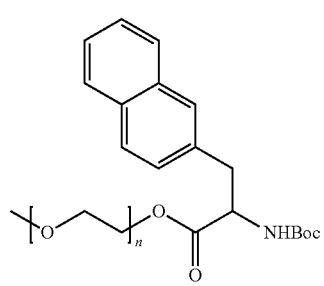 |

TABLE 7-continued

| No. | Formula |
|---|---|
| VIa | 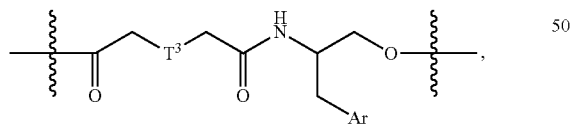 |
| Va' | |
| IVa' |  |

In the above table, the carbon with star ("*") is chiral carbon. The configuration of the chiral carbon can be R, S or racemic.

While the present disclosure has been described with reference to the specific examples, some modifications and equivalent variations will be apparent to those skilled in the art and are also within the scope of the present disclosure.

The invention claimed is:

1. An amphiphilic block copolymer comprising a hydrophilic chain segment, a hydrophobic chain segment and a linker used to connect the hydrophilic chain segment and the hydrophobic chain segment,
comprising the following structure:

wherein $T^3$ is a single bond or

;

wherein Ar is an aromatic ring, wherein the aromatic ring is
$C_6$-$C_{20}$ aryl,
$C_6$-$C_{20}$ aryl substituted with $R^a$,
$C_2$-$C_{20}$ heteroaryl, or
$C_2$-$C_{20}$ heteroaryl substituted with $R^b$;
  wherein each of $R^a$ and $R^b$ is independently selected from $C_1$-$C_6$ alkyl, $C_1$-$C_6$ alkoxy, $C_4$-$C_6$ cycloalkyl, a halide, a hydroxyl or a nitro group;
  wherein a number of $R^a$ is one or more; wherein when the number of $R^a$ is more than one, $R^a$ is the same or different;
  wherein a number of $R^b$ is one or more; wherein when the number of $R^b$ is more than one, $R^b$ is the same or different;
  wherein a heteroatom in the $C_2$-$C_{20}$ heteroaryl or the $R^b$ substituted $C_2$-$C_{20}$ heteroaryl is O, S or N; wherein a number of heteroatom(s) is one or more; and wherein when the number of heteroatoms is more than one, the heteroatoms are the same or different;
wherein the hydrophilic chain segment is a polyethylene glycol chain segment or a mono-protected polyethylene glycol chain segment with a number-average molecular weight ranging from 400 to 20000; and
wherein the hydrophobic chain segment is one chain segment selected from the group consisting of a polylactide chain segment, a mono-protected polylactide chain segment, a polyglycolide chain segment, a mono-protected polyglycolide chain segment, a poly (lactide-co-glycolide) chain segment, a mono-protected poly (lactide-co-glycolide) chain segment, a polycaprolactone chain segment, a mono-protected polycaprolactone chain segment, a polycarbonate chain segment, a mono-protected polycarbonate chain segment, a polydioxanone chain segment and a mono-protected polydioxanone chain segment, with a number-average molecular weight ranging from 400 to 20000.

2. The amphiphilic block copolymer according to claim 1, wherein, in the aromatic ring, the $C_6$-$C_{20}$ aryl or the $R^a$ substituted $C_6$-$C_{20}$ aryl is a $C_6$-$C_{10}$ aryl;

and/or, in the aromatic ring, the $C_2$-$C_{20}$ heteroaryl or the $R^b$ substituted $C_2$-$C_{20}$ heteroaryl is $C_2$-$C_{10}$ heteroaryl;

and/or, in $R^a$ or $R^b$, the $C_1$-$C_6$ alkyl is $C_1$-$C_3$ alkyl;

and/or, in $R^a$ or $R^b$, the $C_1$-$C_6$ alkoxy is $C_1$-$C_3$ alkoxy;

and/or, the $C_1$-$C_{30}$ small molecular fragment is a $C_2$-$C_{10}$ small molecular fragment;

and/or, the $C_1$-$C_{30}$ small molecular fragment is substituted by 1-3 aromatic rings;

and/or, the $C_1$-$C_{30}$ small molecular fragment optionally comprises a heteroatom substitution; wherein the heteroatom is one or more heteroatom(s) selected from the group consisting of oxygen, nitrogen, sulfur and phosphorus; and wherein the number of the heteroatom(s) is one or more; and/or, the hydrophobic chain segment is selected from a polylactide chain segment or a mono-protected polylactide chain segment with a number-average molecular weight ranging from 400 to 2000.

3. The amphiphilic block copolymer according to claim 1, wherein the aromatic ring is the $C_6$-$C_{10}$ aryl, the $R^a$ substituted $C_6$-$C_{10}$ aryl, the $C_2$-$C_{10}$ heteroaryl or a $R^b$ substituted $C_2$-$C_{10}$ heteroaryl; and wherein each of $R^a$ and $R^b$ is independently selected from $C_1$-$C_3$ alkyl, $C_1$-$C_3$ alkoxy, the halide, the hydroxyl or the nitro group.

4. An amphiphilic block copolymer comprising a hydrophilic chain segment, a hydrophobic chain segment and a linker used to connect the hydrophilic chain segment and the hydrophobic chain segment, wherein the structure of the linker is a $C_1$-$C_{30}$ small molecular fragment derived from amino acid(s) containing an aromatic ring other than phenylalanine, from an amino alcohol containing the aromatic ring, or from a peptide containing the aromatic ring;

wherein the aromatic ring is located in a side chain of the amino acid(s), amino alcohol or peptide, or is located in the protecting group of the hydroxy, thio, amino or carboxy functional group in the amino acid(s), amino alcohol or peptide, wherein the aromatic ring is $C_6$-$C_{20}$ aryl, $C_6$-$C_{20}$ aryl substituted with $R^a$, $C_2$-$C_{20}$ heteroaryl, or $C_2$-$C_{20}$ heteroaryl substituted with $R^b$;

wherein each of $R^a$ and $R^b$ is independently selected from $C_1$-$C_6$ alkyl, $C_1$-$C_6$ alkoxy, $C_4$-$C_6$ cycloalkyl, halide, hydroxyl or nitro group;

wherein a number of $R^a$ is one or more, and wherein when the number of $R^a$ is more than one, $R^a$ is the same or different;

wherein a number of $R^b$ is one or more, and wherein when the number of $R^b$ is more than one, $R^b$ is the same or different;

wherein a heteroatom in the $C_2$-$C_{20}$ heteroaryl or $R^b$ substituted $C_2$-$C_{20}$ heteroaryl is O, S or N; wherein a number of the heteroatom is one or more; and wherein when the number of the heteroatom is more than one, the heteroatoms is the same or different;

wherein the hydrophilic chain segment is a polyethylene glycol chain segment or a mono-protected polyethylene glycol chain segment with a number-average molecular weight ranging from 400 to 20000; and wherein the hydrophobic chain segment is a one chain segment selected from the group consisting of a polylactide chain segment, a mono-protected polylactide chain segment, a polyglycolide chain segment, a mono-protected polyglycolide chain segment, a poly (lactide-co-glycolide) chain segment, a mono-protected poly (lactide-co-glycolide) chain segment, a polycaprolactone chain segment, a mono-protected polycaprolactone chain segment, a polycarbonate chain segment, a mono-protected polycarbonate chain segment, a polydioxanone chain segment and a mono-protected polydioxanone chain segment, with a number-average molecular weight ranging from 400 to 20000.

5. The amphiphilic block copolymer according to claim 4, wherein the amino acid(s) containing the aromatic ring is one or more amino acids selected from the group consisting of histidine, tyrosine, tryptophan and 3-(2-naphthyl)-alanine;

and/or, wherein the amino alcohol containing the aromatic ring is one or more amino alcohol(s) selected from the group consisting of phenylalaninol, histidinol, tyrosinol, tryptosol and 3-(2-naphthyl)-alaninol;

and/or, wherein one or more building blocks in the peptide containing the aromatic ring is derived from one or more amino acid(s) selected from the group consisting of phenylalanine, histidine, tyrosine, tryptophan and 3-(2-naphthyl)-alanine.

6. The amphiphilic block copolymer according to claim 1, wherein the amphiphilic block copolymer is:

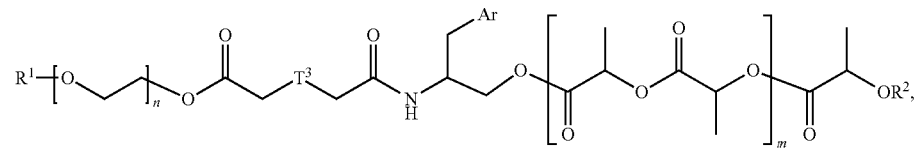

wherein each of $R^1$ and $R^2$ is independently selected from a hydroxyl protecting group or hydrogen;

wherein n=8-455; m=3-160; and wherein Ar and $T^3$ are as defined in claim 1.

7. An amphiphilic block copolymer selected from any one of the group consisting of:

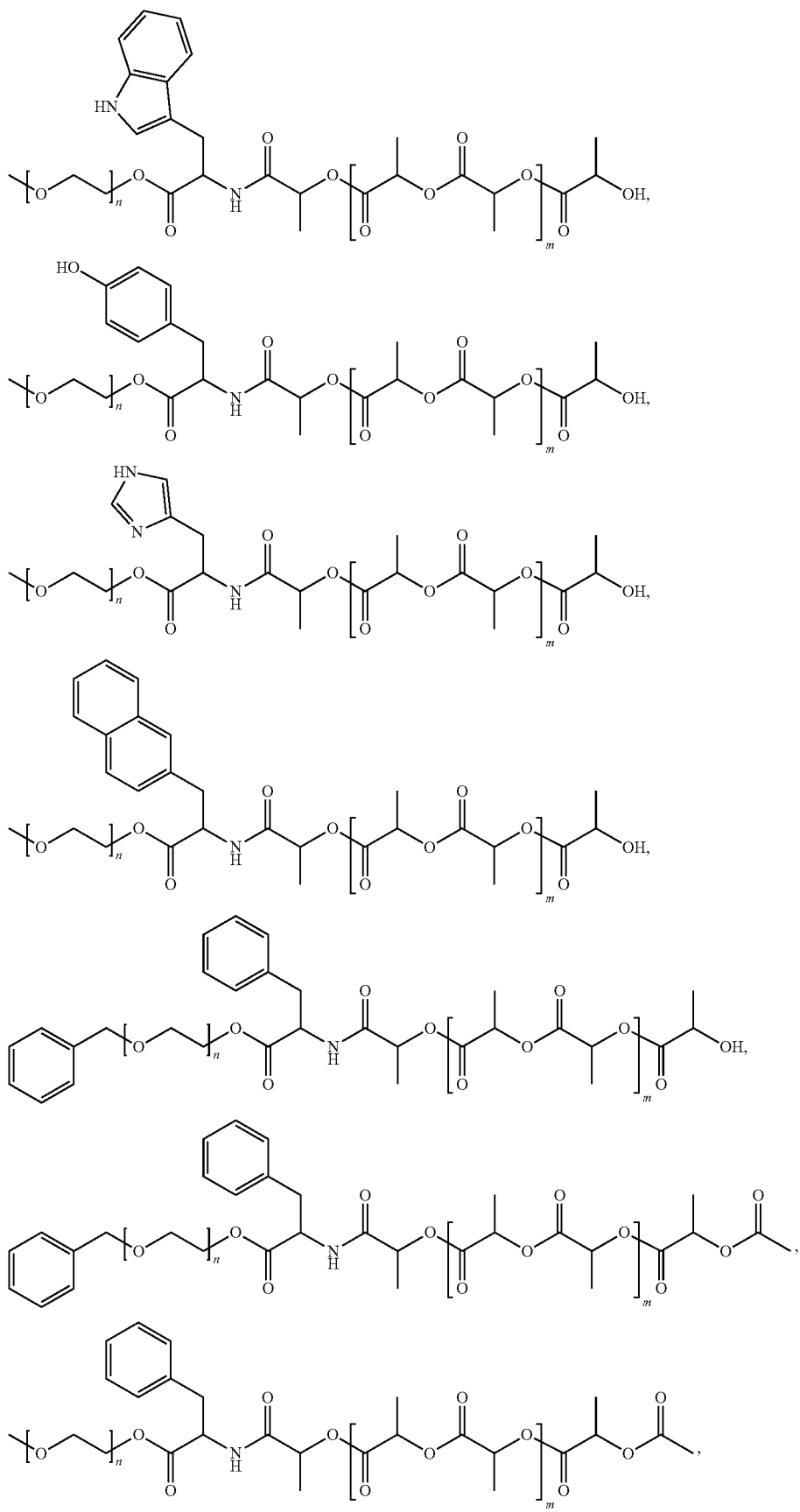

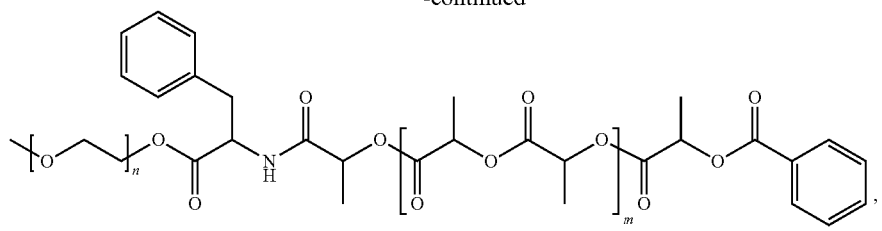
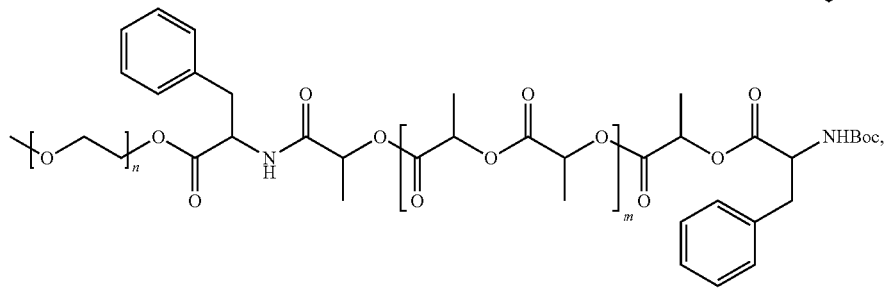
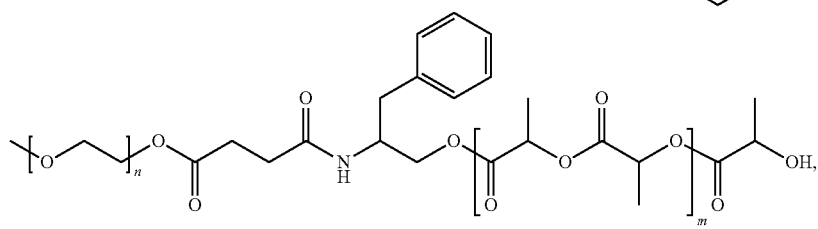
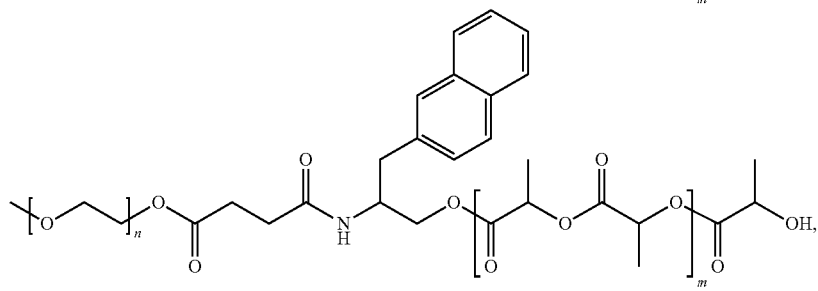
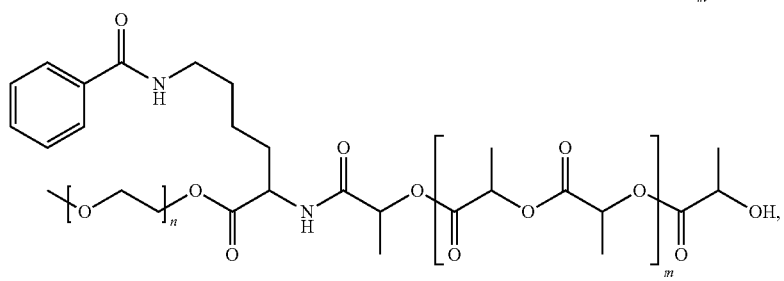
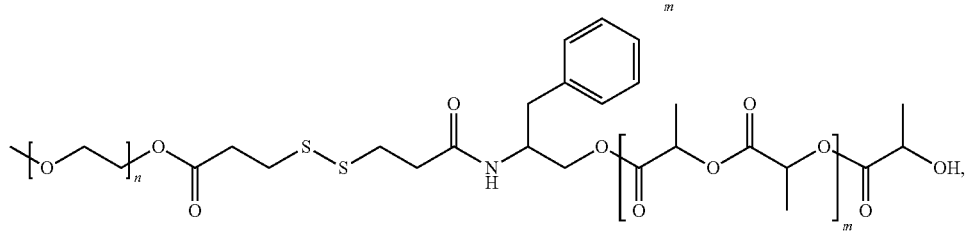
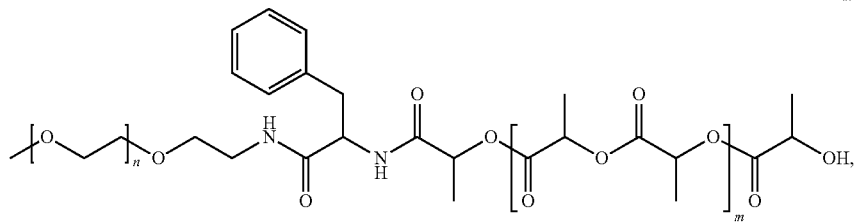

-continued

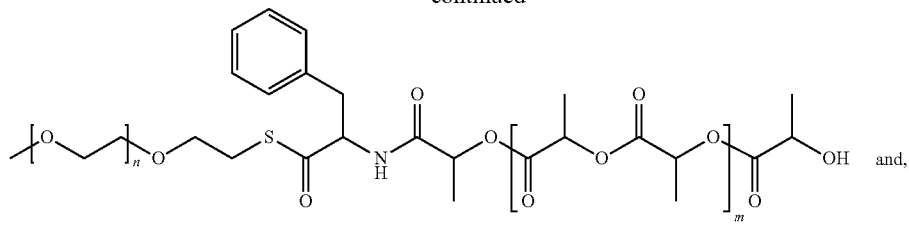

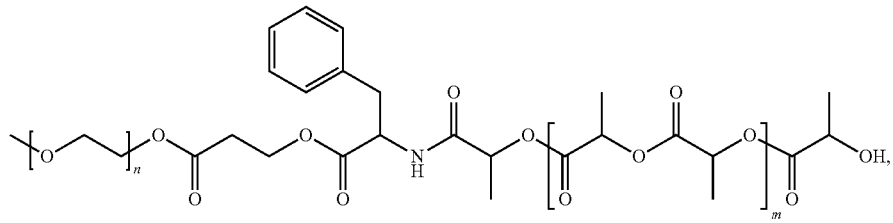

wherein n=8-455; and m=3-160.

8. An amphiphilic block copolymer selected from any one of the group consisting of:

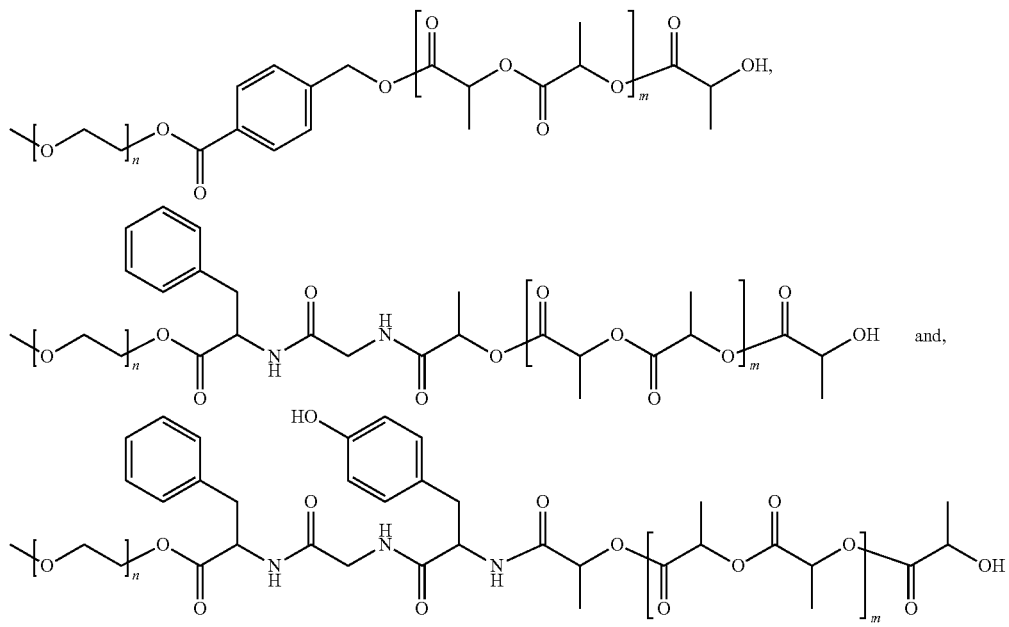

wherein
n=8-455; and m=3-160.

9. A method of preparing the amphiphilic block copolymer according to claim 1, comprising the following steps:
1) modifying polyethylene glycol or mono-protected polyethylene glycol with the linker;
2) in organic solvent, in the presence of catalyst, using the product from step 1) initiating polymerization of DL-lactide, L-lactide, or D-lactide, glycolide, a mixture of DL-lactide and glycolide with different ratios, a mixture of L-lactide and glycolide with different ratios, a mixture of D-lactide and glycolide with different ratios, caprolactone, a mixture of bisphenol A and diphenyl carbonate, or p-dioxanone;
3) optionally, protecting the terminal hydroxyl group of the polymer from step 2).

10. The method of claim 9, comprising the following steps:

1) in the presence of catalyst, initiating polymerization of lactide with a polymer of formula II to prepare a copolymer of formula IA, wherein the lactide is DL-lactide, L-lactide or D-lactide;

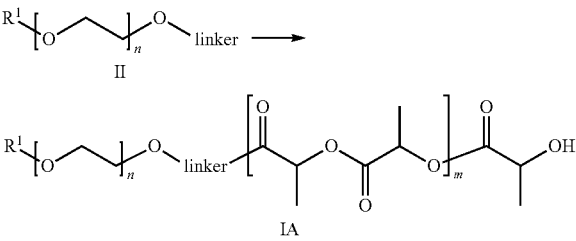

2) conducting a hydroxyl protecting reaction of the copolymer of formula IA to prepare the amphiphilic block copolymer of formula I;

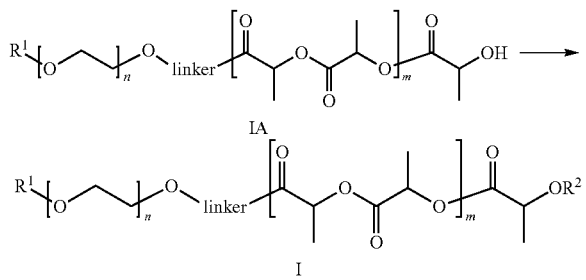

wherein the structure of the linker is the $C_1$-$C_{30}$ small molecular fragment substituted by one or more aromatic rings;
wherein the one or more aromatic rings is independently selected from $C_6$-$C_{20}$ aryl, $C_6$-$C_{20}$ aryl substituted with $R^a$, $C_2$-$C_{20}$ heteroaryl, or $C_2$-$C_{20}$ heteroaryl substituted with $R^b$;
wherein $R^a$ and $R^b$ are each independently selected from $C_1$-$C_6$ alkyl, $C_1$-$C_6$ alkoxy, $C_4$-$C_6$ cycloalkyl, halide, hydroxyl or nitro group;
the number of $R^a$ is one or more; wherein when the number of $R^a$ is more than one, $R^a$ is the same or different;
the number of $R^b$ is one or more; wherein when the number of $R^b$ is more than one, $R^b$ is the same or different;
wherein the heteroatom in the $C_2$-$C_{20}$ heteroaryl or $R^b$ substituted $C_2$-$C_{20}$ heteroaryl is O, S or N; wherein the number of heteroatom(s) is one or more; wherein when the number of heteroatom(s) is more than one, the heteroatoms are the same or different;
wherein $R^1$ and $R^2$ are each independently selected from hydroxyl protecting group or hydrogen;
wherein n=8-455; m=3-160; and
wherein when $R^2$ is hydrogen, step 2) is not performed.

11. The method according to claim 10, wherein the method further comprises modifying the polymer of formula III with the small molecular fragment to prepare the polymer of formula II;

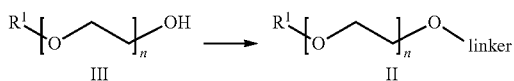

wherein the linker, $R^1$ and n are as defined in claim 10.

12. The method according to claim 9, wherein the catalyst in step 2) is one or more catalysts selected from the group consisting of 1,8-diazabicyclo[5.4.0]undec-7-ene, stannous octoate, magnesium 2-ethylhexanoate, 1,5,7-triazabicyclo[4.4.0]dec-5-ene and 7-methyl-1,5,7-triazabicyclo[4.4.0]dec-5-ene.

13. A nanomicelle drug-loading system, comprising the amphiphilic block copolymer according to claim 1 and drug.

14. The nanomicelle drug-loading system according to claim 13, wherein a weight ratio of the drug and the amphiphilic block copolymer is (0.5-100):100.

15. The nanomicelle drug-loading system according to claim 13, wherein the nanomicelle drug-loading system further comprises a pharmaceutically acceptable pharmaceutical ingredient.

16. A method of preparing the nanomicelle drug-loading system according to claim 13, wherein the preparation comprises dialysis, solvent evaporation or thin-film rehydration.

17. The amphiphilic block copolymer according to claim 2, wherein in the aromatic ring, the $C_6$-$C_{20}$ aryl or $R^a$ substituted $C_6$-$C_{20}$ aryl is phenyl or naphthyl;
and/or, in the aromatic ring, the $C_2$-$C_{20}$ heteroaryl or $R^b$ substituted $C_2$-$C_{20}$ heteroaryl is $C_3$-$C_8$ heteroaryl;
and/or, the $C_1$-$C_{30}$ small molecular fragment optionally comprises a heteroatom substitution; wherein the number of heteroatom(s) is 1-4.

18. The amphiphilic block copolymer according to claim 4, wherein,
in the aromatic ring, the $C_6$-$C_{20}$ aryl or the $R^a$ substituted $C_6$-$C_{20}$ aryl is $C_6$-$C_{10}$ aryl;
and/or, in the aromatic ring, the $C_2$-$C_{20}$ heteroaryl or $R^b$ substituted $C_2$-$C_{20}$ heteroaryl is $C_2$-$C_{10}$ heteroaryl;
and/or, in $R^a$ or $R^b$, the $C_1$-$C_6$ alkyl is $C_1$-$C_3$ alkyl;
and/or, in $R^a$ or $R^b$, the $C_1$-$C_6$ alkoxy is $C_1$-$C_3$ alkoxy;
and/or, the $C_1$-$C_{30}$ small molecular fragment is a $C_2$-$C_{10}$ small molecular fragment;
and/or, the $C_1$-$C_{30}$ small molecular fragment is substituted by 1-3 aromatic rings;
and/or, the $C_1$-$C_{30}$ small molecular fragment optionally comprises a heteroatom substitution; wherein the heteroatom is one or more heteroatom(s) selected from the group consisting of oxygen nitrogen, sulfur and phosphorus, wherein the number of heteroatom(s) is one or more;
and/or, the hydrophobic chain segment is one chain segment selected from a polylactide chain segment or a mono-protected polylactide chain segment with the number-average molecular weight ranging from 400 to 20000;
and/or, the configuration of the amino acid in the amino acid containing aromatic ring is R, S or racemic;
and/or, the configuration of the amino alcohol in the amino alcohol containing aromatic ring is R, S or racemic.

19. The preparation method of the amphiphilic block copolymer according to claim 12, wherein the catalyst in step 2) is 1,8-diazabicyclo[5.4.0]undec-7-ene and/or stannous octoate.

20. The nanomicelle drug-loading system according to claim 14, wherein the weight ratio of the drug and the amphiphilic block copolymer is (1-70):100;
and/or, the drug is selected from the group consisting of paclitaxel, docetaxel, cabazitaxel, 7-epipaclitaxel, t-acetylpaclitaxel, 10-deacetylpaclitaxel, 10-deacetyl-7-epipaclitaxel, 7-xylosylpaclitaxel, 10-desacetyl-7-glutarylpaclitaxel, 7-N,N-dimethylglycylpaclitaxel, 7-L-alanylpaclitaxel, larotaxel, doxorubicin, epirubicin, SN-38, irinotecan, topotecan, cyclophosphamide, ifosfamide, estramustine, mitoxantrone, amsacrine, cisplatin, carboplatin, oxaliplatin, etoposide, teniposide, vinblastine, vincristine, vinorelbine, vindesine, maytansine, harringtonine, homoharringtonine, mitomycin, bleomycin, daunorubicin, idarubicin, doxorubicin, epirubicin, gemcitabine, capecitabine, fludarabine, cladribine, bortezomib, carfilzomib, ixazomib, carmustine, fluorouracil, cytarabine, cyclosporin A, sirolimus, temsirolimus, everolimus, eribulin, trabectedin, fulvestrant, letrozole, temozolomide, raloxifene, tamoxifen, lenalidomide, ixabepilone, methotrexate, pemetrexed, enzalutamide, abiraterone, bendamustine, curcumin, resveratrol, indomethacin, huperzine A, acyclovir, allopurinol, amiodarone, azathioprine, benazepril, calcitriol, candesartan, eprosartan, carbidopa/levodopa, clarithromycin, clozapine, desmopressin acetate, diclofenac, enalapril, famotidine, felodipine, fenofibrate, fentanyl, fexofenadine, fosinopril, furosemide, glibenclamide, scopolamine, imipramine, itraconazole, levothyroxine, atorvastatin, lovastatin, meclizine, megestrol, thiopurine, metolazone, mometasone, nabumetone, omeprazole, paroxetine, propafenone, quinapril, simvastatin, sirolimus, tacrolimus, tizanidine, risperidone, olanzapine, ziprasidone, rivastigmine, naloxone, naltrexone, sirolimus, tacrolimus, carmustine, progesterone, estrogen, estradiol, levonorgestrel, norethisterone, ixabepilone, epothilone, rapamycin, plicamycin, vancomycin, amphotericin B, etoposide, doxycycline, itraconazole, fluconazole, voriconazole, posaconazole, ketoconazole, testosterone, progesterone, triamcinolone, dexamethasone, tenoxicam, piroxicam, ibuprofen, caspofungin, micafungin, olaparib, butylphthalide, combretastatin, GW6471, COX-II inhibitor, aromatase inhibitor, peptide drugs and a combination thereof.

21. The nanomicelle drug-loading system according to claim 15, wherein the pharmaceutically acceptable pharmaceutical ingredient comprises a freeze-dried excipient.

22. The nanomicelle drug-loading system according to claim 21, wherein the freeze-dried excipient is one or more excipients selected from the group consisting of lactose, mannose, sucrose, trehalose, fructose, glucose, sodium alginate and gelatin.

23. The method of claim 2 wherein the preparation method comprises thin-film rehydration.

* * * * *